United States Patent
Barry et al.

(10) Patent No.: US 11,213,028 B2
(45) Date of Patent: Jan. 4, 2022

(54) INSECTICIDAL PROTEINS AND METHODS FOR THEIR USE

(71) Applicant: PIONEER HI-BRED INTERNATIONAL, INC., Johnston, IA (US)

(72) Inventors: Jennifer Kara Barry, Ames, IA (US); Hua Dong, Johnston, IA (US); James English, San Ramon, CA (US); Jacob Gilliam, Norwalk, IA (US); Kai M. Hillman, Madison, WI (US); Daniel James Thorpe, Johnston, IA (US); Thomas Chad Wolfe, Des Moines, IA (US); Nasser Yalpani, Kelowna (CA)

(73) Assignee: PIONEER HI-BRED INTERNATIONAL, INC.

( * ) Notice: Subject to any disclaimer, the term of this patent is extended or adjusted under 35 U.S.C. 154(b) by 0 days.

(21) Appl. No.: 16/470,688

(22) PCT Filed: Dec. 18, 2017

(86) PCT No.: PCT/US2017/067107
§ 371 (c)(1),
(2) Date: Jun. 18, 2019

(87) PCT Pub. No.: WO2018/118811
PCT Pub. Date: Jun. 28, 2018

(65) Prior Publication Data
US 2019/0364894 A1 Dec. 5, 2019

Related U.S. Application Data

(60) Provisional application No. 62/438,179, filed on Dec. 22, 2016.

(51) Int. Cl.
*A01N 37/46* (2006.01)
*C07K 14/32* (2006.01)
*C12N 15/82* (2006.01)

(52) U.S. Cl.
CPC .............. *A01N 37/46* (2013.01); *C07K 14/32* (2013.01); *C12N 15/8286* (2013.01)

(58) Field of Classification Search
None
See application file for complete search history.

(56) References Cited

PUBLICATIONS

Kim 2015 (Genbank: ALO41133.1). (Year: 2015).*
Guo et al. (PNAS (2004) 101: 9205-9210) (Year: 2004).*
Berry, Colin: "The bacterium, Lysinibacillus sphaericus, as an insect pathogen", Journal of Invertebrate Pathology, Oct. 12, 2011 (Oct. 12, 2011), vol. 109, pp. 1-10.
Berry, Colin: "Structural classification of insecticidal proteins—Towards an in silico characterisation of novel toxins", Journal of Invertebrate Pathology, Jul. 29, 2016 (Jul. 29, 2016), vol. 142, pp. 16-22.
Narva, Kenneth E., et al.: "Transgenic Approaches to Western Corn Rootworm Control", Adv Biochem Eng Biotechnol, Jan. 1, 2013 (Jan. 1, 2013), vol. 136, pp. 135-162.
Wei, Jun-Zhi, et al.: "A selective insecticidal protein from Pseudomonas mosselii for corn rootworm control", Plant Biotechnology Journal, Feb. 1, 2018 (Feb. 1, 2018), vol. 16, pp. 649-659.
Yalpani, Nasser, et al.: "An Alcaligenes strain emulates Bacillus thuringiensis producing a binary protein that kills corn rootworm through a mechanism similar to Cry34Ab1/Cry35Ab1", Scientific Reports, Jun. 8, 2017 (Jun. 8, 2017), vol. 7, No. 1, Entire Document.
UniProt Database Accession No. R7Z7R9 dated Jul. 24, 2013 (Jul. 24, 2013).
UniProt Database Accession No. A0A0N0CV19 dated Dec. 9, 2015 (Dec. 9, 2015).
International Search Report and Written Opinion, International Application No. PCT/US2017/067107 dated Mar. 4, 2018.

* cited by examiner

*Primary Examiner* — Matthew R Keogh

(57) ABSTRACT

Compositions and methods for controlling pests are provided. The methods involve transforming organisms with a nucleic acid sequence encoding an insecticidal protein. In particular, the nucleic acid sequences are useful for preparing plants and microorganisms that possess insecticidal activity. Thus, transformed bacteria, plants, plant cells, plant tissues and seeds are provided. Compositions are insecticidal nucleic acids and proteins of bacterial species. The sequences find use in the construction of expression vectors for subsequent transformation into organisms of interest including plants, as probes for the isolation of other homologous (or partially homologous) genes. The pesticidal proteins find use in controlling, inhibiting growth or killing Lepidopteran, Coleopteran, Dipteran, fungal, Hemipteran and nematode pest populations and for producing compositions with insecticidal activity.

9 Claims, 5 Drawing Sheets
Specification includes a Sequence Listing.

Figure 1(a)

```
              1                                                           60
IPD101Aa  (1) -MH  IDIDLKLKQGFR LFPE YAAKLEKA SQVE INK QAEF IEER-----KQILAEAL
IPD101Ab  (1) -MH  IDIDLKLKQGFR LFPE YAAKLEKA SQVE INK QAEF IEER-----KQILAEAL
IPD101Ac  (1) -MN  IDIDLKLKEGFR LFPE YAAKLEKA SQVE INT QAEF IEER-----KQILAEAL
IPD101Ba  (1) -MH  LDIDFKLKEGFR SLFPDYATKLEKA SQEE INRFQAEF IEER-----KQILAEAL
IPD101Ca  (1) -MH  IDIDLKLKQGFR SLFPDYAT KLEKA SSQEE INK QTIF IEER-----KQALADAL
IPD101Cb  (1) -MH  IDIDLKLKQGFR SLFPDYAT KLEKA TSQEE INR QAIF IEER-----KQALADAL
IPD101Cc  (1) -MQ  IDIDLKLKQGFR SLFPDYAT KLERA TSQEE INK QAIF IEER-----KQALADAL
IPD101Cf  (1) -MH  IDIDLKLKQGFR SLFPDYAT KLEKA TSQEE INK QAIF IEER-----KQALADAL
IPD101Cd  (1) -MH  IDIDLKLKQGFR SLFPDYAT KLEKA TSQEE INQ QATF IEER-----KLELAKVL
IPD101Ce  (1) -MQISHDIDLKLKQGFR SVFPQYAMKLEKA TSQEE INN HATF IKER-----KLALANAL
IPD101Ea  (1) -MYDADN IDVKLKQGFQSLFPEYAT LLNQA SQEQ ISLHNSF IEER-----KKALATA
IPD101Eb  (1) -MYDADN IDVKLKQGFQSLFPEYAT LLNQA ISQEQ ISLHNSF IEER-----KKALATA
IPD101Ee  (1) -MH  KDIDLKLKQGFR LFPNYAQKLEKA TSQAD INQLHALF IKEQ-----QQKLADVL
IPD101Fa  (1) -MDSSFNMDLKLKQSF QSLFPEYASKLEKASSPEELNQLHNDF VKEQ-----KKEFART
IPD101Fb  (1) ----MS SLQNL KSKF SEVFPEHAKLLEGAR SHTEVLKLQDRF QLEF-----KTKLASAL
IPD101Ga  (1) -----MDNVMSVKERF KKLYFQEAQAFENAK SDEELTALKNQF LLEAKQRLIQEIEKTDL
IPD101Gb  (1) MDNQLNNDLLQIKKKF EEMFPNYASRLEAAT QQMNNETLEDTLKVEADIEAIQKEMIDR
IPD101Gc  (1) ----------MKSLLEKNHFSLYEKLENEQCNEKKQEAYYERVQSS--------------
IPD101Gd  (1) --MF  KSEL NLKTS GNAY FDYFKQLEACNKQQELADTYEKIKADA------FEKAKPFL
IPD101Ge  (1) --MF  KLEL NLKTS NF AYFE CSQLDACF ETELLETYEKIKEDA------FAKAKPY
IPD101Gf  (1) -MGKIRINKKQHQKKIQLLYKELAKEF ENNDIHKVLTKLEVNYDEEK---LNEAIYKIKT 61                                                         120
IPD101Aa  (55) CKDISELKASD--QTAPIPLSGDT YKML INATCDDIKRQLHVLIDCLERLKGMEK--DEA
IPD101Ab  (55) CKDISELKASD--QTAPIPLSGDT YKTLINATCDDIKRQLHVLIDCLERLKGMEK--DEA
IPD101Ac  (55) CKDISELKASD--QTAPIPLSGDMYKMLINATCDDIKRQLHVLIDCLERLKGMEK--DEA
IPD101Ba  (55) CKDISELEASD--QTAPIPLKQDMYKILINATCDDIKKQLHVLIDCLNRLQSMED--DDA
IPD101Ca  (55) CKDITELEASD--QTAAIPLKKETYEILVNATCDDIKRQLHVLIDCLERLKCLEK--DDA
IPD101Cb  (55) CKDISELEASD--QTAPIPLKKETYEILINATCDDIKRQLHVLIDCLERLKGMEN--DEA
IPD101Cc  (55) CKDISELEASD--QTAPIPLKKETYEILINATCDDIKRQLHVLIDCLERLKGMEN--DEA
IPD101Cf  (55) CKDISELQASD--QTAAIPLKKETYDILINATCDDIKRQLHVLIDCLERLKGMEK--DDA
IPD101Cd  (55) CKDILELNASD--YTAPFPLKKETYEILVNATCDTIKKQLHVLIDCLERLKGMEN--DEA
IPD101Ce  (55) CKDISVLEEKD--YYCATPLKKETYQNLLNWTGEDIKRQLQILIDCLQRLKDMEN--DDA
IPD101Ea  (55) KATNISDSRNP---KSPIALT QEFYENLINATCDDIKYRLQALLDCLQRLKGMEN--DQI
IPD101Eb  (55) KATNISDSRNP---KSPIALT QEFYENLINATCDDIKYRLQALLDCLQRLKGMEN--DQI
IPD101Ee  (55) CKELKDTQN-----QCSVALTISQFESLLNARCDDIKKQLQYLIDCLQRLKALEKR-GDS
IPD101Fa  (55) CKDVSALEVGEVEYNVAIALINDQYLQLLNAKCEDIKALLQTLLDGAKRIKEREH--DEK
IPD101Fb  (52) NIKLDSLDDRKT--QPAFALKPATYNALINATCGALEQQLHDLLTSFQSLSKMEH--DDP
IPD101Ga  (56) KNTVDLEALKGTDEIVAVALESVYKTLINARCDQFETELIKFFDTVERLKDMGT--QDA
IPD101Gb  (61) VSDVKKVSNNDITEGFAIQLSLDKYNDLINAKCDSIETQLLRLMDSLERLKDIDK--SDS
IPD101Gc  (37) ----NKIEKAD------FFTLLPDKRAALLDSTCKSIEKELKSLVDCLSDIADMVDKKKSH
IPD101Gd  (54) AEGDDPTGFP-------ALALTQQYNNLISAQCDNIKVYYTAMLNTAQLKQPSFN----V
IPD101Ge  (54) AAGDDPTGFP-------ALALTPQQYNNLKSAECSNIKVYYTAMLNQAQIKQPSFS----V
IPD101Gf  (57) NLNRQGALMK-----QAQILYDPKKVFEFINSNCDKIRVQVQKYLIDVERISKMED--DDA
```

Figure 1(b)

```
                 121                                                        180
IPD101Aa  (111)  GLVTAQIVLSGALGIGSLATIEVVRNLAMG------------------------------
IPD101Ab  (111)  GLVTAQIVLSGALGIGSLATIEVVRNLAMG------------------------------
IPD101Ac  (111)  GLVTAQIVLSGALGIGSLATIEVVRNLAMG------------------------------
IPD101Ba  (111)  GLVTAQILVSGALGIGLLSTSTVIAKLAVG------------------------------
IPD101Ca  (111)  GLVTAQILLSGVLGIGFLSTSTVVAKLAVG------------------------------
IPD101Cb  (111)  GLVTAQILLSGVLGIGFLSTSTVVAKLAVG------------------------------
IPD101Cc  (111)  GLVTAQILLSGVLGVGFLSTSTVVAKLAVG------------------------------
IPD101Cf  (111)  GLVTAQILLSGVLGIGSLAISEVVIKLAAG------------------------------
IPD101Cd  (111)  GLVTAQMLLSGVLGIGLLSTSTVVAKLAVG------------------------------
IPD101Ce  (111)  GLVTAQILLSGALGVGMLSTSTVIARLVSG------------------------------
IPD101Ea  (110)  EHVAAQMIVTGILGIGVESTAALAIAGGG------------------------------
IPD101Eb  (110)  EHVAAQMIVTGILGIGVESTAALAIAGGG------------------------------
IPD101Ee  (109)  CVVMAQMLLAGVLGIGPKSIDGAMEYTAKNSSPSK----------------EDELMV
IPD101Fa  (113)  GVIAAQMLLAGIIGIGPESIEGAMNYLNSLNKEKKSVVATDPALLAKELGVDQSMVVGFP
IPD101Fb  (108)  KDAVATMFAGGITSLGLTAIAAYQSKLVMG------------------------------
IPD101Ga  (114)  EVLTYAMVNGGIAALGIAMVTDLILNLLQG------------------------------
IPD101Gb  (119)  EALTATILGGGLSAITAAGITYFAHCTTAQ------------------------------
IPD101Gc   (88)  SETADKMMDVGVAAFGVLATEAFENTLKDHDKIT--------------------------
IPD101Gd  (104)  GQTVASLNGGGITAIGTIAGAAFGEGIVGG------------------------------
IPD101Ge  (104)  GQTVATLIGGGLTAIGTIAGAAFGTGIIGG------------------------------
IPD101Gf  (111)  IETSMAIIGISAAAVGVIAGITYFVQLIRG------------------------------

181                                                        240
IPD101Aa  (141)  ---AAETVAAFAGVTV-ATVGVVVAVASLVIVGVIIPIIY-FMQKPANAVVLLINEL---
IPD101Ab  (141)  ---AAETVAAFAGVTV-ATVGVVVAVASLVIVGVIIPIIY-FMQKPANAVVLLINEL---
IPD101Ac  (141)  ---AAETVAAFAGVTV-ATVGVVVAVASLVIVGVIIPIIY-FMQKPANAVVLLINEL---
IPD101Ba  (141)  ---AAEAVAAFAGVTV-ASVGAVVALAALVIVAIIIPIIY-FMAKPANAVVLLINEL---
IPD101Ca  (141)  ---AAEAIAALAGVTA-ATVGVVVAVAALVIVALIIPIIY-FMKKPANAVVLLINEL---
IPD101Cb  (141)  ---AGEAIAALAGVSV-ATVGVVVAVAALVIVATIIPIIY-FMKKPANAVVLLINEL---
IPD101Cc  (141)  ---AAEAIAALAGVSV-ATVGVVVAVAALVIVATIIPIIY-FMKKPANAVVLLINEL---
IPD101Cf  (141)  ---AAEAVAALAGVIT-ATVGVVVALAALVIVATIIPIIY-FMTKPANAVVLLINEL---
IPD101Cd  (141)  ---AVEAVAALAGVIA-ATVGVVVAVVALVIVSIIIPIIY-FMEKPANAVVLLINEL---
IPD101Ce  (141)  ---AIEAVAAFAGVEA-ATVSVVVGIVSLIVATIIPIIY-FMAKPANAIILLINEL---
IPD101Ea  (140)  --EIIPAYIALAALTS-TIVAVVIAVVCLVIIAIIIPLIY-FMEKPANALILLINEL---
IPD101Eb  (140)  --EIIPAYIALAALTS-TIVAVVIAVVCLVIIATIIPLIY-FMEKPANALILLINEL---
IPD101Ee  (150)  TPELIDAYIALAGLSS-ATVAYVIAIVSLAVVILLIPIIYY-EKDAKALIFLINEL---
IPD101Fa  (173)  PAEIIAGYAAIAALGSPAIIAYVVLLVSIVISSILIGLLIYFANKPAAAVLFINEL---
IPD101Fb  (138)  ---AVEAAAALAGVEV-ATLAVVCSIATLVVFTLILPILF-VMEKPANCILLINEVG--
IPD101Ga  (144)  ------LGLAEAIFTAVVSLGTTVVGAIVDIIVLCIIPIFY-FMAKPAACFMTINEL---
IPD101Gb  (149)  ----EVLLPAAFGAVEFCTPAVLVGAVATAIVLIIIPLIY-FANKPAACILLVINELR--
IPD101Gc  (122)  ---TEVIKSAIEIALDVAENLGEIGEIIAAILVIIPIIY-FMLKPAFTTVLIINDS---
IPD101Gd  (134)  ----MVATLAVAAGVEAIVACLVTLIAVALIAIIIPLIY-FMLKPACCFVVVLNET---
IPD101Ge  (134)  ----MVASVAVAAGVTAVIVACLVTLIAVAIAVIIPLIY-FMLKPACCFVLVLNET---
IPD101Gf  (141)  -VGYLTFSIVLAGVLS-AGAAIVVAIAAFIVIMLIFPFIY-FMNKPAVCIVALINFIPGL
```

Figure 1(c)

```
              241                                                          300
IPD101Aa (193) ---------DEPLVFETDHNVHGKPM----LMTIPIPKCVVIPGVGTYATAGFIATEKRE
IPD101Ab (193) ---------DEPLVFETDHNVHGKPM----LMTIPIPKCVVIPGVGTYATAGFIATEKRE
IPD101Ac (193) ---------DEPLVFETDHNVHGKPM----LMTIPIPKCVVIPGVGTYATAGFIATEKRE
IPD101Ba (193) ---------DKPLTFVSDHNVHGKPM----LMTIPIPEAVVIPEVGTYPSGLIATEKRE
IPD101Ca (193) ---------DKPLTFVSDHNVHGKPM----LMTIPIPECVEIPGVAKYPVAGLIATEKRD
IPD101Cb (193) ---------DKPLTFVSDHNVHGKPM----LMTIPIPECIEIPEVAKYPVAGLIATEKRD
IPD101Cc (193) ---------DKPLTFVSDHNVHGKPM----LMTIPIPECVEIPGVAKYPVAGLIATEKRD
IPD101Cf (193) ---------DKPLVFVDDHNIHGKPM----LMTIPIPECVEIPGAAKYPIAGLIAAEKRD
IPD101Cd (193) ---------DKPLVFEQDHNVRGVPA----LMIETIPEGIEIRGIAKYPVGSLIASQKAD
IPD101Ce (193) ---------DKPLVFSGDYNIHGKPM----LMTIPIPNCVEIPGVGKYPVAGFIASEKET
IPD101Ea (193) ---------DKPIVFANDFNVHGKPT----YLIETINNAVIFPDR-KFVTAGFICSQKLD
IPD101Eb (193) ---------DKPIVFANDFNVHGKPT----YLIETINNAVIFPDR-KFVTAGFICSQKLD
IPD101Ee (206) ---------DKPLSFYGDYNVHGNGT----LYISTIQNGLCIPNIGRYAVGGFFAIEKAS
IPD101Fa (230) ---------DKPVKFLSDHNIHGEPR----LRILTIRNGYVVRTIGMYPSAGFFAIQKHE
IPD101Fb (191) --------DNLDSLEFQEDYNVHGKPA----LITRSILGPLDFGSGQVRYNAGFIAAEKRD
IPD101Ga (195) ---------ETNIVIDEFKVIHGKVN------VKTREIAASIKIIHTTRSGGIWSIQKKD
IPD101Gb (202) -----------QDLIFKDDKCVHGKIMET--TK--HIPKITETNTLGTIYSAGFFASQKKD
IPD101Gc (175) ---------DENYKFGKHFNIHGKTT-----SYITSITSTFEKDGQTFSNAGFFTSSKKD
IPD101Gd (186) ----------NNQINWVDDYNVHGKPIGHTPFISAAIDIPQPIPGAGRYVYCGLVQIDKKD
IPD101Ge (186) ----------NNQITWKDDYNVHGKPIGHTPHISAAIDIPEPIPGAGKYVYAGLVQIDKRD
IPD101Gf (198) DFDSDLTGLKNTITFSDNYNIHGKPT----LIIKEIPGALFTDQG-PYAYIGLFAISKED 301                                                          360
IPD101Aa (240) NALVGIQYGFIMRY----------KDIKLSIGVECPLIALYIDNNCYCAIDESAVTVAE
IPD101Ab (240) NALVGIQYGFIMRY----------KDIKLSIGVECPLIALYIDNNCYCAINESAVTVAE
IPD101Ac (240) NALVGIQYGFIMRY----------KDIKLSIGVECPLIALYIDNNCYCAIDESAVTVAE
IPD101Ba (240) NALVGIQYGFIMQYG---------TDIKLSIGVECPLIGIYIDNNCYCAIDESASTVAE
IPD101Ca (240) SALVGIQYGFIMQYGS--------TGINFSIGVECPLISLSIDNNCYCAIDESAKTVAE
IPD101Cb (240) SALVGIQYGFIMKYGN--------TDINFSIGVECPLISLSIDNNCYCAIDENAKTVAE
IPD101Cc (240) SALVGIQYGFIMKYGN--------TGINFSIGVECPLISLSIDNNCYCAIDESAKTVAE
IPD101Cf (240) KALIGIQYGFIMQYGS--------TSIKFSIGVECPLISLSIDNNCYCAIDESAKTVAE
IPD101Cd (240) KSLYGIQYGFIMRYGS--------TDIKLSIGVECPLTSLYHDNNCYCAIGESAKKAAE
IPD101Ce (240) AALVGIQYGFIMQYGD--------TSIKFSIGVECPLSSLYIDNNCYCAIDESAEAVAN
IPD101Ea (239) SALYGIQYGFIMKYGH--------TDIQFIGVECPLSSLYIDNNCFCAFIKNAQEAAE
IPD101Eb (239) SALYGIQYGFIMKYGH--------TDIQFIGVECPLSSLYIDNNCFCAFIKNAQEAAE
IPD101Ee (253) GALIGIQYGFIMTLG---------GTIKLSIGVECPLISLYIDNNCYCAINEDAKNVAE
IPD101Fa (277) DALIGIQYGFILKYGD--------TDIKFIFAVECPLAEKR--NSCYGSFNEDPESAAQ
IPD101Fb (240) NALVGCQYGFILTENNGG--AHNSLKGQRFIPGVDCPLIGIDGWNNCYCSFIDNAKQAAE
IPD101Ga (240) AALIGIQYGVVLRQIKG--ISGVEPDNIKFAVGVECPLASGN--NSCAVGINKIASQIAE
IPD101Gb (248) AALIGIQYGLLIVQAD--------IDKITFNFCVNCPLADGK--NNCAVGCNQISQSISE
IPD101Gc (221) GALYGIQSGFILTG----------QETLAFGAECPLNGSN---NCYCEFIDKSAEQISK
IPD101Gd (237) AALVGIQYGFIYSGNS--------GAYKANFGVECPLTSLYVDNNCFCEIGSSSEDAAN
IPD101Ge (237) AALFGIQYGFIYTGDV--------GKYNVNFGAECPLSSIYVDNNCYCEIGSISENSAR
IPD101Gf (253) KALIGPQYGFIIELPYSKDLHKDEVKSMTAAFGAGCFLALGK-NNCYCDFIISAEKAAK
```

Figure 1(d)

```
            361                                              408
IPD101Aa (289) M..KKNKQYWEHNKNG--.GLSIRCNSGSCSIAYYVARAFKK------
IPD101Ab (289) M..KKNQQYWEHHKNG--.GLSIRCNSGSCSIAYYVARAFKK------
IPD101Ac (289) M..KKNQQYWEHHKNG--.GLSIRCNSGSCSIAYYVARAFKK------
IPD101Ba (291) M..RQNKQFWEDEKNG--.KLSIRCNSGSCSIAYYVARAYRG------
IPD101Ca (291) R.SNKNKQFWEAEKDG--.KLSIRCNSGSCSIAYYVARAYRA------
IPD101Cb (291) R.SDKNKQFWEAEKDG--.KLSIRCNSGSCSIAYYVARAFKA------
IPD101Cc (291) R.SDKNKQFWEAEKDG--.KLSIRCNSGSCSIAYYVARAFKA------
IPD101Cf (291) R.SNNNKQFWEVEKDG--.KLSIRCNSGSCSIAYYVARAYKA------
IPD101Cd (291) T..KKNKQFWETEKDG--.KLSIRCNSGSCSIAYYVARAYKA------
IPD101Ce (291) M..NKNVQFWEAEKDG--.KLSIRCNSGSCSIAYYVARAYRS------
IPD101Ea (290) L.AKNNKQFWETEKDG--.KLSIRCNSKSCSLAYYVARAYHV------
IPD101Eb (290) L.AQNNKQFWETEKDG--.KLSIRCNSKSCSLAYYVARAYHV------
IPD101Ee (303) L.SEKNQQYWESKQNG--.GLSIRCHSCSCSVAYYIARAYQV------
IPD101Fa (326) M.DKKSSQHWEAEQNG--.KLSITCNSNEGSIAYYVARAYKE------
IPD101Fb (298) N.DKHDAISYTAEKNG--.KLSIKCNSQKGSIAYYVARVYK-------
IPD101Ga (296) EVDDHRRQ-SVSVSDG-KYGIEMHCNSGSCSIAYYICRIYKC------
IPD101Gb (298) DAVLYQKQEYKHVQDG--YEID.KCNSAKGSVAYYIARVRYARQ----
IPD101Gc (267) L.EKKKDLYHEVSKGG--.GLNIRCNSKSGGLAWFICRIYNT------
IPD101Gd (288) Q.DSKNVLSYTASSVNPKLDVSINCNSGSGYVAYYIARVKDGSLN---
IPD101Ge (288) Q..KKNALTYSATSTTPKLDTSIKCNSASGYVAYYIARVEDGSLS---
IPD101Gf (311) NANKHSNQTWYAENDG--VSLSIKCNSGSCSIAYYIARVYKTKHSINN
```

INSECTICIDAL PROTEINS AND METHODS FOR THEIR USE

CROSS REFERENCE TO RELATED APPLICATIONS

This Application is a National Stage application of International Patent Application number PCT/US2017/067107, which claims the benefit of priority to U.S. Provisional Application No. 62/438,179 filed on Dec. 22, 2016, the disclosures of each of which are incorporated herein by reference in their entireties.

REFERENCE TO SEQUENCE LISTING SUBMITTED ELECTRONICALLY

The official copy of the sequence listing is submitted electronically via EFS-Web as an ASCII formatted sequence listing with a file named "6729WOPCT_Sequence_Listing" created on Nov. 30, 2017, and having a size of 107 kilobytes and is filed concurrently with the specification. The sequence listing contained in this ASCII formatted document is part of the specification and is herein incorporated by reference in its entirety.

FIELD

This disclosure relates to the field of molecular biology. Provided are novel genes that encode pesticidal proteins. These pesticidal proteins and the nucleic acid sequences that encode them are useful in preparing pesticidal formulations and in the production of transgenic pest-resistant plants.

BACKGROUND

Biological control of insect pests of agricultural significance using a microbial agent, such as fungi, bacteria or another species of insect affords an environmentally friendly and commercially attractive alternative to synthetic chemical pesticides. Generally speaking, the use of biopesticides presents a lower risk of pollution and environmental hazards and biopesticides provide greater target specificity than is characteristic of traditional broad-spectrum chemical insecticides. In addition, biopesticides often cost less to produce and thus improve economic yield for a wide variety of crops.

Certain species of microorganisms of the genus *Bacillus* are known to possess pesticidal activity against a range of insect pests including Lepidoptera, Diptera, Coleoptera, Hemiptera and others. *Bacillus thuringiensis* (Bt) and *Bacillus popilliae* are among the most successful biocontrol agents discovered to date. Insect pathogenicity has also been attributed to strains of *B. larvae*, *B. lentimorbus*, *B. sphaericus* and *B. cereus*. Microbial insecticides, particularly those obtained from *Bacillus* strains, have played an important role in agriculture as alternatives to chemical pest control.

Crop plants have been developed with enhanced insect resistance by genetically engineering crop plants to produce pesticidal proteins from *Bacillus*. For example, corn and cotton plants have been genetically engineered to produce pesticidal proteins isolated from strains of *Bacillus thuringiensis*. These genetically engineered crops are now widely used in agriculture and have provided the farmer with an environmentally friendly alternative to traditional insect-control methods. While they have proven to be very successful commercially, these genetically engineered, insect-resistant crop plants may provide resistance to only a narrow range of the economically important insect pests. In some cases, insects can develop resistance to different insecticidal compounds, which raises the need to identify alternative biological control agents for pest control.

Accordingly, there remains a need for new pesticidal proteins with different ranges of insecticidal activity against insect pests, e.g., insecticidal proteins which are active against a variety of insects in the order Lepidoptera and the order Coleoptera, including but not limited to insect pests that have developed resistance to existing insecticides.

SUMMARY

In one aspect compositions and methods for conferring pesticidal activity to bacteria, plants, plant cells, tissues and seeds are provided. Compositions include nucleic acid molecules encoding sequences for pesticidal and insecticidal polypeptides, vectors comprising those nucleic acid molecules, and host cells comprising the vectors. Compositions also include the pesticidal polypeptide sequences and antibodies to those polypeptides. Compositions also comprise transformed bacteria, plants, plant cells, tissues and seeds.

In another aspect isolated or recombinant nucleic acid molecules are provided encoding IPD101 polypeptides including amino acid substitutions, deletions, insertions, and fragments thereof. Provided are isolated or recombinant nucleic acid molecules capable of encoding IPD101 polypeptides of SEQ ID NOS: 2, 4, 6, 8, 10, 12, 14, 16, 18, 20, 22, 24, 25, 26, 28, 29, 30, 32, 46, 48, 50, 52, 54, 56, 58, and 60, as well as amino acid substitutions, deletions, insertions, fragments thereof, and combinations thereof. Nucleic acid sequences that are complementary to a nucleic acid sequence of the embodiments or that hybridize to a sequence of the embodiments are also encompassed. The nucleic acid sequences can be used in DNA constructs or expression cassettes for transformation and expression in organisms, including microorganisms and plants. The nucleotide or amino acid sequences may be synthetic sequences that have been designed for expression in an organism including, but not limited to, a microorganism or a plant.

In another aspect IPD101 polypeptides are encompassed. Also provided are isolated or recombinant IPD101 polypeptides of SEQ ID NO: 2, 4, 6, 8, 10, 12, 14, 16, 18, 20, 22, 24, 25, 26, 28, 29, 30, 32, 46, 48, 50, 52, 54, 56, 58, and 60, as well as amino acid substitutions, deletions, insertions, fragments thereof and combinations thereof.

In another aspect methods are provided for producing the polypeptides and for using those polypeptides for controlling or killing a Lepidopteran, Coleopteran, nematode, fungi, and/or Dipteran pests. The transgenic plants of the embodiments express one or more of the pesticidal sequences disclosed herein. In various embodiments, the transgenic plant further comprises one or more additional genes for insect resistance, for example, one or more additional genes for controlling Coleopteran, Lepidopteran, Hemipteran or nematode pests. It will be understood by one of skill in the art that the transgenic plant may comprise any gene imparting an agronomic trait of interest.

In another aspect methods for detecting the nucleic acids and polypeptides of the embodiments in a sample are also included. A kit for detecting the presence of an IPD101 polypeptide or detecting the presence of a polynucleotide encoding an IPD101 polypeptide in a sample is provided. The kit may be provided along with all reagents and control samples necessary for carrying out a method for detecting the intended agent, as well as instructions for use.

In another aspect the compositions and methods of the embodiments are useful for the production of organisms with enhanced pest resistance or tolerance. These organisms and compositions comprising the organisms are desirable for agricultural purposes. The compositions of the embodiments are also useful for generating altered or improved proteins that have pesticidal activity or for detecting the presence of IPD101 polypeptides.

BRIEF DESCRIPTION OF THE FIGURES

FIGS. 1(a)-(d) shows an amino acid sequence alignment, using the ALIGNX® module of the Vector NTI® suite, of the IPD101Aa polypeptide (SEQ ID NO: 2), the IPD101Ab polypeptide (SEQ ID NO: 4), the IPD101Ac polypeptide (SEQ ID NO: 6), the IPD101Ba polypeptide (SEQ ID NO: 8), the IPD101Ca polypeptide (SEQ ID NO: 10), the IPD101Cb polypeptide (SEQ ID NO: 12), the IPD101Cc polypeptide (SEQ ID NO: 14), the IPD101Cd polypeptide (SEQ ID NO: 16), the IPD101Ce polypeptide (SEQ ID NO: 18), the IPD101Cf polypeptide (SEQ ID NO: 20), the IPD101Ea polypeptide (SEQ ID NO: 22), the IPD101Eb polypeptide (SEQ ID NO: 24), the IPD101Ee polypeptide (SEQ ID NO: 25), the IPD101Fa polypeptide (SEQ ID NO: 26), the IPD101Fb polypeptide (SEQ ID NO: 28), the IPD101Ga polypeptide (SEQ ID NO: 29), the IPD101Gb polypeptide (SEQ ID NO: 30), the IPD101Gc polypeptide (SEQ ID NO: 32), the IPD101Gd polypeptide (SEQ ID NO: 56), the IPD101Ge polypeptide (SEQ ID NO: 58), and the IPD101Gf polypeptide (SEQ ID NO: 60). The amino acid sequence diversity between the amino acid sequences is highlighted. Conservative amino acid differences are indicated by (A) shading.

DETAILED DESCRIPTION

Figure 2:
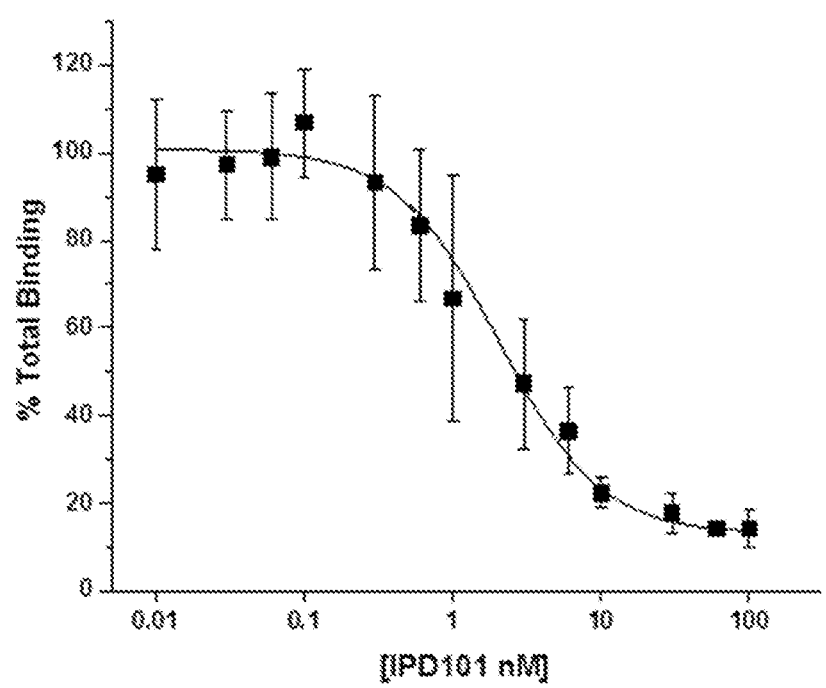
FIG. 2: Homologous competition of Alexa-labeled IPD101Aa (1.5 nM) binding to WCRW BBMVs reveals specific binding with high apparent affinity (EC50=2 nM).

It is to be understood that this disclosure is not limited to the particular methodology, protocols, cell lines, genera, and reagents described, as such may vary. It is also to be understood that the terminology used herein is for the purpose of describing particular embodiments only, and is not intended to limit the scope of the present disclosure.

As used herein the singular forms "a", "and", and "the" include plural referents unless the context clearly dictates otherwise. Thus, for example, reference to "a cell" includes a plurality of such cells and reference to "the protein" includes reference to one or more proteins and equivalents thereof, and so forth. All technical and scientific terms used herein have the same meaning as commonly understood to one of ordinary skill in the art to which this disclosure belongs unless clearly indicated otherwise.

The present disclosure is drawn to compositions and methods for controlling pests. The methods involve transforming organisms with nucleic acid sequences encoding IPD101 polypeptides. In particular, the nucleic acid sequences of the embodiments are useful for preparing plants and microorganisms that possess pesticidal activity. Thus, transformed bacteria, plants, plant cells, plant tissues and seeds are provided. The compositions include pesticidal nucleic acids and proteins of bacterial species. The nucleic acid sequences find use in the construction of expression vectors for subsequent transformation into organisms of interest, as probes for the isolation of other homologous (or partially homologous) genes, and for the generation of altered IPD101 polypeptides by methods known in the art, such as site directed mutagenesis, domain swapping or DNA shuffling. The IPD101 polypeptides find use in controlling or killing Lepidopteran, Coleopteran, Dipteran, fungal, Hemipteran and nematode pest populations and for producing compositions with pesticidal activity. Insect pests of interest include, but are not limited to, Lepidoptera species including but not limited to: Corn Earworm, (CEW) (*Helicoverpa zea*), European Corn Borer (ECB) (*Ostrinia nubialis*), diamond-back moth, e.g., *Helicoverpa zea* Boddie; soybean looper, e.g., *Pseudoplusia includens* Walker; and velvet bean caterpillar e.g., *Anticarsia gemmatalis* Hübner and Coleoptera species including but not limited to Western corn rootworm (*Diabrotica virgifera*)—WCRW, Southern corn rootworm (*Diabrotica undecimpunctata howardi*)—SCRW, and Northern corn rootworm (*Diabrotica barberi*)—NCRW.

By "pesticidal toxin" or "pesticidal protein" is used herein to refer to a toxin that has toxic activity against one or more pests, including, but not limited to, members of the Lepidoptera, Diptera, Hemiptera and Coleoptera orders or the Nematoda phylum or a protein that has homology to such a protein. Pesticidal proteins have been isolated from organisms including, for example, *Bacillus* sp., *Pseudomonas* sp., *Photorhabdus* sp., *Xenorhabdus* sp., *Clostridium bifermentans* and *Paenibacillus popilliae*.

In some embodiments the IPD101 polypeptide includes an amino acid sequence deduced from the full-length nucleic acid sequence disclosed herein and amino acid sequences that are shorter than the full-length sequences, either due to the use of an alternate downstream start site or due to processing that produces a shorter protein having pesticidal activity. Processing may occur in the organism the protein is expressed in or in the pest after ingestion of the protein.

Thus, provided herein are novel isolated or recombinant nucleic acid sequences that confer pesticidal activity. Also provided are the amino acid sequences of IPD101 polypeptides. The polypeptides resulting from translation of these IPD101 genes allows cells to control or kill pests that ingest it.

IPD101 Proteins and Variants and Fragments Thereof

IPD101 polypeptides are encompassed by the disclosure. "IPD101 polypeptide", and "IPD101 protein" as used herein interchangeably refers to a polypeptide(s) having insecticidal activity including but not limited to insecticidal activity against one or more insect pests of the Lepidoptera and/or Coleoptera orders, and is sufficiently homologous to the IPD101Aa polypeptide of SEQ ID NO: 2. A variety of IPD101 polypeptides are contemplated. Sources of IPD101 polypeptides or related proteins include bacterial species selected from but not limited to *Lysinibacillus* species. Alignment of the amino acid sequences of IPD101 polypeptide homologs (for example, see FIG. 1), allows for the identification of residues that are highly conserved amongst the natural homologs of this family.

"Sufficiently homologous" is used herein to refer to an amino acid sequence that has at least about 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence homology compared to a reference sequence using one of the alignment programs described herein using standard parameters. In some embodiments the sequence homology is against the full length sequence of an IPD101 polypeptide. In some embodiments the IPD101 polypeptide has at least about 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to any one of SEQ ID NOS: 2, 4, 6, 8, 10, 12, 14, 16, 18, 20, 22, 24, 25, 26, 28, 29, 30, 32, 46, 48, 50, 52, 54, 56, 58, and 60. The term "about" when used herein in context with percent sequence identity means+/−0.5%. One of skill in the art will recognize that these values can be appropriately adjusted to determine corresponding homology of proteins taking into account amino acid similarity and the like. In some embodiments the sequence identity is calculated using ClustalW algorithm in the ALIGNX® module of the Vector NTI® Program Suite (Invitrogen Corporation, Carlsbad, Calif.) with all default parameters. In some embodiments the sequence identity is across the entire length of polypeptide calculated using ClustalW algorithm in the ALIGNX® module of the Vector NTI® Program Suite (Invitrogen Corporation, Carlsbad, Calif.) with all default parameters.

As used herein, the terms "protein," "peptide molecule," or "polypeptide" includes any molecule that comprises five or more amino acids. It is well known in the art that protein, peptide or polypeptide molecules may undergo modification, including post-translational modifications, such as, but not limited to, disulfide bond formation, glycosylation, phosphorylation or oligomerization. Thus, as used herein, the terms "protein," "peptide molecule" or "polypeptide" includes any protein that is modified by any biological or non-biological process. The terms "amino acid" and "amino acids" refer to all naturally occurring L-amino acids.

A "recombinant protein" is used herein to refer to a protein that is no longer in its natural environment, for example in vitro or in a recombinant bacterial or plant host cell. An IPD101 polypeptide that is substantially free of cellular material includes preparations of protein having less than about 30%, 20%, 10% or 5% (by dry weight) of non-pesticidal protein (also referred to herein as a "contaminating protein").

"Fragments" or "biologically active portions" include polypeptide fragments comprising amino acid sequences sufficiently identical to an IPD101 polypeptide and that exhibit insecticidal activity. "Fragments" or "biologically active portions" of IPD101 polypeptides includes fragments comprising amino acid sequences sufficiently identical to the amino acid sequence set forth in any one of SEQ ID NOS: 2, 4, 6, 8, 10, 12, 14, 16, 18, 20, 22, 24, 25, 26, 28, 29, 30, 32, 46, 48, 50, 52, 54, 56, 58, and 60 wherein the IPD101 polypeptide has insecticidal activity. Such biologically active portions can be prepared by recombinant techniques and evaluated for insecticidal activity. In some embodiments, the IPD101 polypeptide fragment is an N-terminal and/or a C-terminal truncation of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 or more amino acids from the N-terminus and/or C-terminus relative to any one of SEQ ID NOS: 2, 4, 6, 8, 10, 12, 14, 16, 18, 20, 22, 24, 25, 26, 28, 29, 30, 32, 46, 48, 50, 52, 54, 56, 58, and 60, e.g., by proteolysis, by insertion of a start codon, by deletion of the codons encoding the deleted amino acids and concomitant insertion of a start codon, and/or insertion of a stop codon. In some embodiments, the IPD101 polypeptide fragment is an N-terminal truncation of at least 1, 2, 3, 4, 5, 6, 7, 8, 9, 10, 11, 12, 13, 14, 15, 16, 17, 18, 19, 20, 21, 22, 23, 24 amino acids from the N-terminus of any one of SEQ ID NOS: 2, 4, 6, 8, 10, 12, 14, 16, 18, 20, 22, 24, 25, 26, 28, 29, 30, 32, 46, 48, 50, 52, 54, 56, 58, and 60. In some embodiments, the IPD101 polypeptide fragment is an N-terminal and/or a C-terminal truncation of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 or more amino acids from the N-terminus and/or C-terminus relative to any one of SEQ ID NOS: 2, 4, 6, 8, 10, 12, 14, 16, 18, 20, 22, 24, 25, 26, 28, 29, 30, 32, 46, 48, 50, 52, 54, 56, 58, and 60.

"Variants" as used herein refers to proteins or polypeptides having an amino acid sequence that is at least about 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or greater identical to the parental amino acid sequence.

In some embodiments an IPD101 polypeptide comprises an amino acid sequence having at least about 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater identity to the amino acid sequence of any one of SEQ ID NOS: 2, 4, 6, 8, 10, 12, 14, 16, 18, 20, 22, 24, 25, 26, 28, 29, 30, 32, 46, 48, 50, 52, 54, 56, 58, and 60, wherein the IPD101 polypeptide has insecticidal activity.

In some embodiments an IPD101 polypeptide comprises an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99% or greater identity across the entire length of the amino acid sequence of any one of SEQ ID NOS: 2, 4, 6, 8, 10, 12, 14, 16, 18, 20, 22, 24, 25, 26, 28, 29, 30, 32, 46, 48, 50, 52, 54, 56, 58, and 60.

In some embodiments the sequence identity is across the entire length of the polypeptide calculated using ClustalW algorithm in the ALIGNX® module of the Vector NTI® Program Suite (Invitrogen Corporation, Carlsbad, Calif.) with all default parameters.

In some embodiments an IPD101 polypeptide comprises an amino acid sequence of any one or more of SEQ ID NOS: 2, 4, 6, 8, 10, 12, 14, 16, 18, 20, 22, 24, 25, 26, 28, 29, 30, 32, 46, 48, 50, 52, 54, 56, 58, and 60 having 1, 2, 3, 4, 5, 6, 7, 8, 9, 10 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95 or more amino acid substitutions compared to the native amino acid at the corresponding position of any one or more of the respective SEQ ID NOS: 2, 4, 6, 8, 10, 12, 14, 16, 18, 20, 22, 24, 25, 26, 28, 29, 30, 32, 46, 48, 50, 52, 54, 56, 58, and 60.

Methods for such manipulations are generally known in the art. For example, amino acid sequence variants of an IPD101 polypeptide can be prepared by mutations in the DNA. This may also be accomplished by one of several forms of mutagenesis and/or in directed evolution. In some aspects, the changes encoded in the amino acid sequence will not substantially affect the function of the protein. Such variants will possess the desired pesticidal activity. However, it is understood that the ability of an IPD101 polypeptide to confer pesticidal activity may be improved by the use of such techniques upon the compositions of this disclosure.

For example, conservative amino acid substitutions may be made at one or more predicted nonessential amino acid residues. A "nonessential" amino acid residue is a residue that can be altered from the wild-type sequence of an IPD101 polypeptide without altering the biological activity. A "conservative amino acid substitution" is one in which the amino acid residue is replaced with an amino acid residue having a similar side chain. Families of amino acid residues having similar side chains have been defined in the art. These families include: amino acids with basic side chains (e.g., lysine, arginine, histidine); acidic side chains (e.g., aspartic acid, glutamic acid); polar, negatively charged residues and their amides (e.g., aspartic acid, asparagine, glutamic, acid, glutamine; uncharged polar side chains (e.g., glycine, asparagine, glutamine, serine, threonine, tyrosine, cysteine); small aliphatic, nonpolar or slightly polar residues (e.g., Alanine, serine, threonine, proline, glycine); nonpolar side chains (e.g., alanine, valine, leucine, isoleucine, proline, phenylalanine, methionine, tryptophan); large aliphatic, nonpolar residues (e.g., methionine, leucine, isoleucine, valine, cystine); beta-branched side chains (e.g., threonine, valine, isoleucine); aromatic side chains (e.g., tyrosine, phenylalanine, tryptophan, histidine); large aromatic side chains (e.g., tyrosine, phenylalanine, tryptophan).

Amino acid substitutions may be made in nonconserved regions that retain function. In general, such substitutions would not be made for conserved amino acid residues or for amino acid residues residing within a conserved motif, where such residues are essential for protein activity. Examples of residues that are conserved and that may be essential for protein activity include, for example, residues that are identical between all proteins contained in an alignment of similar or related toxins to the sequences of the embodiments (e.g., residues that are identical in an alignment of homologous proteins). Examples of residues that are conserved but that may allow conservative amino acid substitutions and still retain activity include, for example, residues that have only conservative substitutions between all proteins contained in an alignment of similar or related toxins to the sequences of the embodiments (e.g., residues that have only conservative substitutions between all proteins contained in the alignment homologous proteins). However, one of skill in the art would understand that functional variants may have minor conserved or nonconserved alterations in the conserved residues. Guidance as to appropriate amino acid substitutions that do not affect biological activity of the protein of interest may be found in the model of Dayhoff, et al., (1978) *Atlas of Protein Sequence and Structure* (Natl. Biomed. Res. Found., Washington, D.C.).

In making such changes, the hydropathic index of amino acids may be considered. The importance of the hydropathic amino acid index in conferring interactive biologic function on a protein is generally understood in the art (Kyte and Doolittle, (1982) *J Mol Biol.* 157(1):105-32). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It is known in the art that certain amino acids may be substituted by other amino acids having a similar hydropathic index or score and still result in a protein with similar biological activity, i.e., still obtain a biological functionally equivalent protein. Each amino acid has been assigned a hydropathic index on the basis of its hydrophobicity and charge characteristics (Kyte and Doolittle, ibid). These are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9) and arginine (−4.5). In making such changes, the substitution of amino acids whose hydropathic indices are within +2 is preferred, those which are within +1 are particularly preferred, and those within +0.5 are even more particularly preferred.

It is also understood in the art that the substitution of like amino acids can be made effectively on the basis of hydrophilicity. U.S. Pat. No. 4,554,101, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0.+0.1); glutamate (+3.0.+0.1); serine (+0.3); asparagine (+0.2); glutamine (+0.2); glycine (0); threonine (−0.4); proline (−0.5.+0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

Alternatively, alterations may be made to the protein sequence of many proteins at the amino or carboxy terminus without substantially affecting activity. This can include insertions, deletions or alterations introduced by modern molecular methods, such as PCR, including PCR amplifications that alter or extend the protein coding sequence by virtue of inclusion of amino acid encoding sequences in the oligonucleotides utilized in the PCR amplification. Alternatively, the protein sequences added can include entire protein-coding sequences, such as those used commonly in the art to generate protein fusions. Such fusion proteins are often used to (1) increase expression of a protein of interest (2) introduce a binding domain, enzymatic activity or epitope to facilitate either protein purification, protein detection or other experimental uses known in the art (3) target secretion or translation of a protein to a subcellular organelle, such as the periplasmic space of Gram-negative bacteria, mitochondria or chloroplasts of plants or the endoplasmic reticulum of eukaryotic cells, the latter of which often results in glycosylation of the protein.

Variant nucleotide and amino acid sequences of the disclosure also encompass sequences derived from mutagenic and recombinogenic procedures such as DNA shuffling. With such a procedure, one or more different IPD101 polypeptide coding regions can be used to create a new IPD101 polypeptide possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between a pesticidal gene and other known pesticidal genes to obtain a new gene coding for a protein with an improved property of interest, such as an increased insecticidal activity. Strategies for such DNA shuffling are known in the art. See, for example, Stemmer, (1994) *Proc. Natl. Acad. Sci. USA* 91:10747-10751; Stemmer, (1994) *Nature* 370:389-391; Crameri, et al., (1997) *Nature Biotech.* 15:436-438; Moore, et al., (1997) *J. Mol. Biol.* 272:336-347; Zhang, et al., (1997) *Proc. Natl. Acad. Sci. USA* 94:4504-4509; Crameri, et al., (1998) *Nature* 391:288-291; and U.S. Pat. Nos. 5,605,793 and 5,837,458.

Domain swapping or shuffling is another mechanism for generating altered IPD101 polypeptides. Domains may be swapped between IPD101 polypeptides resulting in hybrid or chimeric toxins with improved insecticidal activity or target spectrum. Methods for generating recombinant proteins and testing them for pesticidal activity are well known in the art (see, for example, Naimov, et al., (2001) *Appl. Environ. Microbiol.* 67:5328-5330; de Maagd, et al., (1996) *Appl. Environ. Microbiol.* 62:1537-1543; Ge, et al., (1991) *J. Biol. Chem.* 266:17954-17958; Schnepf, et al., (1990) *J. Biol. Chem.* 265:20923-21010; Rang, et al., 91999) *Appl. Environ. Microbiol.* 65:2918-2925).

Phylogenetic, Sequence Motif, and Structural Analyses of Insecticidal Protein Families.

A sequence and structure analysis method can be employed, which is composed of four components: phylogenetic tree construction, protein sequence motifs finding, secondary structure prediction, and alignment of protein sequences and secondary structures. Details about each component are illustrated below.

1) Phylogenetic Tree Construction

The phylogenetic analysis can be performed using the software MEGA5. Protein sequences can be subjected to ClustalW version 2 analysis (Larkin M. A et al (2007) *Bioinformatics* 23(21): 2947-2948) for multiple sequence alignment. The evolutionary history is then inferred by the Maximum Likelihood method based on the JTT matrix-based model. The tree with the highest log likelihood is obtained, exported in Newick format, and further processed to extract the sequence IDs in the same order as they appeared in the tree. A few clades representing sub-families can be manually identified for each insecticidal protein family.

2) Protein Sequence Motifs Finding

Protein sequences are re-ordered according to the phylogenetic tree built previously, and fed to the MOTIF analysis tool MEME (Multiple EM for MOTIF Elicitation) (Bailey T. L., and Elkan C., *Proceedings of the Second International Conference on Intelligent Systems for Molecular Biology*, pp. 28-36, AAAI Press, Menlo Park, Calif., 1994.) for identification of key sequence motifs. MEME is setup as follows: Minimum number of sites 2, Minimum motif width 5, and Maximum number of motifs 30. Sequence motifs unique to each sub-family were identified by visual observation. The distribution of MOTIFs across the entire gene family could be visualized in HTML webpage. The MOTIFs are numbered relative to the ranking of the E-value for each MOTIF.

3) Secondary Structure Prediction

PSIPRED, top ranked secondary structure prediction method (Jones D T. (1999) *J. Mol. Biol.* 292: 195-202), can be used for protein secondary structure prediction. The tool provides accurate structure prediction using two feed-forward neural networks based on the PSI-BLAST output. The PSI-BLAST database is created by removing low-complexity, transmembrane, and coiled-coil regions in Uniref100. The PSIPRED results contain the predicted secondary structures (Alpha helix: H, Beta strand: E, and Coil: C) and the corresponding confidence scores for each amino acid in a given protein sequence.

4) Alignment of Protein Sequences and Secondary Structures

A script can be developed to generate gapped secondary structure alignment according to the multiple protein sequence alignment from step 1 for all proteins. All aligned protein sequences and structures are concatenated into a single FASTA file, and then imported into MEGA for visualization and identification of conserved structures.

In some embodiments the IPD101 polypeptide has a modified physical property. As used herein, the term "physical property" refers to any parameter suitable for describing the physical-chemical characteristics of a protein. As used herein, "physical property of interest" and "property of interest" are used interchangeably to refer to physical properties of proteins that are being investigated and/or modified. Examples of physical properties include, but are not limited to, net surface charge and charge distribution on the protein surface, net hydrophobicity and hydrophobic residue distribution on the protein surface, surface charge density, surface hydrophobicity density, total count of surface ionizable groups, surface tension, protein size and its distribution in solution, melting temperature, heat capacity, and second virial coefficient. Examples of physical properties also include, IPD101 polypeptide having increased expression, increased solubility, decreased phytotoxicity, and digestibility of proteolytic fragments in an insect gut. Models for digestion by simulated gastric fluids are known to one skilled in the art (Fuchs, R. L. and J. D. Astwood. *Food Technology* 50: 83-88, 1996; Astwood, J. D., et al *Nature Biotechnology* 14: 1269-1273, 1996; Fu T J et al *J. Agric Food Chem.* 50: 7154-7160, 2002).

In some embodiments variants include polypeptides that differ in amino acid sequence due to mutagenesis. Variant proteins encompassed by the disclosure are biologically active, that is they continue to possess the desired biological activity (i.e. pesticidal activity) of the native protein. In some embodiment the variant will have at least about 10%, at least about 30%, at least about 50%, at least about 70%, at least about 80% or more of the insecticidal activity of the native protein. In some embodiments, the variants may have improved activity over the native protein.

Bacterial genes quite often possess multiple methionine initiation codons in proximity to the start of the open reading frame. Often, translation initiation at one or more of these start codons will lead to generation of a functional protein. These start codons can include ATG codons. However, bacteria such as *Bacillus* sp. also recognize the codon GTG as a start codon, and proteins that initiate translation at GTG codons contain a methionine at the first amino acid. On rare occasions, translation in bacterial systems can initiate at a TTG codon, though in this event the TTG encodes a methionine. Furthermore, it is not often determined a priori which of these codons are used naturally in the bacterium. Thus, it is understood that use of one of the alternate methionine codons may also lead to generation of pesticidal proteins. These pesticidal proteins are encompassed in the present disclosure and may be used in the methods of the present disclosure. It will be understood that, when expressed in plants, it will be necessary to alter the alternate start codon to ATG for proper translation.

In some embodiments an IPD101 polypeptide comprises the amino acid sequence of any one or more of SEQ ID NOS: 2, 4, 6, 8, 10, 12, 14, 16, 18, 20, 22, 24, 25, 26, 28, 29, 30, 32, 46, 48, 50, 52, 54, 56, 58, and 60.

In some embodiments, chimeric polypeptides are provided comprising regions of at least two different IPD101 polypeptides of the disclosure.

In some embodiments, chimeric polypeptides are provided comprising regions of at least two different IPD101 polypeptides selected from any one or more of SEQ ID NOS: 2, 4, 6, 8, 10, 12, 14, 16, 18, 20, 22, 24, 25, 26, 28, 29, 30, 32, 46, 48, 50, 52, 54, 56, 58, and 60.

In some embodiments, chimeric IPD101 polypeptide(s) are provided comprising an N-terminal Region of a first IPD101 polypeptide of the disclosure operably fused to a C-terminal Region of a second IPD101 polypeptide of the disclosure.

In other embodiments the IPD101 polypeptide may be expressed as a precursor protein with an intervening sequence that catalyzes multi-step, post translational protein splicing. Protein splicing involves the excision of an intervening sequence from a polypeptide with the concomitant joining of the flanking sequences to yield a new polypeptide (Chong, et al., (1996) *J. Biol. Chem.*, 271:22159-22168). This intervening sequence or protein splicing element, referred to as inteins, which catalyze their own excision through three coordinated reactions at the N-terminal and C-terminal splice junctions: an acyl rearrangement of the N-terminal cysteine or serine; a transesterfication reaction between the two termini to form a branched ester or thioester intermediate and peptide bond cleavage coupled to cyclization of the intein C-terminal asparagine to free the intein (Evans, et al., (2000) *J. Biol. Chem.*, 275:9091-9094). The elucidation of the mechanism of protein splicing has led to a number of intein-based applications (Comb, et al., U.S. Pat. No. 5,496,714; Comb, et al., U.S. Pat. No. 5,834,247; Camarero and Muir, (1999) *J. Amer. Chem. Soc.* 121:5597-5598; Chong, et al., (1997) *Gene* 192:271-281, Chong, et al., (1998) *Nucleic Acids Res.* 26:5109-5115; Chong, et al., (1998) *J. Biol. Chem.* 273:10567-10577; Cotton, et al., (1999) *J. Am. Chem. Soc.* 121:1100-1101; Evans, et al., (1999) *J. Biol. Chem.* 274:18359-18363; Evans, et al., (1999) *J. Biol. Chem.* 274:3923-3926; Evans, et al., (1998) *Protein Sci.* 7:2256-2264; Evans, et al., (2000) *J. Biol. Chem.* 275:9091-9094; Iwai and Pluckthun, (1999) *FEBS Lett.* 459:166-172; Mathys, et al., (1999) *Gene* 231:1-13; Mills, et al., (1998) *Proc. Natl. Acad. Sci. USA* 95:3543-3548; Muir, et al., (1998) *Proc. Natl. Acad. Sci. USA* 95:6705-6710; Otomo, et al., (1999) *Biochemistry* 38:16040-16044; Otomo, et al., (1999) *J. Biolmol. NMR* 14:105-114; Scott, et al., (1999) *Proc. Natl. Acad. Sci. USA* 96:13638-13643; Severinov and Muir, (1998) *J. Biol. Chem.* 273:16205-16209; Shingledecker, et al., (1998) *Gene* 207:187-195; Southworth, et al., (1998) *EMBO J.* 17:918-926; Southworth, et al., (1999) *Biotechniques* 27:110-120; Wood, et al., (1999) *Nat. Biotechnol.* 17:889-892; Wu, et al., (1998a) *Proc. Natl. Acad. Sci. USA* 95:9226-9231; Wu, et al., (1998b) *Biochim Biophys Acta* 1387:422-432; Xu, et al., (1999) *Proc. Natl. Acad. Sci. USA* 96:388-393; Yamazaki, et al., (1998) *J. Am. Chem. Soc.*, 120:5591-5592). For the application of inteins in plant transgenes, see, Yang, et al., (*Transgene Res* 15:583-593 (2006)) and Evans, et al., (*Annu. Rev. Plant Biol.* 56:375-392 (2005)).

In another embodiment the IPD101 polypeptide may be encoded by two separate genes where the intein of the precursor protein comes from the two genes, referred to as a split-intein, and the two portions of the precursor are joined by a peptide bond formation. This peptide bond formation is accomplished by intein-mediated trans-splicing. For this purpose, a first and a second expression cassette comprising the two separate genes further code for inteins capable of mediating protein trans-splicing. By trans-splicing, the proteins and polypeptides encoded by the first and second fragments may be linked by peptide bond formation. Trans-splicing inteins may be selected from the nucleolar and organellar genomes of different organisms including eukaryotes, archaebacteria and eubacteria. Inteins that may be used for are listed at neb.com/neb/inteins.html, which can be accessed on the world-wide web using the "www" prefix). The nucleotide sequence coding for an intein may be split into a 5' and a 3' part that code for the 5' and the 3' part of the intein, respectively. Sequence portions not necessary for intein splicing (e.g. homing endonuclease domain) may be deleted. The intein coding sequence is split such that the 5' and the 3' parts are capable of trans-splicing. For selecting a suitable splitting site of the intein coding sequence, the considerations published by Southworth, et al., (1998) *EMBO J.* 17:918-926 may be followed. In constructing the first and the second expression cassette, the 5' intein coding sequence is linked to the 3' end of the first fragment coding for the N-terminal part of the IPD101 polypeptide and the 3' intein coding sequence is linked to the 5' end of the second fragment coding for the C-terminal part of the IPD101 polypeptide.

In general, the trans-splicing partners can be designed using any split intein, including any naturally-occurring or artificially-split split intein. Several naturally-occurring split inteins are known, for example: the split intein of the DnaE gene of *Synechocystis* sp. PCC6803 (see, Wu, et al., (1998) *Proc Natl Acad Sci USA.* 95(16):9226-31 and Evans, et al., (2000) *J Biol Chem.* 275(13):9091-4 and of the DnaE gene from *Nostoc punctiforme* (see, Iwai, et al., (2006) *FEBS Lett.* 580(7):1853-8). Non-split inteins have been artificially split in the laboratory to create new split inteins, for example: the artificially split Ssp DnaB intein (see, Wu, et al., (1998) *Biochim Biophys Acta.* 1387:422-32) and split Sce VMA intein (see, Brenzel, et al., (2006) *Biochemistry.* 45(6):1571-8) and an artificially split fungal mini-intein (see, Elleuche, et al., (2007) *Biochem Biophys Res Commun.* 355(3):830-4). There are also intein databases available that catalogue known inteins (see for example the online-database available at: bioinformatics.weizmann.ac.il/~pietro/inteins/Inteinstable.html, which can be accessed on the world-wide web using the "www" prefix).

Naturally-occurring non-split inteins may have endonuclease or other enzymatic activities that can typically be removed when designing an artificially-split split intein. Such mini-inteins or minimized split inteins are well known in the art and are typically less than 200 amino acid residues long (see, Wu, et al., (1998) *Biochim Biophys Acta.* 1387:422-32). Suitable split inteins may have other purification enabling polypeptide elements added to their structure, provided that such elements do not inhibit the splicing of the split intein or are added in a manner that allows them to be removed prior to splicing. Protein splicing has been reported using proteins that comprise bacterial intein-like (BIL) domains (see, Amitai, et al., (2003) *Mol Microbiol.* 47:61-73) and hedgehog (Hog) auto-processing domains (the latter is combined with inteins when referred to as the Hog/intein superfamily or HINT family (see, Dassa, et al., (2004) *J Biol Chem.* 279:32001-7) and domains such as these may also be used to prepare artificially-split inteins. In particular, non-splicing members of such families may be modified by molecular biology methodologies to introduce or restore splicing activity in such related species. Recent studies demonstrate that splicing can be observed when a N-terminal split intein component is allowed to react with a C-terminal split intein component not found in nature to be its "partner"; for example, splicing has been observed utilizing partners that have as little as 30 to 50% homology with the "natural" splicing partner (see, Dassa, et al., (2007) *Biochemistry.* 46(1):322-30). Other such mixtures of disparate split intein partners have been shown to be unreactive one with another (see, Brenzel, et al., (2006) *Biochemistry.* 45(6):1571-8). However, it is within the ability of a person skilled in the relevant art to determine whether a particular pair of polypeptides is able to associate with each other to provide a functional intein, using routine methods and without the exercise of inventive skill.

In some embodiments the IPD101 polypeptide is a circular permuted variant. In certain embodiments the IPD101 polypeptide is a circular permuted variant of any one of the polypeptides of SEQ ID NOS: 2, 4, 6, 8, 10, 12, 14, 16, 18, 20, 22, 24, 25, 26, 28, 29, 30, 32, 46, 48, 50, 52, 54, 56, 58, and 60, or variant thereof having an amino acid substitution, deletion, addition or combinations thereof. The approach used in creating new sequences resembles that of naturally occurring pairs of proteins that are related by linear reorganization of their amino acid sequences (Cunningham, et al., (1979) *Proc. Natl. Acad. Sci. U.S.A.* 76:3218-3222; Teather and Erfle, (1990) *J. Bacteriol.* 172:3837-3841; Schimming, et al., (1992) *Eur. J. Biochem.* 204:13-19; Yamiuchi and Minamikawa, (1991) *FEBS Lett.* 260:127-130; MacGregor, et al., (1996) *FEBS Lett.* 378:263-266). This type of rearrangement to proteins was described by Goldenberg and Creighton (*J. Mol. Biol.* 165:407-413, 1983). In creating a circular permuted variant a new N-terminus is selected at an internal site (breakpoint) of the original sequence, the new sequence having the same order of amino acids as the original from the breakpoint until it reaches an amino acid that is at or near the original C-terminus. At this point the new sequence is joined, either directly or through an additional portion of sequence (linker), to an amino acid that is at or near the original N-terminus and the new sequence continues with the same sequence as the original until it reaches a point that is at or near the amino acid that was N-terminal to the breakpoint site of the original sequence, this residue forming the new C-terminus of the chain. The length of the amino acid sequence of the linker can be selected empirically or with guidance from structural information or by using a combination of the two approaches. When no structural information is available, a small series of linkers can be prepared for testing using a design whose length is varied in order to span a range from 0 to 50 Å and whose sequence is chosen in order to be consistent with surface exposure (hydrophilicity, Hopp and Woods, (1983) *Mol. Immunol.* 20:483-489; Kyte and Doolittle, (1982) *J. Mol. Biol.* 157:105-132; solvent exposed surface area, Lee and Richards, (1971) *J. Mol. Biol.* 55:379-400) and the ability to adopt the necessary conformation without deranging the configuration of the pesticidal polypeptide (conformationally flexible; Karplus and Schulz, (1985) *Naturwissenschaften* 72:212-213). Assuming an average of translation of 2.0 to 3.8 Å per residue, this would mean the length to test would be between 0 to 30 residues, with 0 to 15 residues being the preferred range. Exemplary of such an empirical series would be to construct linkers using a cassette sequence such as Gly-Gly-Gly-Ser repeated n times, where n is 1, 2, 3 or 4. Those skilled in the art will recognize that there are many such sequences that vary in length or composition that can serve as linkers with the primary consideration being that they be neither excessively long nor short (cf., Sandhu, (1992) *Critical Rev. Biotech.* 12:437-462); if they are too long, entropy effects will likely destabilize the three-dimensional fold, and may also make folding kinetically impractical, and if they are too short, they will likely destabilize the molecule because of torsional or steric strain. Those skilled in the analysis of protein structural information will recognize that using the distance between the chain ends, defined as the distance between the c-alpha carbons, can be used to define the length of the sequence to be used or at least to limit the number of possibilities that must be tested in an empirical selection of linkers. They will also recognize that it is sometimes the case that the positions of the ends of the polypeptide chain are ill-defined in structural models derived from x-ray diffraction or nuclear magnetic resonance spectroscopy data, and that when true, this situation will therefore need to be taken into account in order to properly estimate the length of the linker required. From those residues whose positions are well defined are selected two residues that are close in sequence to the chain ends, and the distance between their c-alpha carbons is used to calculate an approximate length for a linker between them. Using the calculated length as a guide, linkers with a range of number of residues (calculated using 2 to 3.8 Å per residue) are then selected. These linkers may be composed of the original sequence, shortened or lengthened as necessary, and when lengthened the additional residues may be chosen to be flexible and hydrophilic as described above; or optionally the original sequence may be substituted for using a series of linkers, one example being the Gly-Gly-Gly-Ser cassette approach mentioned above; or optionally a combination of the original sequence and new sequence having the appropriate total length may be used.

Sequences of pesticidal polypeptides capable of folding to biologically active states can be prepared by appropriate selection of the beginning (amino terminus) and ending (carboxyl terminus) positions from within the original polypeptide chain while using the linker sequence as described above Amino and carboxyl termini are selected from within a common stretch of sequence, referred to as a breakpoint region, using the guidelines described below. A novel amino acid sequence is thus generated by selecting amino and carboxyl termini from within the same breakpoint region. In many cases the selection of the new termini will be such that the original position of the carboxyl terminus immediately preceded that of the amino terminus. However, those skilled in the art will recognize that selections of termini anywhere within the region may function, and that these will effectively lead to either deletions or additions to the amino or carboxyl portions of the new sequence. It is a central tenet of molecular biology that the primary amino acid sequence of a protein dictates folding to the three-dimensional structure necessary for expression of its biological function. Methods are known to those skilled in the art to obtain and interpret three-dimensional structural information using x-ray diffraction of single protein Crystals or nuclear magnetic resonance spectroscopy of protein solutions. Examples of structural information that are relevant to the identification of breakpoint regions include the location and type of protein secondary structure (alpha and 3-10 helices, parallel and anti-parallel beta sheets, chain reversals and turns, and loops; Kabsch and Sander, (1983) *Biopolymers* 22:2577-2637); the degree of solvent exposure of amino acid residues, the extent and type of interactions of residues with one another (Chothia, (1984) *Ann. Rev. Biochem.* 53:537-572) and the static and dynamic distribution of conformations along the polypeptide chain (Alber and Mathews, (1987) *Methods Enzymol.* 154:511-533). In some cases additional information is known about solvent exposure of residues; one example is a site of post-translational attachment of carbohydrate which is necessarily on the surface of the protein. When experimental structural information is not available or is not feasible to obtain, methods are also available to analyze the primary amino acid sequence in order to make predictions of protein tertiary and secondary structure, solvent accessibility and the occurrence of turns and loops. Biochemical methods are also sometimes applicable for empirically determining surface exposure when direct structural methods are not feasible; for example, using the identification of sites of chain scission following limited proteolysis in order to infer surface exposure (Gentile and Salvatore, (1993) *Eur. J. Biochem.* 218:603-621). Thus using either the experimentally derived structural information or predictive methods (e.g., Srinivisan and Rose, (1995) *Proteins: Struct., Funct. & Genetics* 22:81-99) the parental amino acid sequence is inspected to classify regions according to whether or not they are integral to the maintenance of secondary and tertiary structure. The occurrence of sequences within regions that are known to be involved in periodic secondary structure (alpha and 3-10 helices, parallel and anti-parallel beta sheets) are regions that should be avoided. Similarly, regions of amino acid sequence that are observed or predicted to have a low degree of solvent exposure are more likely to be part of the so-called hydrophobic core of the protein and should also be avoided for selection of amino and carboxyl termini In contrast, those regions that are known or predicted to be in surface turns or loops, and especially those regions that are known not to be required for biological activity, are the preferred sites for location of the extremes of the polypeptide chain. Continuous stretches of amino acid sequence that are preferred based on the above criteria are referred to as a breakpoint region. Polynucleotides encoding circular permuted IPD101 polypeptides with new N-terminus/C-terminus which contain a linker region separating the original C-terminus and N-terminus can be made essentially following the method described in Mullins, et al., (1994) *J. Am. Chem. Soc.* 116:5529-5533. Multiple steps of polymerase chain reaction (PCR) amplifications are used to rearrange the DNA sequence encoding the primary amino acid sequence of the protein. Polynucleotides encoding circular permuted IPD101 polypeptides with new N-terminus/C-terminus which contain a linker region separating the original C-terminus and N-terminus can be made based on the tandem-duplication method described in Horlick, et al., (1992) *Protein Eng.* 5:427-431. Polymerase chain reaction (PCR) amplification of the new N-terminus/C-terminus genes is performed using a tandemly duplicated template DNA.

In another embodiment fusion proteins are provided that include within its amino acid sequence an amino acid sequence comprising an IPD101 polypeptide of the disclosure. Methods for design and construction of fusion proteins (and polynucleotides encoding same) are known to those of skill in the art. Polynucleotides encoding an IPD101 polypeptide may be fused to signal sequences which will direct the localization of the IPD101 polypeptide to particular compartments of a prokaryotic or eukaryotic cell and/or direct the secretion of the IPD101 polypeptide of the embodiments from a prokaryotic or eukaryotic cell. For example, in *E. coli*, one may wish to direct the expression of the protein to the periplasmic space. Examples of signal sequences or proteins (or fragments thereof) to which the IPD101 polypeptide may be fused in order to direct the expression of the polypeptide to the periplasmic space of bacteria include, but are not limited to, the pelB signal sequence, the maltose binding protein (MBP) signal sequence, MBP, the ompA signal sequence, the signal sequence of the periplasmic *E. coli* heat-labile enterotoxin B-subunit and the signal sequence of alkaline phosphatase. Several vectors are commercially available for the construction of fusion proteins which will direct the localization of a protein, such as the pMAL series of vectors (particularly the pMAL-p series) available from New England Biolabs. In a specific embodiment, the IPD101 polypeptide may be fused to the pelB pectate lyase signal sequence to increase the efficiency of expression and purification of such polypeptides in Gram-negative bacteria (see, U.S. Pat. Nos. 5,576,195 and 5,846,818). Plant plastid transit peptide/polypeptide fusions are well known in the art. Apoplast transit peptides such as rice or barley alpha-amylase secretion signal are also well known in the art. The plastid transit peptide is generally fused N-terminal to the polypeptide to be targeted (e.g., the fusion partner). In one embodiment, the fusion protein consists essentially of the plastid transit peptide and the IPD101 polypeptide to be targeted. In another embodiment, the fusion protein comprises the plastid transit peptide and the polypeptide to be targeted. In such embodiments, the plastid transit peptide is preferably at the N-terminus of the fusion protein. However, additional amino acid residues may be N-terminal to the plastid transit peptide providing that the fusion protein is at least partially targeted to a plastid. In a specific embodiment, the plastid transit peptide is in the N-terminal half, N-terminal third or N-terminal quarter of the fusion protein. Most or all of the plastid transit peptide is generally cleaved from the fusion protein upon insertion into the plastid. The position of cleavage may vary slightly between plant species, at different plant developmental stages, as a result of specific intercellular conditions or the particular combination of transit peptide/fusion partner used. In one embodiment, the plastid transit peptide cleavage is homogenous such that the cleavage site is identical in a population of fusion proteins. In another embodiment, the plastid transit peptide is not homogenous, such that the cleavage site varies by 1-10 amino acids in a population of fusion proteins. The plastid transit peptide can be recombinantly fused to a second protein in one of several ways. For example, a restriction endonuclease recognition site can be introduced into the nucleotide sequence of the transit peptide at a position corresponding to its C-terminal end and the same or a compatible site can be engineered into the nucleotide sequence of the protein to be targeted at its N-terminal end. Care must be taken in designing these sites to ensure that the coding sequences of the transit peptide and the second protein are kept “in frame” to allow the synthesis of the desired fusion protein. In some cases, it may be preferable to remove the initiator methionine of the second protein when the new restriction site is introduced. The introduction of restriction endonuclease recognition sites on both parent molecules and their subsequent joining through recombinant DNA techniques may result in the addition of one or more extra amino acids between the transit peptide and the second protein. This generally does not affect targeting activity as long as the transit peptide cleavage site remains accessible and the function of the second protein is not altered by the addition of these extra amino acids at its N-terminus. Alternatively, one skilled in the art can create a precise cleavage site between the transit peptide and the second protein (with or without its initiator methionine) using gene synthesis (Stemmer, et al., (1995) *Gene* 164:49-53) or similar methods. In addition, the transit peptide fusion can intentionally include amino acids downstream of the cleavage site. The amino acids at the N-terminus of the mature protein can affect the ability of the transit peptide to target proteins to plastids and/or the efficiency of cleavage following protein import. This may be dependent on the protein to be targeted. See, e.g., Comai, et al., (1988) *J. Biol. Chem.* 263(29):15104-9. In some embodiments the IPD101 polypeptide is fused to a heterologous signal peptide or heterologous transit peptide.

In some embodiments fusion proteins are provide comprising an IPD101 polypeptide or chimeric IPD101 polypeptide of the disclosure represented by a formula selected from the group consisting of:

$R^1$-L-$R^2$, $R^2$-L-$R^1$, $R^1$-$R^2$ or $R^2$-$R^1$ wherein $R^1$ is an IPD101 polypeptide or chimeric IPD101 polypeptide of the disclosure and $R^2$ is a protein of interest. In some embodiments $R^1$ and $R^2$ are an IPD101 polypeptide or chimeric IPD101 polypeptide of the disclosure. The $R^1$ polypeptide is fused either directly or through a linker (L) segment to the $R^2$ polypeptide. The term "directly" defines fusions in which the polypeptides are joined without a peptide linker. Thus "L" represents a chemical bound or polypeptide segment to which both $R^1$ and $R^2$ are fused in frame, most commonly L is a linear peptide to which $R^1$ and $R^2$ are bound by amide bonds linking the carboxy terminus of $R^1$ to the amino terminus of L and carboxy terminus of L to the amino terminus of $R^2$. By "fused in frame" is meant that there is no translation termination or disruption between the reading frames of $R^1$ and $R^2$. The linking group (L) is generally a polypeptide of between 1 and 500 amino acids in length. The linkers joining the two molecules are preferably designed to (1) allow the two molecules to fold and act independently of each other, (2) not have a propensity for developing an ordered secondary structure which could interfere with the functional domains of the two proteins, (3) have minimal hydrophobic or charged characteristic which could interact with the functional protein domains and (4) provide steric separation of $R^1$ and $R^2$ such that $R^1$ and $R^2$ could interact simultaneously with their corresponding receptors on a single cell. Typically surface amino acids in flexible protein regions include Gly, Asn and Ser. Virtually any permutation of amino acid sequences containing Gly, Asn and Ser would be expected to satisfy the above criteria for a linker sequence. Other neutral amino acids, such as Thr and Ala, may also be used in the linker sequence. Additional amino acids may also be included in the linkers due to the addition of unique restriction sites in the linker sequence to facilitate construction of the fusions.

In some embodiments the linkers comprise sequences selected from the group of formulas: $(Gly_3Ser)_n$, $(Gly_4Ser)_n$, $(Gly_5Ser)_n$, $(Gly_nSer)_n$ or $(AlaGlySer)_n$ where n is an integer. One example of a highly-flexible linker is the (GlySer)-rich spacer region present within the pIII protein of the filamentous bacteriophages, e.g. bacteriophages M13 or fd (Schaller, et al., 1975). This region provides a long, flexible spacer region between two domains of the pIII surface protein. Also included are linkers in which an endopeptidase recognition sequence is included. Such a cleavage site may be valuable to separate the individual components of the fusion to determine if they are properly folded and active in vitro. Examples of various endopeptidases include, but are not limited to, Plasmin, Enterokinase, Kallikerin, Urokinase, Tissue Plasminogen activator, clostripain, Chymosin, Collagenase, Russell's Viper Venom Protease, Postproline cleavage enzyme, V8 protease, Thrombin and factor Xa. In some embodiments the linker comprises the amino acids EEKKN (SEQ ID NO:61) from the multi-gene expression vehicle (MGEV), which is cleaved by vacuolar proteases as disclosed in US Patent Application Publication Number US 2007/0277263. In other embodiments, peptide linker segments from the hinge region of heavy chain immunoglobulins IgG, IgA, IgM, IgD or IgE provide an angular relationship between the attached polypeptides. Especially useful are those hinge regions where the cysteines are replaced with serines. Linkers of the present disclosure include sequences derived from murine IgG gamma 2b hinge region in which the cysteines have been changed to serines. The fusion proteins are not limited by the form, size or number of linker sequences employed and the only requirement of the linker is that functionally it does not interfere adversely with the folding and function of the individual molecules of the fusion.

Nucleic Acid Molecules, and Variants and Fragments Thereof

Isolated or recombinant nucleic acid molecules comprising nucleic acid sequences encoding IPD101 polypeptides or biologically active portions thereof, as well as nucleic acid molecules sufficient for use as hybridization probes to identify nucleic acid molecules encoding proteins with regions of sequence homology are provided. As used herein, the term "nucleic acid molecule" refers to DNA molecules (e.g., recombinant DNA, cDNA, genomic DNA, plastid DNA, mitochondrial DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule (or DNA) is used herein to refer to a nucleic acid sequence (or DNA) that is no longer in its natural environment, for example in vitro. A "recombinant" nucleic acid molecule (or DNA) is used herein to refer to a nucleic acid sequence (or DNA) that is in a recombinant bacterial or plant host cell. In some embodiments, an "isolated" or "recombinant" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For purposes of the disclosure, "isolated" or "recombinant" when used to refer to nucleic acid molecules excludes isolated chromosomes. For example, in various embodiments, the recombinant nucleic acid molecules encoding IPD101 polypeptides can contain less than about 5 kb, 4 kb, 3 kb, 2 kb, 1 kb, 0.5 kb or 0.1 kb of nucleic acid sequences that naturally flank the nucleic acid molecule in genomic DNA of the cell from which the nucleic acid is derived.

In some embodiments an isolated nucleic acid molecule encoding IPD101 polypeptides has one or more change in the nucleic acid sequence compared to the native or genomic nucleic acid sequence. In some embodiments the change in the native or genomic nucleic acid sequence includes but is not limited to: changes in the nucleic acid sequence due to the degeneracy of the genetic code; changes in the nucleic acid sequence due to the amino acid substitution, insertion, deletion and/or addition compared to the native or genomic sequence; removal of one or more intron; deletion of one or more upstream or downstream regulatory regions; and deletion of the 5' and/or 3' untranslated region associated with the genomic nucleic acid sequence. In some embodiments the nucleic acid molecule encoding an IPD101 polypeptide is a non-genomic sequence.

A variety of polynucleotides that encode IPD101 polypeptides or related proteins are contemplated. Such polynucleotides are useful for production of IPD101 polypeptides in host cells when operably linked to a suitable promoter, transcription termination and/or polyadenylation sequences. Such polynucleotides are also useful as probes for isolating homologous or substantially homologous polynucleotides that encode IPD101 polypeptides or related proteins.

Polynucleotides Encoding IPD101 Polypeptides

One source of polynucleotides that encode IPD101 polypeptides or related proteins is a *Lysinibacillus* bacterium which may contain an IPD101 polynucleotide of any one of SEQ ID NOs: 1, 3, 5, 7, 9, 11, 13, 15, 19, 21, or 23, encoding an IPD101 polypeptide of SEQ ID NOs: 2, 4, 6, 8, 10, 12, 14, 16, 20, 22, or 24, respectively. The polynucleotides of any one or more of SEQ ID NOS: 1, 3, 5, 7, 9, 11, 13, 15, 17, 19, 21, 23, 27, 31, 45, 47, 49, 51, 53, 55, 57, or 59, can be used to express IPD101 polypeptides in recombinant bacterial hosts that include but are not limited to *Agrobacterium, Bacillus, Escherichia, Salmonella, Lysinibacillus, Acetobacter, Pseudomonas* and *Rhizobium* bacterial host cells. The polynucleotides are also useful as probes for isolating homologous or substantially homologous polynucleotides encoding IPD101 polypeptides or related proteins. Such probes can be used to identify homologous or substantially homologous polynucleotides derived from *Pseudomonas* species.

Polynucleotides encoding IPD101 polypeptides can also be synthesized de novo from an IPD101 polypeptide sequence. The sequence of the polynucleotide gene can be deduced from an IPD101 polypeptide sequence through use of the genetic code. Computer programs such as "Back-Translate" (GCG™ Package, Acclerys, Inc. San Diego, Calif.) can be used to convert a peptide sequence to the corresponding nucleotide sequence encoding the peptide. Examples of IPD101 polypeptide sequences that can be used to obtain corresponding nucleotide encoding sequences include, but are not limited to the IPD101 polypeptides of SEQ ID NOS: 2, 4, 6, 8, 10, 12, 14, 16, 18, 20, 22, 24, 25, 26, 28, 29, 30, 32, 46, 48, 50, 52, 54, 56, 58, and 60. Furthermore, synthetic IPD101 polynucleotide sequences of the disclosure can be designed so that they will be expressed in plants.

In some embodiments the nucleic acid molecule encoding an IPD101 polypeptide is a polynucleotide having the sequence set forth in any one of SEQ ID NOS: 1, 3, 5, 7, 9, 11, 13, 15, 17, 19, 21, 23, 27, 31, 45, 47, 49, 51, 53, 55, 57, or 59, and variants, fragments and complements thereof. "Complement" is used herein to refer to a nucleic acid sequence that is sufficiently complementary to a given nucleic acid sequence such that it can hybridize to the given nucleic acid sequence to thereby form a stable duplex. "Polynucleotide sequence variants" is used herein to refer to a nucleic acid sequence that except for the degeneracy of the genetic code encodes the same polypeptide.

In some embodiments the nucleic acid molecule encoding the IPD101 polypeptide is a non-genomic nucleic acid sequence. As used herein a "non-genomic nucleic acid sequence" or "non-genomic nucleic acid molecule" or "non-genomic polynucleotide" refers to a nucleic acid molecule that has one or more change in the nucleic acid sequence compared to a native or genomic nucleic acid sequence. In some embodiments the change to a native or genomic nucleic acid molecule includes but is not limited to: changes in the nucleic acid sequence due to the degeneracy of the genetic code; optimization of the nucleic acid sequence for expression in plants; changes in the nucleic acid sequence to introduce at least one amino acid substitution, insertion, deletion and/or addition compared to the native or genomic sequence; removal of one or more intron associated with the genomic nucleic acid sequence; insertion of one or more heterologous introns; deletion of one or more upstream or downstream regulatory regions associated with the genomic nucleic acid sequence; insertion of one or more heterologous upstream or downstream regulatory regions; deletion of the 5' and/or 3' untranslated region associated with the genomic nucleic acid sequence; insertion of a heterologous 5' and/or 3' untranslated region; and modification of a polyadenylation site. In some embodiments the non-genomic nucleic acid molecule is a synthetic nucleic acid sequence.

In some embodiments the nucleic acid molecule encoding an IPD101 polypeptide disclosed herein is a non-genomic polynucleotide having a nucleotide sequence having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater identity, to the nucleic acid sequence of any one of SEQ ID NOS: 1, 3, 5, 7, 9, 11, 13, 15, 17, 19, 21, 23, 27, 31, 45, 47, 49, 51, 53, 55, 57, or 59, wherein the IPD101 polypeptide has insecticidal activity.

In some embodiments the nucleic acid molecule encodes an IPD101 polypeptide variant comprising one or more amino acid substitutions to the amino acid sequence of any one of SEQ ID NOS: 2, 4, 6, 8, 10, 12, 14, 16, 18, 20, 22, 24, 25, 26, 28, 29, 30, 32, 46, 48, 50, 52, 54, 56, 58, and 60.

Also provided are nucleic acid molecules that encode transcription and/or translation products that are subsequently spliced to ultimately produce functional IPD101 polypeptides. Splicing can be accomplished in vitro or in vivo, and can involve cis- or trans-splicing. The substrate for splicing can be polynucleotides (e.g., RNA transcripts) or polypeptides. An example of cis-splicing of a polynucleotide is where an intron inserted into a coding sequence is removed and the two flanking exon regions are spliced to generate an IPD101 polypeptide encoding sequence. An example of trans-splicing would be where a polynucleotide is encrypted by separating the coding sequence into two or more fragments that can be separately transcribed and then spliced to form the full-length pesticidal encoding sequence. The use of a splicing enhancer sequence, which can be introduced into a construct, can facilitate splicing either in cis or trans-splicing of polypeptides (U.S. Pat. Nos. 6,365,377 and 6,531,316). Thus, in some embodiments the polynucleotides do not directly encode a full-length IPD101 polypeptide, but rather encode a fragment or fragments of an IPD101 polypeptide. These polynucleotides can be used to express a functional IPD101 polypeptide through a mechanism involving splicing, where splicing can occur at the level of polynucleotide (e.g., intron/exon) and/or polypeptide (e.g., intein/extein). This can be useful, for example, in controlling expression of pesticidal activity, since a functional pesticidal polypeptide will only be expressed if all required fragments are expressed in an environment that permits splicing processes to generate functional product. In another example, introduction of one or more insertion sequences into a polynucleotide can facilitate recombination with a low homology polynucleotide; use of an intron or intein for the insertion sequence facilitates the removal of the intervening sequence, thereby restoring function of the encoded variant.

Nucleic acid molecules that are fragments of these nucleic acid sequences encoding IPD101 polypeptides are also encompassed by the embodiments. "Fragment" as used herein refers to a portion of the nucleic acid sequence encoding an IPD101 polypeptide. A fragment of a nucleic acid sequence may encode a biologically active portion of an IPD101 polypeptide or it may be a fragment that can be used as a hybridization probe or PCR primer using methods disclosed below. Nucleic acid molecules that are fragments of a nucleic acid sequence encoding an IPD101 polypeptide comprise at least about 150, 180, 210, 240, 270, 300, 330, 360, 400, 450, or 500 contiguous nucleotides or up to the number of nucleotides present in a full-length nucleic acid sequence encoding an IPD101 polypeptide disclosed herein, depending upon the intended use. "Contiguous nucleotides" is used herein to refer to nucleotide residues that are immediately adjacent to one another. Fragments of the nucleic acid sequences of the embodiments will encode protein fragments that retain the biological activity of the IPD101 polypeptide and, hence, retain insecticidal activity. "Retains insecticidal activity" is used herein to refer to a polypeptide having at least about 10%, at least about 30%, at least about 50%, at least about 70%, 80%, 90%, 95% or higher of the insecticidal activity of any one of the full-length IPD101 polypeptides set forth in SEQ ID NOS: 2, 4, 6, 8, 10, 12, 14, 16, 18, 20, 22, 24, 25, 26, 28, 29, 30, 32, 46, 48, 50, 52, 54, 56, 58, and 60. In some embodiments, the insecticidal activity is against a Lepidopteran species. In one embodiment, the insecticidal activity is against a Coleopteran species. In some embodiments, the insecticidal activity is against one or more insect pests of the corn rootworm complex: western corn rootworm, *Diabrotica virgifera*; northern corn rootworm, *D. barberi*: Southern corn rootworm or spotted cucumber beetle; *Diabrotica undecimpunctata howardi, Diabrotica speciosa*, and the Mexican corn rootworm, *D. virgifera zeae*. In one embodiment, the insecticidal activity is against a *Diabrotica* species.

In some embodiments the IPD101 polypeptide is encoded by a nucleic acid sequence sufficiently homologous to any one of the nucleic acid sequences of SEQ ID NOS: 1, 3, 5, 7, 9, 11, 13, 15, 17, 19, 21, 23, 27, 31, 45, 47, 49, 51, 53, 55, 57, or 59.

To determine the percent identity of two amino acid sequences or of two nucleic acid sequences, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. In another embodiment, the comparison is across the entirety of the reference sequence (e.g., across the entirety of SEQ ID NO: 1). The percent identity between two sequences can be determined using techniques similar to those described below, with or without allowing gaps. In calculating percent identity, typically exact matches are counted.

Another non-limiting example of a mathematical algorithm utilized for the comparison of sequences is the algorithm of Needleman and Wunsch, (1970) *J. Mol. Biol.* 48(3):443-453, used GAP Version 10 software to determine sequence identity or similarity using the following default parameters: % identity and % similarity for a nucleic acid sequence using GAP Weight of 50 and Length Weight of 3, and the nwsgapdna.cmpii scoring matrix; % identity or % similarity for an amino acid sequence using GAP weight of 8 and length weight of 2, and the BLOSUM62 scoring program. Equivalent programs may also be used. "Equivalent program" is used herein to refer to any sequence comparison program that, for any two sequences in question, generates an alignment having identical nucleotide residue matches and an identical percent sequence identity when compared to the corresponding alignment generated by GAP Version 10.

In some embodiments an IPD101 polynucleotide encodes an IPD101 polypeptide comprising an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99% or greater identity across the entire length of the amino acid sequence of any one of SEQ ID NOS: 2, 4, 6, 8, 10, 12, 14, 16, 18, 20, 22, 24, 25, 26, 28, 29, 30, 32, 46, 48, 50, 52, 54, 56, 58, and 60.

In some embodiments polynucleotides are provided encoding chimeric polypeptides comprising regions of at least two different IPD101 polypeptides of the disclosure.

In some embodiments polynucleotides are provided encoding chimeric polypeptides comprising an N-terminal Region of a first IPD101 polypeptide of the disclosure operably fused to a C-terminal Region of a second IPD101 polypeptide of the disclosure.

The embodiments also encompass nucleic acid molecules encoding IPD101 polypeptide variants. "Variants" of the IPD101 polypeptide encoding nucleic acid sequences include those sequences that encode the IPD101 polypeptides disclosed herein but that differ conservatively because of the degeneracy of the genetic code as well as those that are sufficiently identical as discussed above. Naturally occurring allelic variants can be identified with the use of well-known molecular biology techniques, such as polymerase chain reaction (PCR) and hybridization techniques as outlined below. Variant nucleic acid sequences also include synthetically derived nucleic acid sequences that have been generated, for example, by using site-directed mutagenesis but which still encode the IPD101 polypeptides disclosed as discussed below.

The present disclosure provides isolated or recombinant polynucleotides that encode any of the IPD101 polypeptides disclosed herein. Those having ordinary skill in the art will readily appreciate that due to the degeneracy of the genetic code, a multitude of nucleotide sequences encoding IPD101 polypeptides of the present disclosure exist.

The skilled artisan will further appreciate that changes can be introduced by mutation of the nucleic acid sequences thereby leading to changes in the amino acid sequence of the encoded IPD101 polypeptides, without altering the biological activity of the proteins. Thus, variant nucleic acid molecules can be created by introducing one or more nucleotide substitutions, additions and/or deletions into the corresponding nucleic acid sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleic acid sequences are also encompassed by the present disclosure.

Alternatively, variant nucleic acid sequences can be made by introducing mutations randomly along all or part of the coding sequence, such as by saturation mutagenesis, and the resultant mutants can be screened for ability to confer pesticidal activity to identify mutants that retain activity. Following mutagenesis, the encoded protein can be expressed recombinantly, and the activity of the protein can be determined using standard assay techniques.

The polynucleotides of the disclosure and fragments thereof are optionally used as substrates for a variety of recombination and recursive recombination reactions, in addition to standard cloning methods as set forth in, e.g., Ausubel, Berger and Sambrook, i.e., to produce additional pesticidal polypeptide homologues and fragments thereof with desired properties. A variety of such reactions are known. Methods for producing a variant of any nucleic acid listed herein comprising recursively recombining such polynucleotide with a second (or more) polynucleotide, thus forming a library of variant polynucleotides are also embodiments of the disclosure, as are the libraries produced, the cells comprising the libraries and any recombinant polynucleotide produced by such methods. Additionally, such methods optionally comprise selecting a variant polynucleotide from such libraries based on pesticidal activity, as is wherein such recursive recombination is done in vitro or in vivo.

A variety of diversity generating protocols, including nucleic acid recursive recombination protocols are available and fully described in the art. The procedures can be used separately, and/or in combination to produce one or more variants of a nucleic acid or set of nucleic acids, as well as variants of encoded proteins. Individually and collectively, these procedures provide robust, widely applicable ways of generating diversified nucleic acids and sets of nucleic acids (including, e.g., nucleic acid libraries) useful, e.g., for the engineering or rapid evolution of nucleic acids, proteins, pathways, cells and/or organisms with new and/or improved characteristics.

While distinctions and classifications are made in the course of the ensuing discussion for clarity, it will be appreciated that the techniques are often not mutually exclusive. Indeed, the various methods can be used singly or in combination, in parallel or in series, to access diverse sequence variants.

The result of any of the diversity generating procedures described herein can be the generation of one or more nucleic acids, which can be selected or screened for nucleic acids with or which confer desirable properties or that encode proteins with or which confer desirable properties. Following diversification by one or more of the methods herein or otherwise available to one of skill, any nucleic acids that are produced can be selected for a desired activity or property, e.g. pesticidal activity or, such activity at a desired pH, etc. This can include identifying any activity that can be detected, for example, in an automated or automatable format, by any of the assays in the art, see, e.g., discussion of screening of insecticidal activity, infra. A variety of related (or even unrelated) properties can be evaluated, in serial or in parallel, at the discretion of the practitioner.

Descriptions of a variety of diversity generating procedures for generating modified nucleic acid sequences, e.g., those coding for polypeptides having pesticidal activity or fragments thereof, are found in the following publications and the references cited therein: Soong, et al., (2000) *Nat Genet* 25(4):436-439; Stemmer, et al., (1999) *Tumor Targeting* 4:1-4; Ness, et al., (1999) *Nat Biotechnol* 17:893-896; Chang, et al., (1999) *Nat Biotechnol* 17:793-797; Minshull and Stemmer, (1999) *Curr Opin Chem Biol* 3:284-290; Christians, et al., (1999) *Nat Biotechnol* 17:259-264; Crameri, et al., (1998) *Nature* 391:288-291; Crameri, et al., (1997) *Nat Biotechnol* 15:436-438; Zhang, et al., (1997) *PNAS USA* 94:4504-4509; Patten, et al., (1997) *Curr Opin Biotechnol* 8:724-733; Crameri, et al., (1996) *Nat Med* 2:100-103; Crameri, et al., (1996) *Nat Biotechnol* 14:315-319; Gates, et al., (1996) *J Mol Biol* 255:373-386; Stemmer, (1996) "Sexual PCR and Assembly PCR" In: *The Encyclopedia of Molecular Biology*. VCH Publishers, New York. pp. 447-457; Crameri and Stemmer, (1995) *BioTechniques* 18:194-195; Stemmer, et al., (1995) *Gene*, 164:49-53; Stemmer, (1995) *Science* 270: 1510; Stemmer, (1995) *Bio/Technology* 13:549-553; Stemmer, (1994) *Nature* 370:389-391 and Stemmer, (1994) *PNAS USA* 91:10747-10751.

Mutational methods of generating diversity include, for example, site-directed mutagenesis (Ling, et al., (1997) *Anal Biochem* 254(2):157-178; Dale, et al., (1996) *Methods Mol Biol* 57:369-374; Smith, (1985) *Ann Rev Genet* 19:423-462; Botstein and Shortle, (1985) *Science* 229:1193-1201; Carter, (1986) *Biochem J* 237:1-7 and Kunkel, (1987) "The efficiency of oligonucleotide directed mutagenesis" in *Nucleic Acids & Molecular Biology* (Eckstein and Lilley, eds., Springer Verlag, Berlin)); mutagenesis using uracil containing templates (Kunkel, (1985) *PNAS USA* 82:488-492; Kunkel, et al., (1987) *Methods Enzymol* 154:367-382 and Bass, et al., (1988) *Science* 242:240-245); oligonucleotide-directed mutagenesis (Zoller and Smith, (1983) *Methods Enzymol* 100:468-500; Zoller and Smith, (1987) *Methods Enzymol* 154:329-350 (1987); Zoller and Smith, (1982) *Nucleic Acids Res* 10:6487-6500), phosphorothioate-modified DNA mutagenesis (Taylor, et al., (1985) *Nucl Acids Res* 13:8749-8764; Taylor, et al., (1985) *Nucl Acids Res* 13:8765-8787 (1985); Nakamaye and Eckstein, (1986) *Nucl Acids Res* 14:9679-9698; Sayers, et al., (1988) *Nucl Acids Res* 16:791-802 and Sayers, et al., (1988) *Nucl Acids Res* 16:803-814); mutagenesis using gapped duplex DNA (Kramer, et al., (1984) *Nucl Acids Res* 12:9441-9456; Kramer and Fritz, (1987) *Methods Enzymol* 154:350-367; Kramer, et al., (1988) *Nucl Acids Res* 16:7207 and Fritz, et al., (1988) *Nucl Acids Res* 16:6987-6999).

Additional suitable methods include point mismatch repair (Kramer, et al., (1984) *Cell* 38:879-887), mutagenesis using repair-deficient host strains (Carter, et al., (1985) *Nucl Acids Res* 13:4431-4443 and Carter, (1987) *Methods in Enzymol* 154:382-403), deletion mutagenesis (Eghtedarzadeh and Henikoff, (1986) *Nucl Acids Res* 14:5115), restriction-selection and restriction-purification (Wells, et al., (1986) *Phil Trans R Soc Lond A* 317:415-423), mutagenesis by total gene synthesis (Nambiar, et al., (1984) *Science* 223:1299-1301; Sakamar and Khorana, (1988) *Nucl Acids Res* 14:6361-6372; Wells, et al., (1985) *Gene* 34:315-323 and Grundström, et al., (1985) *Nucl Acids Res* 13:3305-3316), double-strand break repair (Mandecki, (1986) *PNAS USA*, 83:7177-7181 and Arnold, (1993) *Curr Opin Biotech* 4:450-455). Additional details on many of the above methods can be found in *Methods Enzymol* Volume 154, which also describes useful controls for trouble-shooting problems with various mutagenesis methods.

Additional details regarding various diversity generating methods can be found in the following US patents, PCT Publications and Applications and EPO publications: U.S. Pat. Nos. 5,723,323, 5,763,192, 5,814,476, 5,817,483, 5,824,514, 5,976,862, 5,605,793, 5,811,238, 5,830,721, 5,834,252, 5, 837,458, WO 1995/22625, WO 1996/33207, WO 1997/20078, WO 1997/35966, WO 1999/41402, WO 1999/41383, WO 1999/41369, WO 1999/41368, EP 752008, EP 1012670, WO 1999/23107, WO 1999/21979, WO 1998/31837, WO 1998/27230, WO 1998/27230, WO 2000/00632, WO 2000/09679, WO 1998/42832, WO 1999/29902, WO 1998/41653, WO 1998/41622, WO 1998/42727, WO 2000/18906, WO 2000/04190, WO 2000/42561, WO 2000/42559, WO 2000/42560, WO 2001/23401 and PCT/US01/06775.

The nucleotide sequences of the embodiments can also be used to isolate corresponding sequences from a bacterial source, including but not limited to a *Pseudomonas* species. In this manner, methods such as PCR, hybridization, and the like can be used to identify such sequences based on their sequence homology to the sequences set forth herein. Sequences that are selected based on their sequence identity to the entire sequences set forth herein or to fragments thereof are encompassed by the embodiments. Such sequences include sequences that are orthologs of the disclosed sequences. The term "orthologs" refers to genes derived from a common ancestral gene and which are found in different species as a result of speciation. Genes found in different species are considered orthologs when their nucleotide sequences and/or their encoded protein sequences share substantial identity as defined elsewhere herein. Functions of orthologs are often highly conserved among species.

In a PCR approach, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook, et al., (1989) *Molecular Cloning: A Laboratory Manual* (2d ed., Cold Spring Harbor Laboratory Press, Plainview, N.Y.), hereinafter "Sambrook". See also, Innis, et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

To identify potential IPD101 polypeptides from bacterium collections, the bacterial cell lysates can be screened with antibodies generated against IPD101 polypeptides using Western blotting and/or ELISA methods. This type of assay can be performed in a high throughput fashion. Positive samples can be further analyzed by various techniques such as antibody based protein purification and identification. Methods of generating antibodies are well known in the art as discussed infra.

Alternatively, mass spectrometry based protein identification method can be used to identify homologs of IPD101 polypeptides using protocols in the literatures (Scott Patterson, (1998), 10.22, 1-24, Current Protocol in Molecular Biology published by John Wiley & Son Inc). Specifically, LC-MS/MS based protein identification method is used to associate the MS data of given cell lysate or desired molecular weight enriched samples (excised from SDS-PAGE gel of relevant molecular weight bands to IPD101 polypeptides) with sequence information of an IPD101 polypeptide disclosed herein. Any match in peptide sequences indicates the potential of having the homologous proteins in the samples. Additional techniques (protein purification and molecular biology) can be used to isolate the protein and identify the sequences of the homologs.

In hybridization methods, all or part of the pesticidal nucleic acid sequence can be used to screen cDNA or genomic libraries. Methods for construction of such cDNA and genomic libraries are generally known in the art and are disclosed in Sambrook and Russell, (2001), supra. The so-called hybridization probes may be genomic DNA fragments, cDNA fragments, RNA fragments or other oligonucleotides and may be labeled with a detectable group such as 32P or any other detectable marker, such as other radioisotopes, a fluorescent compound, an enzyme or an enzyme co-factor. Probes for hybridization can be made by labeling synthetic oligonucleotides based on the known IPD101 polypeptide-encoding nucleic acid sequences disclosed herein. Degenerate primers designed on the basis of conserved nucleotides or amino acid residues in the nucleic acid sequence or encoded amino acid sequence can additionally be used. The probe typically comprises a region of nucleic acid sequence that hybridizes under stringent conditions to at least about 12, at least about 25, at least about 50, 75, 100, 125, 150, 175 or 200 consecutive nucleotides of nucleic acid sequences encoding IPD101 polypeptides of the disclosure or a fragment or variant thereof. Methods for the preparation of probes for hybridization and stringency conditions are generally known in the art and are disclosed in Sambrook and Russell, (2001), supra, herein incorporated by reference.

For example, an entire nucleic acid sequence, encoding an IPD101 polypeptide, disclosed herein or one or more portions thereof may be used as a probe capable of specifically hybridizing to corresponding nucleic acid sequences encoding IPD101 polypeptide-like sequences and messenger RNAs. To achieve specific hybridization under a variety of conditions, such probes include sequences that are unique and are preferably at least about 10 nucleotides in length or at least about 20 nucleotides in length. Such probes may be used to amplify corresponding pesticidal sequences from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook, et al., (1989) Molecular Cloning: A Laboratory Manual (2d ed., Cold Spring Harbor Laboratory Press, Cold Spring Harbor, N.Y.).

Hybridization of such sequences may be carried out under stringent conditions. "Stringent conditions" or "stringent hybridization conditions" is used herein to refer to conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length Antibodies Antibodies to an IPD101 polypeptide of the embodiments or to variants or fragments thereof are also encompassed. The antibodies of the disclosure include polyclonal and monoclonal antibodies as well as fragments thereof which retain their ability to bind to an IPD101 polypeptide. An antibody, monoclonal antibody or fragment thereof is said to be capable of binding a molecule if it is capable of specifically reacting with the molecule to thereby bind the molecule to the antibody, monoclonal antibody or fragment thereof. The term "antibody" (Ab) or "monoclonal antibody" (Mab) is meant to include intact molecules as well as fragments or binding regions or domains thereof (such as, for example, Fab and F(ab).sub.2 fragments) which are capable of binding hapten. Such fragments are typically produced by proteolytic cleavage, such as papain or pepsin. Alternatively, hapten-binding fragments can be produced through the application of recombinant DNA technology or through synthetic chemistry. Methods for the preparation of the antibodies of the present disclosure are generally known in the art. For example, see, Antibodies, A Laboratory Manual, Ed Harlow and David Lane (eds.) Cold Spring Harbor Laboratory, N.Y. (1988), as well as the references cited therein. Standard reference works setting forth the general principles of immunology include: Klein, J. Immunology: The Science of Cell-Noncell Discrimination, John Wiley & Sons, N.Y. (1982); Dennett, et al., Monoclonal Antibodies, Hybridoma: A New Dimension in Biological Analyses, Plenum Press, N.Y. (1980) and Campbell, "Monoclonal Antibody Technology," In Laboratory Techniques in Biochemistry and Molecular Biology, Vol. 13, Burdon, et al., (eds.), Elsevier, Amsterdam (1984). See also, U.S. Pat. Nos. 4,196,265; 4,609,893; 4,713,325; 4,714,681; 4,716,111; 4,716,117 and 4,720,459. Antibodies against IPD101 polypeptides or antigen-binding portions thereof can be produced by a variety of techniques, including conventional monoclonal antibody methodology, for example the standard somatic cell hybridization technique of Kohler and Milstein, (1975) *Nature* 256:495. Other techniques for producing monoclonal antibody can also be employed such as viral or oncogenic transformation of B lymphocytes. An animal system for preparing hybridomas is a murine system. Immunization protocols and techniques for isolation of immunized splenocytes for fusion are known in the art. Fusion partners (e.g., murine myeloma cells) and fusion procedures are also known. The antibody and monoclonal antibodies of the disclosure can be prepared by utilizing an IPD101 polypeptide as antigens.

A kit for detecting the presence of an IPD101 polypeptide or detecting the presence of a nucleotide sequence encoding an IPD101 polypeptide in a sample is provided. In one embodiment, the kit provides antibody-based reagents for detecting the presence of an IPD101 polypeptide in a tissue sample. In another embodiment, the kit provides labeled nucleic acid probes useful for detecting the presence of one or more polynucleotides encoding an IPD101 polypeptide. The kit is provided along with appropriate reagents and controls for carrying out a detection method, as well as instructions for use of the kit.

Receptor Identification and Isolation

Receptors to the IPD101 polypeptides of the embodiments or to variants or fragments thereof are also encompassed. Methods for identifying receptors are well known in the art (see, Hofmann, et. al., (1988) *Eur. J. Biochem.* 173:85-91; Gill, et al., (1995) *J. Biol. Chem.* 27277-27282) can be employed to identify and isolate the receptor that recognizes the IPD101 polypeptide using the brush-border membrane vesicles from susceptible insects. In addition to the radioactive labeling method listed in the cited literatures, an IPD101 polypeptide can be labeled with fluorescent dye and other common labels such as streptavidin. Brush-border membrane vesicles (BBMV) of susceptible insects such as soybean looper and stink bugs can be prepared according to the protocols listed in the references of Hofmann and Gill above and separated on SDS-PAGE gel and blotted on suitable membrane. Labeled IPD101 polypeptide can be incubated with blotted membrane of BBMV and labeled IPD101 polypeptide can be identified with the labeled reporters. Identification of protein band(s) that interact with the IPD101 polypeptide can be detected by N-terminal amino acid gas phase sequencing or mass spectrometry based protein identification method (Patterson, (1998) 10.22, 1-24, Current Protocol in Molecular Biology published by John Wiley & Son Inc). Once the protein is identified, the corresponding gene can be cloned from genomic DNA or cDNA library of the susceptible insects and binding affinity can be measured directly with the IPD101 polypeptide. Receptor function for insecticidal activity by the IPD101 polypeptide can be verified by RNAi type of gene knock out method (Rajagopal, et al., (2002) *J. Biol. Chem.* 277:46849-46851).

Nucleotide Constructs, Expression Cassettes and Vectors

The use of the term "nucleotide constructs" herein is not intended to limit the embodiments to nucleotide constructs comprising DNA. Those of ordinary skill in the art will recognize that nucleotide constructs, particularly polynucleotides and oligonucleotides composed of ribonucleotides and combinations of ribonucleotides and deoxyribonucleotides, may also be employed in the methods disclosed herein. The nucleotide constructs, nucleic acids, and nucleotide sequences of the embodiments additionally encompass all complementary forms of such constructs, molecules, and sequences. Further, the nucleotide constructs, nucleotide molecules, and nucleotide sequences of the embodiments encompass all nucleotide constructs, molecules, and sequences which can be employed in the methods of the embodiments for transforming plants including, but not limited to, those comprised of deoxyribonucleotides, ribonucleotides, and combinations thereof. Such deoxyribonucleotides and ribonucleotides include both naturally occurring molecules and synthetic analogues. The nucleotide constructs, nucleic acids, and nucleotide sequences of the embodiments also encompass all forms of nucleotide constructs including, but not limited to, single-stranded forms, double-stranded forms, hairpins, stem-and-loop structures and the like.

A further embodiment relates to a transformed organism such as an organism selected from plant and insect cells, bacteria, yeast, baculovirus, protozoa, nematodes and algae. The transformed organism comprises a DNA molecule of the embodiments, an expression cassette comprising the DNA molecule or a vector comprising the expression cassette, which may be stably incorporated into the genome of the transformed organism.

The sequences of the embodiments are provided in DNA constructs for expression in the organism of interest. The construct will include 5' and 3' regulatory sequences operably linked to a sequence of the embodiments. The term "operably linked" as used herein refers to a functional linkage between a promoter and a second sequence, wherein the promoter sequence initiates and mediates transcription of the DNA sequence corresponding to the second sequence. Generally, operably linked means that the nucleic acid sequences being linked are contiguous and where necessary to join two protein coding regions in the same reading frame. The construct may additionally contain at least one additional gene to be cotransformed into the organism. Alternatively, the additional gene(s) can be provided on multiple DNA constructs.

Such a DNA construct is provided with a plurality of restriction sites for insertion of the IPD101 polypeptide gene sequence of the disclosure to be under the transcriptional regulation of the regulatory regions. The DNA construct may additionally contain selectable marker genes.

The DNA construct will generally include in the 5' to 3' direction of transcription: a transcriptional and translational initiation region (i.e., a promoter), a DNA sequence of the embodiments, and a transcriptional and translational termination region (i.e., termination region) functional in the organism serving as a host. The transcriptional initiation region (i.e., the promoter) may be native, analogous, foreign or heterologous to the host organism and/or to the sequence of the embodiments. Additionally, the promoter may be the natural sequence or alternatively a synthetic sequence. The term "foreign" as used herein indicates that the promoter is not found in the native organism into which the promoter is introduced. Where the promoter is "foreign" or "heterologous" to the sequence of the embodiments, it is intended that the promoter is not the native or naturally occurring promoter for the operably linked sequence of the embodiments. As used herein, a chimeric gene comprises a coding sequence operably linked to a transcription initiation region that is heterologous to the coding sequence. Where the promoter is a native or natural sequence, the expression of the operably linked sequence is altered from the wild-type expression, which results in an alteration in phenotype.

In some embodiments the DNA construct comprises a polynucleotide encoding an IPD101 polypeptide of the embodiments. In some embodiments the DNA construct comprises a polynucleotide encoding a fusion protein comprising an IPD101 polypeptide of the embodiments.

In some embodiments the DNA construct may also include a transcriptional enhancer sequence. As used herein, the term an "enhancer" refers to a DNA sequence which can stimulate promoter activity, and may be an innate element of the promoter or a heterologous element inserted to enhance the level or tissue-specificity of a promoter. Various enhancers are known in the art including for example, introns with gene expression enhancing properties in plants (US Patent Application Publication Number 2009/0144863, the ubiquitin intron (i.e., the maize ubiquitin intron 1 (see, for example, NCBI sequence S94464)), the omega enhancer or the omega prime enhancer (Gallie, et al., (1989) *Molecular Biology of RNA* ed. Cech (Liss, New York) 237-256 and Gallie, et al., (1987) *Gene* 60:217-25), the CaMV 35S enhancer (see, e.g., Benfey, et al., (1990) *EMBO J.* 9:1685-96) and the enhancers of U.S. Pat. No. 7,803,992 may also be used. The above list of transcriptional enhancers is not meant to be limiting. Any appropriate transcriptional enhancer can be used in the embodiments.

The termination region may be native with the transcriptional initiation region, may be native with the operably linked DNA sequence of interest, may be native with the plant host or may be derived from another source (i.e., foreign or heterologous to the promoter, the sequence of interest, the plant host or any combination thereof).

Convenient termination regions are available from the Ti-plasmid of *A. tumefaciens*, such as the octopine synthase and nopaline synthase termination regions. See also, Guerineau, et al., (1991) *Mol. Gen. Genet.* 262:141-144; Proudfoot, (1991) *Cell* 64:671-674; Sanfacon, et al., (1991) *Genes Dev.* 5:141-149; Mogen, et al., (1990) *Plant Cell* 2:1261-1272; Munroe, et al., (1990) *Gene* 91:151-158; Ballas, et al., (1989) *Nucleic Acids Res.* 17:7891-7903 and Joshi, et al., (1987) *Nucleic Acid Res.* 15:9627-9639.

Where appropriate, a nucleic acid may be optimized for increased expression in the host organism. Thus, where the host organism is a plant, the synthetic nucleic acids can be synthesized using plant-preferred codons for improved expression. See, for example, Campbell and Gowri, (1990) *Plant Physiol.* 92:1-11 for a discussion of host-preferred usage. For example, although nucleic acid sequences of the embodiments may be expressed in both monocotyledonous and dicotyledonous plant species, sequences can be modified to account for the specific preferences and GC content preferences of monocotyledons or dicotyledons as these preferences have been shown to differ (Murray et al. (1989) *Nucleic Acids Res.* 17:477-498). Thus, the maize-preferred for a particular amino acid may be derived from known gene sequences from maize. Maize usage for 28 genes from maize plants is listed in Table 4 of Murray, et al., supra. Methods are available in the art for synthesizing plant-preferred genes. See, for example, Murray, et al., (1989) *Nucleic Acids Res.* 17:477-498, and Liu H et al. *Mol Bio Rep* 37:677-684, 2010, herein incorporated by reference. A *Zea maize* usage table can be also found at kazusa.or.jp//cgi-bin/show.cgi?species=4577, which can be accessed using the www prefix. A *Glycine max* usage table can be found at kazusa.or.jp// cgi-bin/show.cgi?species=3847&aa=1&style=N, which can be accessed using the www prefix.

In some embodiments the recombinant nucleic acid molecule encoding an IPD101 polypeptide has maize optimized codons.

Additional sequence modifications are known to enhance gene expression in a cellular host. These include elimination of sequences encoding spurious polyadenylation signals, exon-intron splice site signals, transposon-like repeats, and other well-characterized sequences that may be deleterious to gene expression. The GC content of the sequence may be adjusted to levels average for a given cellular host, as calculated by reference to known genes expressed in the host cell. The term "host cell" as used herein refers to a cell which contains a vector and supports the replication and/or expression of the expression vector is intended. Host cells may be prokaryotic cells such as *E. coli* or eukaryotic cells such as yeast, insect, amphibian or mammalian cells or monocotyledonous or dicotyledonous plant cells. An example of a monocotyledonous host cell is a maize host cell. When possible, the sequence is modified to avoid predicted hairpin secondary mRNA structures.

The expression cassettes may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein, et al., (1989) *Proc. Natl. Acad. Sci. USA* 86:6126-6130); potyvirus leaders, for example, TEV leader (Tobacco Etch Virus) (Gallie, et al., (1995) *Gene* 165(2):233-238), MDMV leader (Maize Dwarf Mosaic Virus), human immunoglobulin heavy-chain binding protein (BiP) (Macejak, et al., (1991) *Nature* 353:90-94); untranslated leader from the coat protein mRNA of alfalfa mosaic virus (AMV RNA 4) (Jobling, et al., (1987) *Nature* 325:622-625); tobacco mosaic virus leader (TMV) (Gallie, et al., (1989) in *Molecular Biology of RNA*, ed. Cech (Liss, New York), pp. 237-256) and maize chlorotic mottle virus leader (MCMV) (Lommel, et al., (1991) *Virology* 81:382-385). See also, Della-Cioppa, et al., (1987) *Plant Physiol.* 84:965-968. Such constructs may also contain a "signal sequence" or "leader sequence" to facilitate co-translational or post-translational transport of the peptide to certain intracellular structures such as the chloroplast (or other plastid), endoplasmic reticulum or Golgi apparatus.

"Signal sequence" as used herein refers to a sequence that is known or suspected to result in cotranslational or post-translational peptide transport across the cell membrane. In eukaryotes, this typically involves secretion into the Golgi apparatus, with some resulting glycosylation. Insecticidal toxins of bacteria are often synthesized as protoxins, which are proteolytically activated in the gut of the target pest (Chang, (1987) *Methods Enzymol.* 153:507-516). In some embodiments, the signal sequence is located in the native sequence or may be derived from a sequence of the embodiments. "Leader sequence" as used herein refers to any sequence that when translated, results in an amino acid sequence sufficient to trigger co-translational transport of the peptide chain to a subcellular organelle. Thus, this includes leader sequences targeting transport and/or glycosylation by passage into the endoplasmic reticulum, passage to vacuoles, plastids including chloroplasts, mitochondria, and the like. Nuclear-encoded proteins targeted to the chloroplast thylakoid lumen compartment have a characteristic bipartite transit peptide, composed of a stromal targeting signal peptide and a lumen targeting signal peptide. The stromal targeting information is in the amino-proximal portion of the transit peptide. The lumen targeting signal peptide is in the carboxyl-proximal portion of the transit peptide, and contains all the information for targeting to the lumen. Recent research in proteomics of the higher plant chloroplast has achieved in the identification of numerous nuclear-encoded lumen proteins (Kieselbach et al. *FEBS LETT* 480:271-276, 2000; Peltier et al. Plant Cell 12:319-341, 2000; Bricker et al. *Biochim. Biophys Acta* 1503:350-356, 2001), the lumen targeting signal peptide of which can potentially be used in accordance with the present disclosure. About 80 proteins from *Arabidopsis*, as well as homologous proteins from spinach and garden pea, are reported by Kieselbach et al., *Photosynthesis Research,* 78:249-264, 2003. In particular, Table 2 of this publication, which is incorporated into the description herewith by reference, discloses 85 proteins from the chloroplast lumen, identified by their accession number (see also US Patent Application Publication 2009/09044298).

Suitable chloroplast transit peptides (CTP) are well known to one skilled in the art also include chimeric CT's comprising but not limited to, an N-terminal domain, a central domain or a C-terminal domain from a CTP from *Oryza sativa* 1-decoy-D xylose-5-Phosphate Synthase *Oryza sativa*-Superoxide dismutase *Oryza sativa*-soluble starch synthase *Oryza sativa*-NADP-dependent Malic acid enzyme *Oryza sativa*-Phospho-2-dehydro-3-deoxyheptonate Aldolase 2 *Oryza sativa*-L-Ascorbate peroxidase 5 *Oryza sativa*-Phosphoglucan water dikinase, *Zea Mays* ssRUBISCO, *Zea Mays*-beta-glucosidase, *Zea Mays*-Malate dehydrogenase, *Zea Mays* Thioredoxin M-type (See US Patent Application Publication 2012/0304336).

The IPD101 polypeptide gene to be targeted to the chloroplast may be optimized for expression in the chloroplast to account for differences in usage between the plant nucleus and this organelle. In this manner, the nucleic acids of interest may be synthesized using chloroplast-preferred sequences.

In preparing the expression cassette, the various DNA fragments may be manipulated so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites or the like. For this purpose, in vitro mutagenesis, primer repair, restriction, annealing, resubstitutions, e.g., transitions and transversions, may be involved.

A number of promoters can be used in the practice of the embodiments. The promoters can be selected based on the desired outcome. The nucleic acids can be combined with constitutive, tissue-preferred, inducible or other promoters for expression in the host organism. Suitable constitutive promoters for use in a plant host cell include, for example, the core promoter of the Rsyn7 promoter and other constitutive promoters disclosed in WO 1999/43838 and U.S. Pat. No. 6,072,050; the core CaMV 35S promoter (Odell, et al., (1985) *Nature* 313:810-812); rice actin (McElroy, et al., (1990) *Plant Cell* 2:163-171); ubiquitin (Christensen, et al., (1989) *Plant Mol. Biol.* 12:619-632 and Christensen, et al., (1992) *Plant Mol. Biol.* 18:675-689); pEMU (Last, et al., (1991) *Theor. Appl. Genet.* 81:581-588); MAS (Velten, et al., (1984) *EMBO J.* 3:2723-2730); ALS promoter (U.S. Pat. No. 5,659,026) and the like. Other constitutive promoters include, for example, those discussed in U.S. Pat. Nos. 5,608,149; 5,608,144; 5,604,121; 5,569,597; 5,466,785; 5,399,680; 5,268,463; 5,608,142 and 6,177,611.

Depending on the desired outcome, it may be beneficial to express the gene from an inducible promoter. Of particular interest for regulating the expression of the nucleotide sequences of the embodiments in plants are wound-inducible promoters. Such wound-inducible promoters, may respond to damage caused by insect feeding, and include potato proteinase inhibitor (pin II) gene (Ryan, (1990) *Ann. Rev. Phytopath.* 28:425-449; Duan, et al., (1996) *Nature Biotechnology* 14:494-498); wun1 and wun2, U.S. Pat. No. 5,428,148; win1 and win2 (Stanford, et al., (1989) *Mol. Gen. Genet.* 215:200-208); systemin (McGurl, et al., (1992) *Science* 225:1570-1573); WIP1 (Rohmeier, et al., (1993) *Plant Mol. Biol.* 22:783-792; Eckelkamp, et al., (1993) *FEBS Letters* 323:73-76); MPI gene (Corderok, et al., (1994) *Plant J.* 6(2):141-150) and the like.

Additionally, pathogen-inducible promoters may be employed in the methods and nucleotide constructs of the embodiments. Such pathogen-inducible promoters include those from pathogenesis-related proteins (PR proteins), which are induced following infection by a pathogen; e.g., PR proteins, SAR proteins, beta-1,3-glucanase, chitinase, etc. See, for example, Redolfi, et al., (1983) *Neth. J. Plant Pathol.* 89:245-254; Uknes, et al., (1992) *Plant Cell* 4: 645-656 and Van Loon, (1985) *Plant Mol. Virol.* 4:111-116. See also, WO 1999/43819.

Of interest are promoters that are expressed locally at or near the site of pathogen infection. See, for example, Marineau, et al., (1987) *Plant Mol. Biol.* 9:335-342; Matton, et al., (1989) Molecular *Plant*-Microbe Interactions 2:325-331; Somsisch, et al., (1986) *Proc. Natl. Acad. Sci. USA* 83:2427-2430; Somsisch, et al., (1988) *Mol. Gen. Genet.* 2:93-98 and Yang, (1996) *Proc. Natl. Acad. Sci. USA* 93:14972-14977. See also, Chen, et al., (1996) *Plant J.* 10:955-966; Zhang, et al., (1994) *Proc. Natl. Acad. Sci. USA* 91:2507-2511; Warner, et al., (1993) *Plant J.* 3:191-201; Siebertz, et al., (1989) *Plant Cell* 1:961-968; U.S. Pat. No. 5,750,386 (nematode-inducible) and the references cited therein. Of particular interest is the inducible promoter for the maize PRms gene, whose expression is induced by the pathogen *Fusarium moniliforme* (see, for example, Cordero, et al., (1992) *Physiol. Mol. Plant Path.* 41:189-200).

Chemical-regulated promoters can be used to modulate the expression of a gene in a plant through the application of an exogenous chemical regulator. Depending upon the objective, the promoter may be a chemical-inducible promoter, where application of the chemical induces gene expression or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena, et al., (1991) *Proc. Natl. Acad. Sci. USA* 88:10421-10425 and McNellis, et al., (1998) *Plant J.* 14(2):247-257) and tetracycline-inducible and tetracycline-repressible promoters (see, for example, Gatz, et al., (1991) *Mol. Gen. Genet.* 227:229-237 and U.S. Pat. Nos. 5,814,618 and 5,789,156).

Tissue-preferred promoters can be utilized to target enhanced IPD101 polypeptide expression within a particular plant tissue. Tissue-preferred promoters include those discussed in Yamamoto, et al., (1997) *Plant J.* 12(2)255-265; Kawamata, et al., (1997) *Plant Cell Physiol.* 38(7):792-803; Hansen, et al., (1997) *Mol. Gen Genet.* 254(3):337-343; Russell, et al., (1997) *Transgenic Res.* 6(2): 157-168; Rinehart, et al., (1996) *Plant Physiol.* 112(3):1331-1341; Van Camp, et al., (1996) *Plant Physiol.* 112(2):525-535; Canevascini, et al., (1996) *Plant Physiol.* 112(2):513-524; Yamamoto, et al., (1994) *Plant Cell Physiol.* 35(5):773-778; Lam, (1994) *Results Probl. Cell Differ.* 20:181-196; Orozco, et al., (1993) *Plant Mol Biol.* 23(6):1129-1138; Matsuoka, et al., (1993) *Proc Natl. Acad. Sci. USA* 90(20):9586-9590 and Guevara-Garcia, et al., (1993) *Plant J.* 4(3):495-505. Such promoters can be modified, if necessary, for weak expression.

Leaf-preferred promoters are known in the art. See, for example, Yamamoto, et al., (1997) *Plant J.* 12(2):255-265; Kwon, et al., (1994) *Plant Physiol.* 105:357-67; Yamamoto, et al., (1994) *Plant Cell Physiol.* 35(5):773-778; Gotor, et al., (1993) *Plant J.* 3:509-18; Orozco, et al., (1993) *Plant Mol. Biol.* 23(6):1129-1138 and Matsuoka, et al., (1993) *Proc. Natl. Acad. Sci. USA* 90(20):9586-9590.

Root-preferred or root-specific promoters are known and can be selected from the many available from the literature or isolated de novo from various compatible species. See, for example, Hire, et al., (1992) *Plant Mol. Biol.* 20(2):207-218 (soybean root-specific glutamine synthetase gene); Keller and Baumgartner, (1991) *Plant Cell* 3(10):1051-1061 (root-specific control element in the GRP 1.8 gene of French bean); Sanger, et al., (1990) *Plant Mol. Biol.* 14(3):433-443 (root-specific promoter of the mannopine synthase (MAS) gene of *Agrobacterium tumefaciens*) and Miao, et al., (1991) *Plant Cell* 3(1):11-22 (full-length cDNA clone encoding cytosolic glutamine synthetase (GS), which is expressed in roots and root nodules of soybean). See also, Bogusz, et al., (1990) *Plant Cell* 2(7):633-641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi, (1991) describe their analysis of the promoters of the highly expressed rolC and rolD root-inducing genes of *Agrobacterium rhizogenes* (see, *Plant Science* (Limerick) 79(1):69-76). They concluded that enhancer and tissue-preferred DNA determinants are dissociated in those promoters. Teeri, et al., (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see, *EMBO J.* 8(2): 343-350). The TR1' gene fused to nptII (neomycin phosphotransferase II) showed similar characteristics. Additional root-preferred promoters include the VfENOD-GRP3 gene promoter (Kuster, et al., (1995) *Plant Mol. Biol.* 29(4):759-772) and rolB promoter (Capana, et al., (1994) *Plant Mol. Biol.* 25(4):681-691. See also, U.S. Pat. Nos. 5,837,876; 5,750,386; 5,633,363; 5,459,252; 5,401,836; 5,110,732 and 5,023,179. *Arabidopsis thaliana* root-preferred regulatory sequences are disclosed in US20130117883.

"Seed-preferred" promoters include both "seed-specific" promoters (those promoters active during seed development such as promoters of seed storage proteins) as well as "seed-germinating" promoters (those promoters active during seed germination). See, Thompson, et al., (1989) *BioEssays* 10:108. Such seed-preferred promoters include, but are not limited to, Cim1 (cytokinin-induced message); cZ19B1 (maize 19 kDa zein); and milps (myo-inositol-1-phosphate synthase) (see, U.S. Pat. No. 6,225,529). Gamma-zein and Glb-1 are endosperm-specific promoters. For dicots, seed-specific promoters include, but are not limited to, Kunitz trypsin inhibitor 3 (KTi3) (Jofuku and Goldberg, (1989) *Plant Cell* 1:1079-1101), bean β-phaseolin, napin, β-conglycinin, glycinin 1, soybean lectin, cruciferin, and the like. For monocots, seed-specific promoters include, but are not limited to, maize 15 kDa zein, 22 kDa zein, 27 kDa zein, g-zein, waxy, shrunken 1, shrunken 2, globulin 1, etc. See also, WO 2000/12733, where seed-preferred promoters from end1 and end2 genes are disclosed. In dicots, seed specific promoters include but are not limited to seed coat promoter from *Arabidopsis*, pBAN; and the early seed promoters from *Arabidopsis*, p26, p63, and p63tr (U.S. Pat. Nos. 7,294,760 and 7,847,153). A promoter that has "preferred" expression in a particular tissue is expressed in that tissue to a greater degree than in at least one other plant tissue. Some tissue-preferred promoters show expression almost exclusively in the particular tissue.

Where low level expression is desired, weak promoters will be used. Generally, the term "weak promoter" as used herein refers to a promoter that drives expression of a coding sequence at a low level. By low level expression at levels of between about 1/1000 transcripts to about 1/100,000 transcripts to about 1/500,000 transcripts is intended. Alternatively, it is recognized that the term "weak promoters" also encompasses promoters that drive expression in only a few cells and not in others to give a total low level of expression. Where a promoter drives expression at unacceptably high levels, portions of the promoter sequence can be deleted or modified to decrease expression levels.

Such weak constitutive promoters include, for example the core promoter of the Rsyn7 promoter (WO 1999/43838 and U.S. Pat. No. 6,072,050), the core 35S CaMV promoter, and the like. Other constitutive promoters include, for example, those disclosed in U.S. Pat. Nos. 5,608,149; 5,608,144; 5,604,121; 5,569,597; 5,466,785; 5,399,680; 5,268,463; 5,608,142 and 6,177,611.

The above list of promoters is not meant to be limiting. Any appropriate promoter can be used in the embodiments.

Generally, the expression cassette will comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones and 2,4-dichlorophenoxyacetate (2,4-D). Additional examples of suitable selectable marker genes include, but are not limited to, genes encoding resistance to chloramphenicol (Herrera Estrella, et al., (1983) *EMBO J.* 2:987-992); methotrexate (Herrera Estrella, et al., (1983) *Nature* 303:209-213 and Meijer, et al., (1991) *Plant Mol. Biol.* 16:807-820); streptomycin (Jones, et al., (1987) *Mol. Gen. Genet.* 210:86-91); spectinomycin (Bretagne-Sagnard, et al., (1996) *Transgenic Res.* 5:131-137); bleomycin (Hille, et al., (1990) *Plant Mol. Biol.* 7:171-176); sulfonamide (Guerineau, et al., (1990) *Plant Mol. Biol.* 15:127-136); bromoxynil (Stalker, et al., (1988) *Science* 242:419-423); glyphosate (Shaw, et al., (1986) *Science* 233:478-481 and U.S. patent application Ser. Nos. 10/004,357 and 10/427,692); phosphinothricin (DeBlock, et al., (1987) *EMBO J.* 6:2513-2518). See generally, Yarranton, (1992) *Curr. Opin. Biotech.* 3:506-511; Christopherson, et al., (1992) *Proc. Natl. Acad. Sci. USA* 89:6314-6318; Yao, et al., (1992) *Cell* 71:63-72; Reznikoff, (1992) *Mol. Microbiol.* 6:2419-2422; Barkley, et al., (1980) in *The Operon*, pp.

177-220; Hu, et al., (1987) *Cell* 48:555-566; Brown, et al., (1987) *Cell* 49:603-612; Figge, et al., (1988) *Cell* 52:713-722; Deuschle, et al., (1989) *Proc. Natl. Acad. Sci. USA* 86:5400-5404; Fuerst, et al., (1989) *Proc. Natl. Acad. Sci. USA* 86:2549-2553; Deuschle, et al., (1990) *Science* 248:480-483; Gossen, (1993) Ph.D. Thesis, University of Heidelberg; Reines, et al., (1993) *Proc. Natl. Acad. Sci. USA* 90:1917-1921; Labow, et al., (1990) *Mol. Cell. Biol.* 10:3343-3356; Zambretti, et al., (1992) *Proc. Natl. Acad. Sci. USA* 89:3952-3956; Baim, et al., (1991) *Proc. Natl. Acad. Sci. USA* 88:5072-5076; Wyborski, et al., (1991) *Nucleic Acids Res.* 19:4647-4653; Hillenand-Wissman, (1989) *Topics Mol. Struc. Biol.* 10:143-162; Degenkolb, et al., (1991) *Antimicrob. Agents Chemother.* 35:1591-1595; Kleinschnidt, et al., (1988) *Biochemistry* 27:1094-1104; Bonin, (1993) Ph.D. Thesis, University of Heidelberg; Gossen, et al., (1992) *Proc. Natl. Acad. Sci. USA* 89:5547-5551; Oliva, et al., (1992) *Antimicrob. Agents Chemother.* 36:913-919; Hlavka, et al., (1985) *Handbook of Experimental Pharmacology*, Vol. 78 (Springer-Verlag, Berlin) and Gill, et al., (1988) *Nature* 334:721-724.

The above list of selectable marker genes is not meant to be limiting. Any selectable marker gene can be used in the embodiments.

Plant Transformation

The methods of the embodiments involve introducing a polypeptide or polynucleotide into a plant. "Introducing" is as used herein means presenting to the plant the polynucleotide or polypeptide in such a manner that the sequence gains access to the interior of a cell of the plant. The methods of the embodiments do not depend on a particular method for introducing a polynucleotide or polypeptide into a plant, only that the polynucleotide(s) or polypeptide(s) gains access to the interior of at least one cell of the plant. Methods for introducing polynucleotide(s) or polypeptide(s) into plants are known in the art including, but not limited to, stable transformation methods, transient transformation methods, and virus-mediated methods.

"Stable transformation" as used herein means that the nucleotide construct introduced into a plant integrates into the genome of the plant and is capable of being inherited by the progeny thereof. "Transient transformation" as used herein means that a polynucleotide is introduced into the plant and does not integrate into the genome of the plant or a polypeptide is introduced into a plant. "Plant" as used herein refers to whole plants, plant organs (e.g., leaves, stems, roots, etc.), seeds, plant cells, propagules, embryos and progeny of the same. *Plant* cells can be differentiated or undifferentiated (e.g. callus, suspension culture cells, protoplasts, leaf cells, root cells, phloem cells and pollen).

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway, et al., (1986) *Biotechniques* 4:320-334), electroporation (Riggs, et al., (1986) *Proc. Natl. Acad. Sci. USA* 83:5602-5606), *Agrobacterium*-mediated transformation (U.S. Pat. Nos. 5,563,055 and 5,981,840), direct gene transfer (Paszkowski, et al., (1984) *EMBO J.* 3:2717-2722) and ballistic particle acceleration (see, for example, U.S. Pat. Nos. 4,945,050; 5,879,918; 5,886,244 and 5,932,782; Tomes, et al., (1995) in *Plant Cell, Tissue, and Organ Culture: Fundamental Methods*, ed. Gamborg and Phillips, (Springer-Verlag, Berlin) and McCabe, et al., (1988) *Biotechnology* 6:923-926) and Lec1 transformation (WO 00/28058). For potato transformation see, Tu, et al., (1998) *Plant* Molecular Biology 37:829-838 and Chong, et al., (2000) *Transgenic Research* 9:71-78. Additional transformation procedures can be found in Weissinger, et al., (1988) *Ann. Rev. Genet.* 22:421-477; Sanford, et al., (1987) *Particulate Science and Technology* 5:27-37 (onion); Christou, et al., (1988) *Plant Physiol.* 87:671-674 (soybean); McCabe, et al., (1988) *Bio/Technology* 6:923-926 (soybean); Finer and McMullen, (1991) *In Vitro Cell Dev. Biol.* 27P:175-182 (soybean); Singh, et al., (1998) *Theor. Appl. Genet.* 96:319-324 (soybean); Datta, et al., (1990) *Biotechnology* 8:736-740 (rice); Klein, et al., (1988) *Proc. Natl. Acad. Sci. USA* 85:4305-4309 (maize); Klein, et al., (1988) *Biotechnology* 6:559-563 (maize); U.S. Pat. Nos. 5,240,855; 5,322,783 and 5,324,646; Klein, et al., (1988) *Plant Physiol.* 91:440-444 (maize); Fromm, et al., (1990) *Biotechnology* 8:833-839 (maize); Hooykaas-Van Slogteren, et al., (1984) *Nature (London)* 311:763-764; U.S. Pat. No. 5,736,369 (cereals); Bytebier, et al., (1987) *Proc. Natl. Acad. Sci. USA* 84:5345-5349 (Liliaceae); De Wet, et al., (1985) in *The Experimental Manipulation of Ovule Tissues*, ed. Chapman, et al., (Longman, N.Y.), pp. 197-209 (pollen); Kaeppler, et al., (1990) *Plant Cell Reports* 9:415-418 and Kaeppler, et al., (1992) *Theor. Appl. Genet.* 84:560-566 (whisker-mediated transformation); D'Halluin, et al., (1992) *Plant Cell* 4:1495-1505 (electroporation); Li, et al., (1993) *Plant Cell Reports* 12:250-255 and Christou and Ford, (1995) *Annals of Botany* 75:407-413 (rice); Osjoda, et al., (1996) *Nature Biotechnology* 14:745-750 (maize via *Agrobacterium tumefaciens*).

In specific embodiments, the sequences of the embodiments can be provided to a plant using a variety of transient transformation methods. Such transient transformation methods include, but are not limited to, the introduction of the IPD101 polynucleotide or variants and fragments thereof directly into the plant or the introduction of the IPD101 polypeptide transcript into the plant. Such methods include, for example, microinjection or particle bombardment. See, for example, Crossway, et al., (1986) *Mol Gen. Genet.* 202:179-185; Nomura, et al., (1986) *Plant Sci.* 44:53-58; Hepler, et al., (1994) *Proc. Natl. Acad. Sci.* 91:2176-2180 and Hush, et al., (1994) *The Journal of Cell Science* 107:775-784. Alternatively, the IPD101 polynucleotide can be transiently transformed into the plant using techniques known in the art. Such techniques include viral vector system and the precipitation of the polynucleotide in a manner that precludes subsequent release of the DNA. Thus, transcription from the particle-bound DNA can occur, but the frequency with which it is released to become integrated into the genome is greatly reduced. Such methods include the use of particles coated with polyethylimine (PEI; Sigma #P3143).

Methods are known in the art for the targeted insertion of a polynucleotide at a specific location in the plant genome. In one embodiment, the insertion of the polynucleotide at a desired genomic location is achieved using a site-specific recombination system. See, for example, WO 1999/25821, WO 1999/25854, WO 1999/25840, WO 1999/25855 and WO 1999/25853. Briefly, the polynucleotide of the embodiments can be contained in transfer cassette flanked by two non-identical recombination sites. The transfer cassette is introduced into a plant have stably incorporated into its genome a target site which is flanked by two non-identical recombination sites that correspond to the sites of the transfer cassette. An appropriate recombinase is provided and the transfer cassette is integrated at the target site. The polynucleotide of interest is thereby integrated at a specific chromosomal position in the plant genome.

Plant transformation vectors may be comprised of one or more DNA vectors needed for achieving plant transformation. For example, it is a common practice in the art to utilize plant transformation vectors that are comprised of more than one contiguous DNA segment. These vectors are often referred to in the art as "binary vectors". Binary vectors as well as vectors with helper plasmids are most often used for *Agrobacterium*-mediated transformation, where the size and complexity of DNA segments needed to achieve efficient transformation is quite large, and it is advantageous to separate functions onto separate DNA molecules. Binary vectors typically contain a plasmid vector that contains the cis-acting sequences required for T-DNA transfer (such as left border and right border), a selectable marker that is engineered to be capable of expression in a plant cell, and a "gene of interest" (a gene engineered to be capable of expression in a plant cell for which generation of transgenic plants is desired). Also present on this plasmid vector are sequences required for bacterial replication. The cis-acting sequences are arranged in a fashion to allow efficient transfer into plant cells and expression therein. For example, the selectable marker gene and the pesticidal gene are located between the left and right borders. Often a second plasmid vector contains the trans-acting factors that mediate T-DNA transfer from *Agrobacterium* to plant cells. This plasmid often contains the virulence functions (Vir genes) that allow infection of plant cells by *Agrobacterium*, and transfer of DNA by cleavage at border sequences and vir-mediated DNA transfer, as is understood in the art (Hellens and Mullineaux, (2000) *Trends in Plant Science* 5:446-451). Several types of *Agrobacterium* strains (e.g. LBA4404, GV3101, EHA101, EHA105, etc.) can be used for plant transformation. The second plasmid vector is not necessary for transforming the plants by other methods such as microprojection, microinjection, electroporation, polyethylene glycol, etc.

In general, plant transformation methods involve transferring heterologous DNA into target plant cells (e.g., immature or mature embryos, suspension cultures, undifferentiated callus, protoplasts, etc.), followed by applying a maximum threshold level of appropriate selection (depending on the selectable marker gene) to recover the transformed plant cells from a group of untransformed cell mass. Following integration of heterologous foreign DNA into plant cells, one then applies a maximum threshold level of appropriate selection in the medium to kill the untransformed cells and separate and proliferate the putatively transformed cells that survive from this selection treatment by transferring regularly to a fresh medium. By continuous passage and challenge with appropriate selection, one identifies and proliferates the cells that are transformed with the plasmid vector. Molecular and biochemical methods can then be used to confirm the presence of the integrated heterologous gene of interest into the genome of the transgenic plant.

Explants are typically transferred to a fresh supply of the same medium and cultured routinely. Subsequently, the transformed cells are differentiated into shoots after placing on regeneration medium supplemented with a maximum threshold level of selecting agent. The shoots are then transferred to a selective rooting medium for recovering rooted shoot or plantlet. The transgenic plantlet then grows into a mature plant and produces fertile seeds (e.g., Hiei, et al., (1994) *The Plant Journal* 6:271-282; Ishida, et al., (1996) *Nature Biotechnology* 14:745-750). Explants are typically transferred to a fresh supply of the same medium and cultured routinely. A general description of the techniques and methods for generating transgenic plants are found in Ayres and Park, (1994) *Critical Reviews in Plant Science* 13:219-239 and Bommineni and Jauhar, (1997) *Maydica* 42:107-120. Since the transformed material contains many cells; both transformed and non-transformed cells are present in any piece of subjected target callus or tissue or group of cells. The ability to kill non-transformed cells and allow transformed cells to proliferate results in transformed plant cultures. Often, the ability to remove non-transformed cells is a limitation to rapid recovery of transformed plant cells and successful generation of transgenic plants.

The cells that have been transformed may be grown into plants in accordance with conventional ways. See, for example, McCormick, et al., (1986) *Plant Cell Reports* 5:81-84. These plants may then be grown, and either pollinated with the same transformed strain or different strains, and the resulting hybrid having constitutive or inducible expression of the desired phenotypic characteristic identified. Two or more generations may be grown to ensure that expression of the desired phenotypic characteristic is stably maintained and inherited and then seeds harvested to ensure that expression of the desired phenotypic characteristic has been achieved.

The nucleotide sequences of the embodiments may be provided to the plant by contacting the plant with a virus or viral nucleic acids. Generally, such methods involve incorporating the nucleotide construct of interest within a viral DNA or RNA molecule. It is recognized that the recombinant proteins of the embodiments may be initially synthesized as part of a viral polyprotein, which later may be processed by proteolysis in vivo or in vitro to produce the desired IPD101 polypeptide. It is also recognized that such a viral polyprotein, comprising at least a portion of the amino acid sequence of an IPD101 polypeptide of the embodiments, may have the desired pesticidal activity. Such viral polyproteins and the nucleotide sequences that encode for them are encompassed by the embodiments. Methods for providing plants with nucleotide constructs and producing the encoded proteins in the plants, which involve viral DNA or RNA molecules, are known in the art. See, for example, U.S. Pat. Nos. 5,889,191; 5,889,190; 5,866,785; 5,589,367 and 5,316,931.

Methods for transformation of chloroplasts are known in the art. See, for example, Svab, et al., (1990) *Proc. Natl. Acad. Sci*. USA 87:8526-8530; Svab and Maliga, (1993) *Proc. Natl. Acad. Sci*. USA 90:913-917; Svab and Maliga, (1993) *EMBO J*. 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride, et al., (1994) *Proc. Natl. Acad. Sci*. USA 91:7301-7305.

The embodiments further relate to plant-propagating material of a transformed plant of the embodiments including, but not limited to, seeds, tubers, corms, bulbs, leaves and cuttings of roots and shoots.

The embodiments may be used for transformation of any plant species, including, but not limited to, monocots and dicots. Examples of plants of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor,*

Sorghum vulgare), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (Macadamia *integrifolia*), almond (*Prunus amygdalus*), sugar beets (*Beta vulgaris*), sugarcane (*Saccharum* spp.), oats, barley, vegetables ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and *chrysanthemum*. Conifers that may be employed in practicing the embodiments include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Plants of the embodiments include crop plants (for example, corn, alfalfa, sunflower, *Brassica*, soybean, cotton, safflower, peanut, sorghum, wheat, millet, tobacco, etc.), such as corn and soybean plants.

Turf grasses include, but are not limited to: annual bluegrass (*Poa annua*); annual ryegrass (*Lolium multiflorum*); Canada bluegrass (*Poa compressa*); Chewing's fescue (*Festuca rubra*); colonial bentgrass (*Agrostis tenuis*); creeping bentgrass (*Agrostis palustris*); crested wheatgrass (*Agropyron desertorum*); fairway wheatgrass (*Agropyron cristatum*); hard fescue (*Festuca longifolia*); Kentucky bluegrass (*Poa pratensis*); orchardgrass (*Dactylis glomerata*); perennial ryegrass (*Lolium perenne*); red fescue (*Festuca rubra*); redtop (*Agrostis alba*); rough bluegrass (*Poa trivialis*); sheep fescue (*Festuca ovina*); smooth bromegrass (*Bromus inermis*); tall fescue (*Festuca arundinacea*); timothy (*Phleum pratense*); velvet bentgrass (*Agrostis canina*); weeping alkaligrass (*Puccinellia distans*); western wheatgrass (*Agropyron smithii*); Bermuda grass (*Cynodon* spp.); St. Augustine grass (*Stenotaphrum secundatum*); *zoysia* grass (*Zoysia* spp.); Bahia grass (*Paspalum notatum*); carpet grass (*Axonopus affinis*); centipede grass (*Eremochloa ophiuroides*); kikuyu grass (*Pennisetum clandesinum*); seashore paspalum (*Paspalum vaginatum*); blue gramma (*Bouteloua gracilis*); buffalo grass (*Buchloe dactyloids*); sideoats gramma (*Bouteloua curtipendula*).

Plants of interest include grain plants that provide seeds of interest, oil-seed plants, and leguminous plants. Seeds of interest include grain seeds, such as corn, wheat, barley, rice, sorghum, rye, millet, etc. Oil-seed plants include cotton, soybean, safflower, sunflower, *Brassica*, maize, alfalfa, palm, coconut, flax, castor, olive, etc. Leguminous plants include beans and peas. Beans include guar, locust bean, fenugreek, soybean, garden beans, cowpea, mung bean, lima bean, fava bean, lentils, chickpea, etc.

Following introduction of heterologous foreign DNA into plant cells, the transformation or integration of heterologous gene in the plant genome is confirmed by various methods such as analysis of nucleic acids, proteins and metabolites associated with the integrated gene.

PCR analysis is a rapid method to screen transformed cells, tissue or shoots for the presence of incorporated gene at the earlier stage before transplanting into the soil (Sambrook and Russell, (2001) Molecular Cloning: A Laboratory Manual. Cold Spring Harbor Laboratory Press, Cold Spring Harbor, N.Y.). PCR is carried out using oligonucleotide primers specific to the gene of interest or *Agrobacterium* vector background, etc.

Plant transformation may be confirmed by Southern blot analysis of genomic DNA (Sambrook and Russell, (2001) supra). In Northern blot analysis, RNA is isolated from specific tissues of transformant, fractionated in a formaldehyde agarose gel, and blotted onto a nylon filter according to standard procedures that are routinely used in the art (Sambrook and Russell, (2001) supra). Expression of RNA encoded by the pesticidal gene is then tested by hybridizing the filter to a radioactive probe derived from a pesticidal gene, by methods known in the art (Sambrook and Russell, (2001) supra). Western blot, biochemical assays and the like may be carried out on the transgenic plants to confirm the presence of protein encoded by the pesticidal gene by standard procedures (Sambrook and Russell, 2001, supra) using antibodies that bind to one or more epitopes present on the IPD101 polypeptide.

Methods to Introduce Genome Editing Technologies into Plants

In some embodiments, the disclosed IPD101 polynucleotide compositions can be introduced into the genome of a plant using genome editing technologies, or previously introduced IPD101 polynucleotides in the genome of a plant may be edited using genome editing technologies. For example, the disclosed polynucleotides can be introducted into a desired location in the genome of a plant through the use of double-stranded break technologies such as TALENs, meganucleases, zinc finger nucleases, CRISPR-Cas, and the like. For example, the disclosed polynucleotides can be introduced into a desired location in a genome using a CRISPR-Cas system, for the purpose of site-specific insertion. The desired location in a plant genome can be any desired target site for insertion, such as a genomic region amenable for breeding or may be a target site located in a genomic window with an existing trait of interest. Existing traits of interest could be either an endogenous trait or a previously introduced trait.

In some embodiments, where the disclosed IPD101 polynucleotide has previously been introduced into a genome, genome editing technologies may be used to alter or modify the introduced polynucleotide sequence. Site specific modifications that can be introduced into the disclosed IPD101 polynucleotide compositions include those produced using any method for introducing site specific modification, including, but not limited to, through the use of gene repair oligonucleotides (e.g. US Publication 2013/0019349), or through the use of double-stranded break technologies such as TALENs, meganucleases, zinc finger nucleases, CRISPR- Cas, and the like. Such technologies can be used to modify the previously introduced polynucleotide through the insertion, deletion or substitution of nucleotides within the introduced polynucleotide. Alternatively, double-stranded break technologies can be used to add additional nucleotide sequences to the introduced polynucleotide. Additional sequences that may be added include, additional expression elements, such as enhancer and promoter sequences. In another embodiment, genome editing technologies may be used to position additional insecticidally-active proteins in close proximity to the disclosed IPD101 polynucleotide compositions disclosed herein within the genome of a plant, in order to generate molecular stacks of insecticidally-active proteins.

An "altered target site," "altered target sequence." "modified target site," and "modified target sequence" are used interchangeably herein and refer to a target sequence as disclosed herein that comprises at least one alteration when compared to non-altered target sequence. Such "alterations" include, for example: (i) replacement of at least one nucleotide, (ii) a deletion of at least one nucleotide, (iii) an insertion of at least one nucleotide, or (iv) any combination of (i)-(iii).

Stacking of Traits in Transgenic Plant

Transgenic plants may comprise a stack of one or more insecticidal polynucleotides disclosed herein with one or more additional polynucleotides resulting in the production or suppression of multiple polypeptide sequences. Transgenic plants comprising stacks of polynucleotide sequences can be obtained by either or both of traditional breeding methods or through genetic engineering methods. These methods include, but are not limited to, breeding individual lines each comprising a polynucleotide of interest, transforming a transgenic plant comprising a gene disclosed herein with a subsequent gene and co-transformation of genes into a single plant cell. As used herein, the term "stacked" includes having the multiple traits present in the same plant (i.e., both traits are incorporated into the nuclear genome, one trait is incorporated into the nuclear genome and one trait is incorporated into the genome of a plastid or both traits are incorporated into the genome of a plastid). In one non-limiting example, "stacked traits" comprise a molecular stack where the sequences are physically adjacent to each other. A trait, as used herein, refers to the phenotype derived from a particular sequence or groups of sequences. Co-transformation of genes can be carried out using single transformation vectors comprising multiple genes or genes carried separately on multiple vectors. If the sequences are stacked by genetically transforming the plants, the polynucleotide sequences of interest can be combined at any time and in any order. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO 1999/25821, WO 1999/25854, WO 1999/25840, WO 1999/25855 and WO 1999/25853, all of which are herein incorporated by reference.

In some embodiments, one or more of the polynucleotides encoding the IPD101 polypeptide(s) disclosed herein, alone or stacked with one or more additional insect resistance traits can be stacked with one or more additional input traits (e.g., herbicide resistance, fungal resistance, virus resistance, stress tolerance, disease resistance, male sterility, stalk strength, and the like) or output traits (e.g., increased yield, modified starches, improved oil profile, balanced amino acids, high lysine or methionine, increased digestibility, improved fiber quality, drought resistance, and the like). Thus, the polynucleotide embodiments can be used to provide a complete agronomic package of improved crop quality with the ability to flexibly and cost effectively control any number of agronomic pests.

Transgenes useful for stacking include but are not limited to: transgenes that confer resistance to a herbicide; transgenes that confer or contribute to an altered grain characteristic; genes that control male-sterility; genes that create a site for site specific dna integration; genes that affect abiotic stress resistance; genes that confer increased yield genes that confer plant digestibility; and transgenes that confer resistance to insects or disease.

Examples of transgenes that confer resistance to insects include genes encoding a *Bacillus thuringiensis* protein, a derivative thereof or a synthetic polypeptide modeled thereon. See, for example, Geiser, et al., (1986) *Gene* 48:109, who disclose the cloning and nucleotide sequence of a Bt delta-endotoxin gene. Moreover, DNA molecules encoding delta-endotoxin genes can be purchased from American Type Culture Collection (Rockville, Md.), for example, under ATCC® Accession Numbers 40098, 67136, 31995 and 31998. Other non-limiting examples of *Bacillus thuringiensis* transgenes being genetically engineered are given in the following patents and patent applications: U.S. Pat. Nos. 5,188,960; 5,689,052; 5,880,275; 5,986,177; 6,023,013, 6,060,594, 6,063,597, 6,077,824, 6,620,988, 6,642,030, 6,713,259, 6,893,826, 7,105,332; 7,179,965, 7,208,474; 7,227,056, 7,288,643, 7,323,556, 7,329,736, 7,449,552, 7,468,278, 7,510,878, 7,521,235, 7,544,862, 7,605,304, 7,696,412, 7,629,504, 7,705,216, 7,772,465, 7,790,846, 7,858,849 and WO 1991/14778; WO 1999/31248; WO 2001/12731; WO 1999/24581 and WO 1997/40162.

Genes encoding pesticidal proteins may also be stacked including but are not limited to: insecticidal proteins from *Pseudomonas* sp. such as PSEEN3174 (Monalysin, (2011) *PLoS Pathogens,* 7:1-13), from *Pseudomonas protegens* strain CHA0 and Pf-5 (previously *fluorescens*) (Pechy-Tarr, (2008) *Environmental Microbiology* 10:2368-2386: GenBank Accession No. EU400157); from *Pseudomonas taiwanensis* (Liu, et al., (2010) *J. Agric. Food Chem.* 58:12343-12349) and from *Pseudomonas pseudoalcaligenes* (Zhang, et al., (2009) *Annals of Microbiology* 59:45-50 and Li, et al., (2007) *Plant Cell Tiss. Organ Cult.* 89:159-168); insecticidal proteins from *Photorhabdus* sp. and *Xenorhabdus* sp. (Hinchliffe, et al., (2010) *The Open Toxinology Journal* 3:101-118 and Morgan, et al., (2001) *Applied and Envir. Micro.* 67:2062-2069), U.S. Pat. Nos. 6,048,838, and 6,379, 946; a PIP-1 polypeptide of US Patent Application Publication Number US20140007292; an AfIP-1A and/or AfIP-1B polypeptide of US Patent Application Publication Number US20140033361; a PHI-4 polypeptide of US Patent Application Publication Number US20140274885 and US20160040184; a PIP-47 polypeptide of US Patent Application Publication Number US20160186204, a PIP-72 polypeptide of US Patent Application Publication Number US20160366891; a PtIP-50 polypeptide and a PtIP-65 polypeptide of US Patent Application Publication Number 20170166921; a PtIP-83 polypeptide of US Patent Application Publication Number 20160347799; a PtIP-96 polypeptide of US Patent Application Publication Number 20170233440; an IPD079 polypeptide of U.S. Ser. No. 62/201,977; an IPD082 polypeptide of U.S. Ser. No. 62/269,482, and 6-endotoxins including, but not limited to, the Cry1, Cry2, Cry3, Cry4, Cry5, Cry6, Cry7, Cry8, Cry9, Cry10, Cry11, Cry12, Cry13, Cry14, Cry15, Cry16, Cry17, Cry18, Cry19, Cry20, Cry21, Cry22, Cry23, Cry24, Cry25, Cry26, Cry27, Cry 28, Cry 29, Cry 30, Cry31, Cry32, Cry33, Cry34, Cry35, Cry36, Cry37, Cry38, Cry39, Cry40, Cry41, Cry42, Cry43, Cry44, Cry45, Cry 46, Cry47, Cry49, Cry50, Cry51, Cry52, Cry53, Cry 54, Cry55, Cry56, Cry57, Cry58, Cry59, Cry60, Cry61, Cry62, Cry63, Cry64, Cry65, Cry66, Cry67, Cry68, Cry69, Cry70, Cry71, and Cry 72 classes of δ-endotoxin genes and the *B. thuringiensis* cytolytic Cyt1 and Cyt2 genes. Members of these classes of *B. thuringiensis* insecticidal proteins well known to one skilled in the art (see, Crickmore, et al., "*Bacillus thuringiensis* toxin nomenclature" (2011), at lifesci.sussex.ac.uk/home/Neil_Crickmore/Bt/ which can be accessed on the world-wide web using the "www" prefix).

Examples of δ-endotoxins also include but are not limited to Cry1A proteins of U.S. Pat. Nos. 5,880,275 and 7,858,849; a DIG-3 or DIG-11 toxin (N-terminal deletion of α-helix 1 and/or α-helix 2 variants of Cry proteins such as Cry1A) of U.S. Pat. Nos. 8,304,604 and 8,304,605, Cry1B of U.S. patent application Ser. No. 10/525,318; Cry1C of U.S. Pat. No. 6,033,874; Cry1F of U.S. Pat. Nos. 5,188,960, 6,218,188; Cry1A/F chimeras of U.S. Pat. Nos. 7,070,982; 6,962,705 and 6,713,063); a Cry2 protein such as Cry2Ab protein of U.S. Pat. No. 7,064,249); a Cry3A protein including but not limited to an engineered hybrid insecticidal protein (eHIP) created by fusing unique combinations of variable regions and conserved blocks of at least two different Cry proteins (US Patent Application Publication Number 2010/0017914); a Cry4 protein; a Cry5 protein; a Cry6 protein; Cry8 proteins of U.S. Pat. Nos. 7,329,736, 7,449,552, 7,803,943, 7,476,781, 7,105,332, 7,378,499 and 7,462,760; a Cry9 protein such as such as members of the Cry9A, Cry9B, Cry9C, Cry9D, Cry9E, and Cry9F families; a Cry15 protein of Naimov, et al., (2008) *Applied and Environmental Microbiology* 74:7145-7151; a Cry22, a Cry34Ab1 protein of U.S. Pat. Nos. 6,127,180, 6,624,145 and 6,340,593; a CryET33 and CryET34 protein of U.S. Pat. Nos. 6,248,535, 6,326,351, 6,399,330, 6,949,626, 7,385,107 and 7,504,229; a CryET33 and CryET34 homologs of US Patent Publication Number 2006/0191034, 2012/0278954, and PCT Publication Number WO 2012/139004; a Cry35Ab1 protein of U.S. Pat. Nos. 6,083,499, 6,548,291 and 6,340,593; a Cry46 protein, a Cry 51 protein, a Cry binary toxin; a TIC901 or related toxin; TIC807 of US 2008/0295207; ET29, ET37, TIC809, TIC810, TIC812, TIC127, TIC128 of PCT US 2006/033867; AXMI-027, AXMI-036, and AXMI-038 of U.S. Pat. No. 8,236,757; AXMI-031, AXMI-039, AXMI-040, AXMI-049 of U.S. Pat. No. 7,923,602; AXMI-018, AXMI-020, and AXMI-021 of WO 2006/083891; AXMI-010 of WO 2005/038032; AXMI-003 of WO 2005/021585; AXMI-008 of US 2004/0250311; AXMI-006 of US 2004/0216186; AXMI-007 of US 2004/0210965; AXMI-009 of US 2004/0210964; AXMI-014 of US 2004/0197917; AXMI-004 of US 2004/0197916; AXMI-028 and AXMI-029 of WO 2006/119457; AXMI-007, AXMI-008, AXMI-0080rf2, AXMI-009, AXMI-014 and AXMI-004 of WO 2004/074462; AXMI-150 of U.S. Pat. No. 8,084,416; AXMI-205 of US20110023184; AXMI-011, AXMI-012, AXMI-013, AXMI-015, AXMI-019, AXMI-044, AXMI-037, AXMI-043, AXMI-033, AXMI-034, AXMI-022, AXMI-023, AXMI-041, AXMI-063, and AXMI-064 of US 2011/0263488; AXMI-R1 and related proteins of US 2010/0197592; AXMI221Z, AXMI222z, AXMI223z, AXMI224z and AXMI225z of WO 2011/103248; AXMI218, AXMI219, AXMI220, AXMI226, AXMI227, AXMI228, AXMI229, AXMI230, and AXMI231 of WO11/103247; AXMI-115, AXMI-113, AXMI-005, AXMI-163 and AXMI-184 of U.S. Pat. No. 8,334,431; AXMI-001, AXMI-002, AXMI-030, AXMI-035, and AXMI-045 of US 2010/0298211; AXMI-066 and AXMI-076 of US2009/0144852; AXMI128, AXMI130, AXMI131, AXMI133, AXMI140, AXMI141, AXMI142, AXMI143, AXMI144, AXMI146, AXMI148, AXMI149, AXMI152, AXMI153, AXMI154, AXMI155, AXMI156, AXMI157, AXMI158, AXMI162, AXMI165, AXMI166, AXMI167, AXMI168, AXMI169, AXMI170, AXMI171, AXMI172, AXMI173, AXMI174, AXMI175, AXMI176, AXMI177, AXMI178, AXMI179, AXMI180, AXMI181, AXMI182, AXMI185, AXMI186, AXMI187, AXMI188, AXMI189 of U.S. Pat. No. 8,318,900; AXMI079, AXMI080, AXMI081, AXMI082, AXMI091, AXMI092, AXMI096, AXMI097, AXMI098, AXMI099, AXMI100, AXMI101, AXMI102, AXMI103, AXMI104, AXMI107, AXMI108, AXMI109, AXMI110, AXMI111, AXMI112, AXMI114, AXMI116, AXMI117, AXMI118, AXMI119, AXMI120, AXMI121, AXMI122, AXMI123, AXMI124, AXMI1257, AXMI1268, AXMI127, AXMI129, AXMI164, AXMI151, AXMI161, AXMI183, AXMI132, AXMI138, AXMI137 of US 2010/0005543; and Cry proteins such as Cry1A and Cry3A having modified proteolytic sites of U.S. Pat. No. 8,319,019; and a Cry1Ac, Cry2Aa and Cry1Ca toxin protein from *Bacillus thuringiensis* strain VBTS 2528 of US Patent Application Publication Number 2011/0064710. Other Cry proteins are well known to one skilled in the art (see, Crickmore, et al., "*Bacillus thuringiensis* toxin nomenclature" (2011), at lifesci.sussex.ac.uk/home/Neil_Crickmore/Bt/ which can be accessed on the world-wide web using the "www" prefix). The insecticidal activity of Cry proteins is well known to one skilled in the art (for review, see, van Frannkenhuyzen, (2009) *J. Invert. Path.* 101:1-16). The use of Cry proteins as transgenic plant traits is well known to one skilled in the art and Cry-transgenic plants including but not limited to Cry1Ac, Cry1Ac+ Cry2Ab, Cry1Ab, Cry1A.105, Cry1F, Cry1Fa2, Cry1F+ Cry1Ac, Cry2Ab, Cry3A, mCry3A, Cry3Bb1, Cry34Ab1, Cry35Ab1, Vip3A, mCry3A, Cry9c and CBI-Bt have received regulatory approval (see, Sanahuja, (2011) *Plant Biotech Journal* 9:283-300 and the CERA (2010) GM Crop Database Center for Environmental Risk Assessment (CERA), ILSI Research Foundation, Washington D.C. at cera-gmc.org/index.php?action=gm_crop_database which can be accessed on the world-wide web using the "www" prefix). More than one pesticidal proteins well known to one skilled in the art can also be expressed in plants such as Vip3Ab & Cry1Fa (US2012/0317682), Cry1BE & Cry1F (US2012/0311746), Cry1CA & Cry1AB (US2012/0311745), Cry1F & CryCa (US2012/0317681), Cry1DA & Cry1BE (US2012/0331590), Cry1DA & Cry1Fa (US2012/0331589), Cry1AB & Cry1BE (US2012/0324606), and Cry1Fa & Cry2Aa, Cry1I or Cry1E (US2012/0324605). Pesticidal proteins also include insecticidal lipases including lipid acyl hydrolases of U.S. Pat. No. 7,491,869, and cholesterol oxidases such as from *Streptomyces* (Purcell et al.

(1993) *Biochem Biophys Res Commun* 15:1406-1413). Pesticidal proteins also include VIP (vegetative insecticidal proteins) toxins of U.S. Pat. Nos. 5,877,012, 6,107,279, 6,137,033, 7,244,820, 7,615,686, and 8,237,020, and the like. Other VIP proteins are well known to one skilled in the art (see, lifesci.sussex.ac.uk/home/Neil_Crickmore/Bt/vip.html which can be accessed on the world-wide web using the "www" prefix). Pesticidal proteins also include toxin complex (TC) proteins, obtainable from organisms such as *Xenorhabdus, Photorhabdus* and *Paenibacillus* (see, U.S. Pat. Nos. 7,491,698 and 8,084,418). Some TC proteins have "stand alone" insecticidal activity and other TC proteins enhance the activity of the stand-alone toxins produced by the same given organism. The toxicity of a "stand-alone" TC protein (from *Photorhabdus, Xenorhabdus* or *Paenibacillus*, for example) can be enhanced by one or more TC protein "potentiators" derived from a source organism of a different genus. There are three main types of TC proteins. As referred to herein, Class A proteins ("Protein A") are stand-alone toxins. Class B proteins ("Protein B") and Class C proteins ("Protein C") enhance the toxicity of Class A proteins. Examples of Class A proteins are TcbA, TcdA, XptA1 and XptA2. Examples of Class B proteins are TcaC, TcdB, XptB1Xb and XptC1Wi. Examples of Class C proteins are TccC, XptC1Xb and XptB1Wi. Pesticidal proteins also include spider, snake and scorpion venom proteins. Examples of spider venom peptides include but are not limited to lycotoxin-1 peptides and mutants thereof (U.S. Pat. No. 8,334,366).

Further transgenes that confer resistance to insects may down-regulation of expression of target genes in insect pest species by interfering ribonucleic acid (RNA) molecules through RNA interference. RNA interference refers to the process of sequence-specific post-transcriptional gene silencing in animals mediated by short interfering RNAs (siRNAs) (Fire, et al., (1998) *Nature* 391:806). RNAi transgenes may include but are not limited to expression of dsRNA, siRNA, miRNA, iRNA, antisense RNA, or sense RNA molecules that down-regulate expression of target genes in insect pests. PCT Publication WO 2007/074405 describes methods of inhibiting expression of target genes in invertebrate pests including Colorado potato beetle. PCT Publication WO 2005/110068 describes methods of inhibiting expression of target genes in invertebrate pests including in particular Western corn rootworm as a means to control insect infestation. Furthermore, PCT Publication WO 2009/091864 describes compositions and methods for the suppression of target genes from insect pest species including pests from the *Lygus* genus.

RNAi transgenes are provided for targeting the vacuolar ATPase H subunit, useful for controlling a coleopteran pest population and infestation as described in US Patent Application Publication 2012/0198586. PCT Publication WO 2012/055982 describes ribonucleic acid (RNA or double stranded RNA) that inhibits or down regulates the expression of a target gene that encodes: an insect ribosomal protein such as the ribosomal protein L19, the ribosomal protein L40 or the ribosomal protein S27A; an insect proteasome subunit such as the Rpn6 protein, the Pros 25, the Rpn2 protein, the proteasome beta 1 subunit protein or the Pros beta 2 protein; an insect β-coatomer of the COPI vesicle, the γ-coatomer of the COPI vesicle, the β'-coatomer protein or the ζ-coatomer of the COPI vesicle; an insect Tetraspanine 2 A protein which is a putative transmembrane domain protein; an insect protein belonging to the actin family such as Actin 5C; an insect ubiquitin-5E protein; an insect Sec23 protein which is a GTPase activator involved in intracellular protein transport; an insect crinkled protein which is an unconventional myosin which is involved in motor activity; an insect crooked neck protein which is involved in the regulation of nuclear alternative mRNA splicing; an insect vacuolar H+-ATPase G-subunit protein and an insect Tbp-1 such as Tat-binding protein. PCT publication WO 2007/035650 describes ribonucleic acid (RNA or double stranded RNA) that inhibits or down regulates the expression of a target gene that encodes Snf7. US Patent Application publication 2011/0054007 describes polynucleotide silencing elements targeting RPS10. US Patent Application publication 2014/0275208 and US2015/0257389 describes polynucleotide silencing elements targeting RyanR and PAT3. PCT publications WO/2016/138106, WO 2016/060911, WO 2016/060912, WO 2016/060913, and WO 2016/060914 describe polynucleotide silencing elements targeting COPI coatomer subunit nucleic acid molecules that confer resistance to Coleopteran and Hemipteran pests. US Patent Application Publications 2012/029750, US 20120297501, and 2012/0322660 describe interfering ribonucleic acids (RNA or double stranded RNA) that functions upon uptake by an insect pest species to down-regulate expression of a target gene in said insect pest, wherein the RNA comprises at least one silencing element wherein the silencing element is a region of double-stranded RNA comprising annealed complementary strands, one strand of which comprises or consists of a sequence of nucleotides which is at least partially complementary to a target nucleotide sequence within the target gene. US Patent Application Publication 2012/0164205 describe potential targets for interfering double stranded ribonucleic acids for inhibiting invertebrate pests including: a Chd3 Homologous Sequence, a Beta-Tubulin Homologous Sequence, a 40 kDa V-ATPase Homologous Sequence, a EF1α Homologous Sequence, a 26S Proteosome Subunit p28 Homologous Sequence, a Juvenile Hormone Epoxide Hydrolase Homologous Sequence, a Swelling Dependent Chloride Channel Protein Homologous Sequence, a Glucose-6-Phosphate 1-Dehydrogenase Protein Homologous Sequence, an Act42A Protein Homologous Sequence, a ADP-Ribosylation Factor 1 Homologous Sequence, a Transcription Factor IIB Protein Homologous Sequence, a Chitinase Homologous Sequences, a Ubiquitin Conjugating Enzyme Homologous Sequence, a Glyceraldehyde-3-Phosphate Dehydrogenase Homologous Sequence, an Ubiquitin B Homologous Sequence, a Juvenile Hormone Esterase Homolog, and an Alpha Tubuliln Homologous Sequence.

Use in Pesticidal Control

General methods for employing strains comprising a nucleic acid sequence of the embodiments or a variant thereof, in pesticide control or in engineering other organisms as pesticidal agents are known in the art.

Microorganism hosts that are known to occupy the "phytosphere" (phylloplane, phyllosphere, rhizosphere, and/or rhizoplana) of one or more crops of interest may be selected. These microorganisms are selected so as to be capable of successfully competing in the particular environment with the wild-type microorganisms, provide for stable maintenance and expression of the gene(s) expressing one or more of the IPD101 polypeptides and desirably provide for improved protection of the pesticide from environmental degradation and inactivation.

Alternatively, the IPD101 polypeptide is produced by introducing a heterologous gene into a cellular host. Expression of the heterologous gene results, directly or indirectly, in the intracellular production and maintenance of the pesticide. These cells are then treated under conditions that prolong the activity of the toxin produced in the cell when the cell is applied to the environment of target pest(s). The resulting product retains the toxicity of the toxin. These naturally encapsulated IPD101 polypeptides may then be formulated in accordance with conventional techniques for application to the environment hosting a target pest, e.g., soil, water, and foliage of plants. See, for example EPA 0192319, and the references cited therein.

Pesticidal Compositions

In some embodiments the active ingredients can be applied in the form of compositions and can be applied to the crop area or plant to be treated, simultaneously or in succession, with other compounds. These compounds can be fertilizers, weed killers, Cryoprotectants, surfactants, detergents, pesticidal soaps, dormant oils, polymers, and/or time-release or biodegradable carrier formulations that permit long-term dosing of a target area following a single application of the formulation. They can also be selective herbicides, chemical insecticides, virucides, microbicides, amoebicides, pesticides, fungicides, bacteriocides, nematocides, molluscicides or mixtures of several of these preparations, if desired, together with further agriculturally acceptable carriers, surfactants or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilizers. Likewise, the formulations may be prepared into edible "baits" or fashioned into pest "traps" to permit feeding or ingestion by a target pest of the pesticidal formulation.

Methods of applying an active ingredient or an agrochemical composition that contains at least one of the IPD101 polypeptide(s) produced by the bacterial strains include leaf application, seed coating and soil application. The number of applications and the rate of application depend on the intensity of infestation by the corresponding pest.

The composition may be formulated as a powder, dust, pellet, granule, spray, emulsion, colloid, solution or such like, and may be prepared by such conventional means as desiccation, lyophilization, homogenation, extraction, filtration, centrifugation, sedimentation or concentration of a culture of cells comprising the polypeptide. In all such compositions that contain at least one such pesticidal polypeptide, the polypeptide may be present in a concentration of from about 1% to about 99% by weight.

Lepidopteran, Dipteran, Heteropteran, nematode, Hemiptera or Coleopteran pests may be killed or reduced in numbers in a given area by the methods of the disclosure or may be prophylactically applied to an environmental area to prevent infestation by a susceptible pest. Preferably the pest ingests or is contacted with, a pesticidally-effective amount of the polypeptide. "Pesticidally-effective amount" as used herein refers to an amount of the pesticide that is able to bring about death to at least one pest or to noticeably reduce pest growth, feeding or normal physiological development. This amount will vary depending on such factors as, for example, the specific target pests to be controlled, the specific environment, location, plant, crop or agricultural site to be treated, the environmental conditions and the method, rate, concentration, stability, and quantity of application of the pesticidally-effective polypeptide composition. The formulations may also vary with respect to climatic conditions, environmental considerations, and/or frequency of application and/or severity of pest infestation.

The pesticide compositions described may be made by formulating either the bacterial cell, Crystal and/or spore suspension or isolated protein component with the desired agriculturally-acceptable carrier. The compositions may be formulated prior to administration in an appropriate means such as lyophilized, freeze-dried, desiccated or in an aqueous carrier, medium or suitable diluent, such as saline or other buffer.

The formulated compositions may be in the form of a dust or granular material or a suspension in oil (vegetable or mineral) or water or oil/water emulsions or as a wettable powder or in combination with any other carrier material suitable for agricultural application. Suitable agricultural carriers can be solid or liquid and are well known in the art. The term "agriculturally-acceptable carrier" covers all adjuvants, inert components, dispersants, surfactants, tackifiers, binders, etc. that are ordinarily used in pesticide formulation technology; these are well known to those skilled in pesticide formulation. The formulations may be mixed with one or more solid or liquid adjuvants and prepared by various means, e.g., by homogeneously mixing, blending and/or grinding the pesticidal composition with suitable adjuvants using conventional formulation techniques. Suitable formulations and application methods are described in U.S. Pat. No. 6,468,523. The plants can also be treated with one or more chemical compositions, including one or more herbicide, insecticides or fungicides. Exemplary chemical compositions include: Fruits/Vegetables Herbicides: Atrazine, Bromacil, Diuron, Glyphosate, Linuron, Metribuzin, Simazine, Trifluralin, Fluazifop, Glufosinate, Halo sulfuron Gowan, Paraquat, Propyzamide, Sethoxydim, Butafenacil, Halosulfuron, Indaziflam; Fruits/Vegetables Insecticides: Aldicarb, *Bacillus thuriengiensis*, Carbaryl, Carbofuran, Chlorpyrifos, Cypermethrin, Deltamethrin, Diazinon, Malathion, Abamectin, Cyfluthrin/beta-cyfluthrin, Esfenvalerate, Lambda-cyhalothrin, Acequinocyl, Bifenazate, Methoxyfenozide, Novaluron, Chromafenozide, Thiacloprid, Dinotefuran, FluaCrypyrim, Tolfenpyrad, Clothianidin, Spirodiclofen, Gamma-cyhalothrin, Spiromesifen, Spinosad, Rynaxypyr, Cyazypyr, Spinoteram, Triflumuron, Spirotetramat, Imidacloprid, Flubendiamide, Thiodicarb, Metaflumizone, Sulfoxaflor, Cyflumetofen, Cyanopyrafen, Imidacloprid, Clothianidin, Thiamethoxam, Spinotoram, Thiodicarb, Flonicamid, Methiocarb, Emamectin-benzoate, Indoxacarb, Forthiazate, Fenamiphos, Cadusaphos, Pyriproxifen, Fenbutatin-oxid, Hexthiazox, Methomyl, 4-[[(6-Chloropyridin-3-yl)methyl](2,2-difluorethyl)amino]furan-2(5H)-on; Fruits/Vegetables Fungicides: Carbendazim, Chlorothalonil, EBDCs, Sulphur, Thiophanate-methyl, Azoxystrobin, Cymoxanil, Fluazinam, Fosetyl, Iprodione, Kresoxim-methyl, Metalaxyl/mefenoxam, Trifloxystrobin, Ethaboxam, Iprovalicarb, Trifloxystrobin, Fenhexamid, Oxpoconazole fumarate, Cyazofamid, Fenamidone, Zoxamide, Picoxystrobin, Pyraclostrobin, Cyflufenamid, Boscalid; Cereals Herbicides: Isoproturon, Bromoxynil, Ioxynil, Phenoxies, Chlorsulfuron, Clodinafop, Diclofop, Diflufenican, Fenoxaprop, Florasulam, Fluoroxypyr, Metsulfuron, Triasulfuron, Flucarbazone, Iodosulfuron, Propoxycarbazone, Picolinafen, Mesosulfuron, Beflubutamid, Pinoxaden, Amidosulfuron, Thifensulfuron Methyl, Tribenuron, Flupyrsulfuron, Sulfosulfuron, Pyrasulfotole, Pyroxsulam, Flufenacet, Tralkoxydim, Pyroxasulfon; Cereals Fungicides: Carbendazim, Chlorothalonil, Azoxystrobin, Cyproconazole, Cyprodinil, Fenpropimorph, Epoxiconazole, Kresoxim-methyl, Quinoxyfen, Tebuconazole, Trifloxystrobin, Simeconazole, Picoxystrobin, Pyraclostrobin, Dimoxystrobin, Prothioconazole, Fluoxastrobin; Cereals Insecticides: Dimethoate, Lambda-cyhalthrin, Deltamethrin, alpha-Cypermethrin, β-cyfluthrin, Bifenthrin, Imidacloprid, Clothianidin, Thiamethoxam, Thiacloprid, Acetamiprid, Dinetofuran, Clorphyriphos, Metamidophos, Oxidemethon-methyl, Pirimicarb, Methiocarb; Maize Herbicides: Atrazine, Alachlor, Bromoxynil, Acetochlor, Dicamba, Clopyralid, (S-) Dimethenamid, Glufosinate, Glyphosate, Isoxaflutole, (S-)Metolachlor, Mesotrione, Nicosulfuron, Primisulfuron, Rimsulfuron, Sulcotrione, Foramsulfuron, Topramezone, Tembotrione, Saflufenacil, Thiencarbazone, Flufenacet, Pyroxasulfon; Maize Insecticides: Carbofuran, Chlorpyrifos, Bifenthrin, Fipronil, Imidacloprid, Lambda-Cyhalothrin, Tefluthrin, Terbufos, Thiamethoxam, Clothianidin, Spiromesifen, Flubendiamide, Triflumuron, Rynaxypyr, Deltamethrin, Thiodicarb, β-Cyfluthrin, Cypermethrin, Bifenthrin, Lufenuron, Triflumoron, Tefluthrin, Tebupirimphos, Ethiprole, Cyazypyr, Thiacloprid, Acetamiprid, Dinetofuran, Avermectin, Methiocarb, Spirodiclofen, Spirotetramat; Maize Fungicides: Fenitropan, Thiram, Prothioconazole, Tebuconazole, Trifloxystrobin; Rice Herbicides: Butachlor, Propanil, Azimsulfuron, Bensulfuron, Cyhalofop, Daimuron, Fentrazamide, Imazosulfuron, Mefenacet, Oxaziclomefone, Pyrazosulfuron, Pyributicarb, Quinclorac, Thiobencarb, Indanofan, Flufenacet, Fentrazamide, Halosulfuron, Oxaziclomefone, Benzobicyclon, Pyriftalid, Penoxsulam, Bispyribac, Oxadiargyl, Ethoxysulfuron, Pretilachlor, Mesotrione, Tefuryltrione, Oxadiazone, Fenoxaprop, Pyrimisulfan; Rice Insecticides: Diazinon, Fenitrothion, Fenobucarb, Monocrotophos, Benfuracarb, Buprofezin, Dinotefuran, Fipronil, Imidacloprid, Isoprocarb, Thiacloprid, Chromafenozide, Thiacloprid, Dinotefuran, Clothianidin, Ethiprole, Flubendiamide, Rynaxypyr, Deltamethrin, Acetamiprid, Thiamethoxam, Cyazypyr, Spinosad, Spinotoram, Emamectin-Benzoate, Cypermethrin, Chlorpyriphos, Cartap, Methamidophos, Etofenprox, Triazophos, 4-[[(6-Chlorpyridin-3-yl)methyl](2,2-difluorethyl)amino]furan-2(5H)-on, Carbofuran, Benfuracarb; Rice Fungicides: Thiophanate-methyl, Azoxystrobin, Carpropamid, Edifenphos, Ferimzone, Iprobenfos, Isoprothiolane, Pencycuron, Probenazole, Pyroquilon, Tricyclazole, Trifloxystrobin, Diclocymet, Fenoxanil, Simeconazole, Tiadinil; Cotton Herbicides: Diuron, Fluometuron, MSMA, Oxyfluorfen, Prometryn, Trifluralin, Carfentrazone, Clethodim, Fluazifop-butyl, Glyphosate, Norflurazon, Pendimethalin, Pyrithiobac-sodium, Trifloxysulfuron, Tepraloxydim, Glufosinate, Flumioxazin, Thidiazuron; Cotton Insecticides: Acephate, Aldicarb, Chlorpyrifos, Cypermethrin, Deltamethrin, Malathion, Monocrotophos, Abamectin, Acetamiprid, Emamectin Benzoate, Imidacloprid, Indoxacarb, Lambda-Cyhalothrin, Spinosad, Thiodicarb, Gamma-Cyhalothrin, Spiromesifen, Pyridalyl, Flonicamid, Flubendiamide, Triflumuron, Rynaxypyr, Beta-Cyfluthrin, Spirotetramat, Clothianidin, Thiamethoxam, Thiacloprid, Dinetofuran, Flubendiamide, Cyazypyr, Spinosad, Spinotoram, gamma Cyhalothrin, 4-[[(6-Chlorpyridin-3-yl)methyl](2,2-difluorethyl)amino]furan-2(5H)-on, Thiodicarb, Avermectin, Flonicamid, Pyridalyl, Spiromesifen, Sulfoxaflor, Profenophos, Thriazophos, Endosulfan; Cotton Fungicides: Etridiazole, Metalaxyl, Quintozene; Soybean Herbicides: Alachlor, Bentazone, Trifluralin, Chlorimuron-Ethyl, Cloransulam-Methyl, Fenoxaprop, Fomesafen, Fluazifop, Glyphosate, Imazamox, Imazaquin, Imazethapyr, (S-) Metolachlor, Metribuzin, Pendimethalin, Tepraloxydim, Glufosinate; Soybean Insecticides: Lambda-cyhalothrin, Methomyl, Parathion, Thiocarb, Imidacloprid, Clothianidin, Thiamethoxam, Thiacloprid, Acetamiprid, Dinetofuran, Flubendiamide, Rynaxypyr, Cyazypyr, Spinosad, Spinotoram, Emamectin-Benzoate, Fipronil, Ethiprole, Deltamethrin, β-Cyfluthrin, gamma and lambda Cyhalothrin, 4-[[(6-Chlorpyridin-3-yl)methyl](2,2-difluorethyl)amino]furan-2 (5H)-on, Spirotetramat, Spinodiclofen, Triflumuron, Flonicamid, Thiodicarb, beta-Cyfluthrin; Soybean Fungicides: Azoxystrobin, Cyproconazole, Epoxiconazole, Flutriafol, Pyraclostrobin, Tebuconazole, Trifloxystrobin, Prothioconazole, Tetraconazole; Sugarbeet Herbicides: Chloridazon, Desmedipham, Ethofumesate, Phenmedipham, Triallate, Clopyralid, Fluazifop, Lenacil, Metamitron, Quinmerac, Cycloxydim, Triflusulfuron, Tepraloxydim, Quizalofop; Sugarbeet Insecticides: Imidacloprid, Clothianidin, Thiamethoxam, Thiacloprid, Acetamiprid, Dinetofuran, Deltamethrin, β-Cyfluthrin, gamma/lambda Cyhalothrin, 4-[[(6-Chlorpyridin-3-yl)methyl](2,2-difluorethyl)amino]furan-2(5H)-on, Tefluthrin, Rynaxypyr, Cyaxypyr, Fipronil, Carbofuran; Canola Herbicides: Clopyralid, Diclofop, Fluazifop, Glufosinate, Glyphosate, Metazachlor, Trifluralin Ethametsulfuron, Quinmerac, Quizalofop, Clethodim, Tepraloxydim; Canola Fungicides: Azoxystrobin, Carbendazim, Fludioxonil, Iprodione, Prochloraz, Vinclozolin; Canola Insecticides: Carbofuran organophosphates, Pyrethroids, Thiacloprid, Deltamethrin, Imidacloprid, Clothianidin, Thiamethoxam, Acetamiprid, Dinetofuran, β-Cyfluthrin, gamma and lambda Cyhalothrin, tau-Fluvaleriate, Ethiprole, Spinosad, Spinotoram, Flubendiamide, Rynaxypyr, Cyazypyr, 4-[[(6-Chlorpyridin-3-yl)methyl](2,2-difluorethyl)amino]furan-2(5H)-on.

In some embodiments the herbicide is Atrazine, Bromacil, Diuron, Chlorsulfuron, Metsulfuron, Thifensulfuron Methyl, Tribenuron, Acetochlor, Dicamba, Isoxaflutole, Nicosulfuron, Rimsulfuron, Pyrithiobac-sodium, Flumioxazin, Chlorimuron-Ethyl, Metribuzin, Quizalofop, S-metolachlor, Hexazinne or combinations thereof.

In some embodiments the insecticide is Esfenvalerate, Chlorantraniliprole, Methomyl, Indoxacarb, Oxamyl or combinations thereof.

Pesticidal and Insecticidal Activity

"Pest" includes but is not limited to, insects, fungi, bacteria, nematodes, mites, ticks and the like. Insect pests include insects selected from the orders Coleoptera, Diptera, Hymenoptera, Lepidoptera, Mallophaga, Homoptera, Hemiptera Orthroptera, Thysanoptera, Dermaptera, Isoptera, Anoplura, Siphonaptera, Trichoptera, etc., particularly Lepidoptera and Coleoptera.

Those skilled in the art will recognize that not all compounds are equally effective against all pests. Compounds of the embodiments display activity against insect pests, which may include economically important agronomic, forest, greenhouse, nursery ornamentals, food and fiber, public and animal health, domestic and commercial structure, household and stored product pests.

Larvae of the order Lepidoptera include, but are not limited to, armyworms, cutworms, loopers and heliothines in the family Noctuidae *Spodoptera frugiperda* JE Smith (fall armyworm); *S. exigua* Hübner (beet armyworm); *S. litura* Fabricius (tobacco cutworm, cluster caterpillar); *Mamestra configurata* Walker (bertha armyworm); *M. brassicae* Linnaeus (cabbage moth); *Agrotis ipsilon* Hufnagel (black cutworm); *A. orthogonia* Morrison (western cutworm); *A. subterranea* Fabricius (granulate cutworm); *Alabama argillacea* Hübner (cotton leaf worm); *Trichoplusia ni* Hübner (cabbage looper); *Pseudoplusia includens* Walker (soybean looper); *Anticarsia gemmatalis* Hübner (velvetbean caterpillar); *Hypena scabra* Fabricius (green cloverworm); *Heliothis virescens* Fabricius (tobacco budworm); *Pseudaletia unipuncta* Haworth (armyworm); *Athetis min-*

*dara* Barnes and Mcdunnough (rough skinned cutworm); *Euxoa messoria* Harris (darksided cutworm); *Earias insulana* Boisduval (spiny bollworm); *E. vittella* Fabricius (spotted bollworm); *Helicoverpa armigera* Hübner (American bollworm); *H. zea* Boddie (corn earworm or cotton bollworm); *Melanchra picta* Harris (zebra caterpillar); *Egira* (*Xylomyges*) *curialis* Grote (citrus cutworm); borers, casebearers, webworms, coneworms, and skeletonizers from the family Pyralidae *Ostrinia nubilalis* Hübner (European corn borer); *Amyelois transitella* Walker (naval orangeworm); *Anagasta kuehniella* Zeller (Mediterranean flour moth); *Cadra cautella* Walker (almond moth); *Chilo suppressalis* Walker (rice stem borer); *C. partellus*, (sorghum borer); *Corcyra cephalonica* Stainton (rice moth); *Crambus caliginosellus* Clemens (corn root webworm); *C. teterrellus* Zincken (bluegrass webworm); *Cnaphalocrocis medinalis* Guenée (rice leaf roller); *Desmia funeralis* Hübner (grape leaffolder); *Diaphania hyalinata* Linnaeus (melon worm); *D. nitidalis* Stoll (pickleworm); *Diatraea grandiosella* Dyar (southwestern corn borer), *D. saccharalis* Fabricius (surgarcane borer); *Eoreuma loftini* Dyar (Mexican rice borer); *Ephestia elutella* Hübner (tobacco (cacao) moth); *Galleria mellonella* Linnaeus (greater wax moth); *Herpetogramma licarsisalis* Walker (sod webworm); *Homoeosoma electellum* Hulst (sunflower moth); *Elasmopalpus lignosellus* Zeller (lesser cornstalk borer); *Achroia grisella* Fabricius (lesser wax moth); *Loxostege sticticalis* Linnaeus (beet webworm); *Orthaga thyrisalis* Walker (tea tree web moth); *Maruca testulalis* Geyer (bean pod borer); *Plodia interpunctella* Hübner (Indian meal moth); *Scirpophaga incertulas* Walker (yellow stem borer); *Udea rubigalis* Guenée (celery leaftier); and leafrollers, budworms, seed worms and fruit worms in the family Tortricidae *Acleris gloverana* Walsingham (Western blackheaded budworm); *A. variana* Fernald (Eastern blackheaded budworm); *Archips argyrospila* Walker (fruit tree leaf roller); *A. rosana* Linnaeus (European leaf roller); and other *Archips* species, *Adoxophyes orana* Fischer von Rösslerstamm (summer fruit *tortrix* moth); *Cochylis hospes* Walsingham (banded sunflower moth); *Cydia latiferreana* Walsingham (filbertworm); *C. pomonella* Linnaeus (coding moth); *Platynota flavedana* Clemens (variegated leafroller); *P. stultana* Walsingham (omnivorous leafroller); *Lobesia botrana* Denis & Schiffermüller (European grape vine moth); *Spilonota ocellana* Denis & Schiffermiffier (eyespotted bud moth); *Endopiza viteana* Clemens (grape berry moth); *Eupoecilia ambiguella* Hübner (vine moth); *Bonagota salubricola* Meyrick (Brazilian apple leafroller); *Grapholita molesta* Busck (oriental fruit moth); *Suleima helianthana* Riley (sunflower bud moth); *Argyrotaenia* spp.; *Choristoneura* spp.

Selected other agronomic pests in the order Lepidoptera include, but are not limited to, *Alsophila pometaria* Harris (fall cankerworm); *Anarsia lineatella* Zeller (peach twig borer); *Anisota senatoria* J. E. Smith (orange striped oakworm); *Antheraea pernyi* Guérin-Méneville (Chinese Oak Tussah Moth); *Bombyx mori* Linnaeus (Silkworm); *Bucculatrix thurberiella* Busck (cotton leaf perforator); *Colias eurytheme* Boisduval (alfalfa caterpillar); *Datana integerrima* Grote & Robinson (walnut caterpillar); *Dendrolimus sibiricus* Tschetwerikov (Siberian silk moth), *Ennomos subsignaria* Hübner (elm spanworm); *Erannis tiliaria* Harris (linden looper); *Euproctis chrysorrhoea* Linnaeus (browntail moth); *Harrisina americana* Guérin-Méneville (grapeleaf skeletonizer); *Hemileuca oliviae* Cockrell (range caterpillar); *Hyphantria cunea* Drury (fall webworm); *Keiferia lycopersicella* Walsingham (tomato pinworm); *Lambdina fiscellaria fiscellaria* Hulst (Eastern hemlock looper); *L. fiscellaria lugubrosa* Hulst (Western hemlock looper); *Leucoma salicis* Linnaeus (satin moth); *Lymantria dispar* Linnaeus (gypsy moth); *Manduca quinquemaculata* Haworth (five spotted hawk moth, tomato hornworm); *M. sexta* Haworth (tomato hornworm, tobacco hornworm); *Operophtera brumata* Linnaeus (winter moth); *Paleacrita vernata* Peck (spring cankerworm); *Papilio cresphontes* Cramer (giant swallowtail orange dog); *Phryganidia californica* Packard (California oakworm); *Phyllocnistis citrella* Stainton (citrus leafminer); *Phyllonorycter blancardella* Fabricius (spotted tentiform leafminer); *Pieris brassicae* Linnaeus (large white butterfly); *P. rapae* Linnaeus (small white butterfly); *P. napi* Linnaeus (green veined white butterfly); *Platyptilia carduidactyla* Riley (artichoke plume moth); *Plutella xylostella* Linnaeus (diamondback moth); *Pectinophora gossypiella* Saunders (pink bollworm); *Pontia protodice* Boisduval and Leconte (Southern cabbageworm); *Sabulodes aegrotata* Guenée (omnivorous looper); *Schizura concinna* J. E. Smith (red humped caterpillar); *Sitotroga cerealella* Olivier (Angoumois grain moth); *Thaumetopoea pityocampa* Schiffermuller (pine processionary caterpillar); *Tineola bisselliella* Hummel (webbing clothesmoth); *Tuta absoluta* Meyrick (tomato leafminer); *Yponomeuta padella* Linnaeus (ermine moth); *Heliothis subflexa* Guenée; *Malacosoma* spp. and *Orgyia* spp.

Of interest are larvae and adults of the order Coleoptera including weevils from the families Anthribidae, Bruchidae and Curculionidae (including, but not limited to: *Anthonomus grandis* Boheman (boll weevil); *Lissorhoptrus oryzophilus* Kuschel (rice water weevil); *Sitophilus granarius* Linnaeus (granary weevil); *S. oryzae* Linnaeus (rice weevil); *Hypera punctata* Fabricius (clover leaf weevil); *Cylindrocopturus adspersus* LeConte (sunflower stem weevil); *Smicronyx fulvus* LeConte (red sunflower seed weevil); *S. sordidus* LeConte (gray sunflower seed weevil); *Sphenophorus maidis* Chittenden (maize billbug)); flea beetles, cucumber beetles, rootworms, leaf beetles, potato beetles and leafminers in the family Chrysomelidae (including, but not limited to: *Leptinotarsa decemlineata* Say (Colorado potato beetle); *Diabrotica virgifera virgifera* LeConte (western corn rootworm); *D. barberi* Smith and Lawrence (northern corn rootworm); *D. undecimpunctata howardi* Barber (southern corn rootworm); *Chaetocnema pulicaria* Melsheimer (corn flea beetle); *Phyllotreta cruciferae* Goeze (Crucifer flea beetle); *Phyllotreta striolata* (stripped flea beetle); *Colaspis brunnea* Fabricius (grape *colaspis*); *Oulema melanopus* Linnaeus (cereal leaf beetle); *Zygogramma exclamationis* Fabricius (sunflower beetle)); beetles from the family Coccinellidae (including, but not limited to: *Epilachna varivestis* Mulsant (Mexican bean beetle)); chafers and other beetles from the family Scarabaeidae (including, but not limited to: *Popillia japonica* Newman (Japanese beetle); *Cyclocephala borealis* Arrow (northern masked chafer, white grub); *C. immaculata* Olivier (southern masked chafer, white grub); *Rhizotrogus majalis* Razoumowsky (European chafer); *Phyllophaga crinita* Burmeister (white grub); *Ligyrus gibbosus* De Geer (carrot beetle)); carpet beetles from the family Dermestidae; wireworms from the family Elateridae, *Eleodes* spp., *Melanotus* spp.; *Conoderus* spp.; *Limonius* spp.; *Agriotes* spp.; *Ctenicera* spp.; *Aeolus* spp.; bark beetles from the family Scolytidae and beetles from the family Tenebrionidae.

Adults and immatures of the order Diptera are of interest, including leafminers *Agromyza parvicornis* Loew (corn blotch leafminer); midges (including, but not limited to: *Contarinia sorghicola* Coquillett (sorghum midge); *Mayetiola destructor* Say (Hessian fly); *Sitodiplosis mosellana*

Géhin (wheat midge); *Neolasioptera murtfeldtiana* Felt, (sunflower seed midge)); fruit flies (Tephritidae), *Oscinella frit* Linnaeus (fruit flies); maggots (including, but not limited to: *Delia platura* Meigen (seedcorn maggot); *D. coarctata* Fallen (wheat bulb fly) and other *Delia* spp., *Meromyza americana* Fitch (wheat stem maggot); *Musca domestica* Linnaeus (house flies); *Fannia canicularis* Linnaeus, *F. femoralis* Stein (lesser house flies); *Stomoxys calcitrans* Linnaeus (stable flies)); face flies, horn flies, blow flies, *Chrysomya* spp.; *Phormia* spp. and other muscoid fly pests, horse flies *Tabanus* spp.; bot flies *Gastrophilus* spp.; *Oestrus* spp.; cattle grubs *Hypoderma* spp.; deer flies *Chrysops* spp.; *Melophagus ovinus* Linnaeus (keds) and other *Brachycera*, mosquitoes *Aedes* spp.; *Anopheles* spp.; *Culex* spp.; black flies *Prosimulium* spp.; *Simulium* spp.; biting midges, sand flies, sciarids, and other *Nematocera*.

Included as insects of interest are adults and nymphs of the orders Hemiptera and Homoptera such as, but not limited to, adelgids from the family Adelgidae, plant bugs from the family Miridae, cicadas from the family Cicadidae, leafhoppers, *Empoasca* spp.; from the family Cicadellidae, planthoppers from the families Cixiidae, Flatidae, Fulgoroidea, Issidae and Delphacidae, treehoppers from the family Membracidae, psyllids from the family Psyllidae, whiteflies from the family Aleyrodidae, aphids from the family Aphididae, phylloxera from the family Phylloxeridae, mealybugs from the family Pseudococcidae, scales from the families Asterolecanidae, Coccidae, Dactylopiidae, Diaspididae, Eriococcidae Ortheziidae, Phoenicococcidae and Margarodidae, lace bugs from the family Tingidae, stink bugs from the family Pentatomidae, cinch bugs, *Blissus* spp.; and other seed bugs from the family Lygaeidae, spittlebugs from the family Cercopidae squash bugs from the family Coreidae and red bugs and cotton stainers from the family Pyrrhocoridae.

Agronomically important members from the order Homoptera further include, but are not limited to: *Acyrthisiphon pisum* Harris (pea aphid); *Aphis craccivora* Koch (cowpea aphid); *A. fabae* Scopoli (black bean aphid); *A. gossypii* Glover (cotton aphid, melon aphid); *A. maidiradicis* Forbes (corn root aphid); *A. pomi* De Geer (apple aphid); *A. spiraecola* Patch (spirea aphid); *Aulacorthum solani* Kaltenbach (foxglove aphid); *Chaetosiphon fragaefolii* Cockerell (strawberry aphid); *Diuraphis noxia* Kurdjumov/ Mordvilko (Russian wheat aphid); *Dysaphis plantaginea* Paaserini (rosy apple aphid); *Eriosoma lanigerum* Hausmann (woolly apple aphid); *Brevicoryne brassicae* Linnaeus (cabbage aphid); *Hyalopterus pruni* Geoffroy (mealy plum aphid); *Lipaphis erysimi* Kaltenbach (turnip aphid); *Metopolophium dirrhodum* Walker (cereal aphid); *Macrosiphum euphorbiae* Thomas (potato aphid); *Myzus persicae* Sulzer (peach-potato aphid, green peach aphid); *Nasonovia ribisnigri* Mosley (lettuce aphid); *Pemphigus* spp. (root aphids and gall aphids); *Rhopalosiphum maidis* Fitch (corn leaf aphid); *R. padi* Linnaeus (bird cherry-oat aphid); *Schizaphis graminum* Rondani (greenbug); *Sipha flava* Forbes (yellow sugarcane aphid); *Sitobion avenae* Fabricius (English grain aphid); *Therioaphis maculata* Buckton (spotted alfalfa aphid); *Toxoptera aurantii* Boyer de Fonscolombe (black citrus aphid) and *T. citricida* Kirkaldy (brown citrus aphid); *Adelges* spp. (adelgids); *Phylloxera devastatrix* Pergande (pecan *phylloxera*); *Bemisia tabaci* Gennadius (tobacco whitefly, sweetpotato whitefly); *B. argentifolii* Bellows & Perring (silverleaf whitefly); *Dialeurodes citri* Ashmead (citrus whitefly); *Trialeurodes abutiloneus* (bandedwinged whitefly) and *T. vaporariorum* Westwood (greenhouse whitefly); *Empoasca fabae* Harris (potato leafhopper); *Laodelphax striatellus* Fallen (smaller brown planthopper); *Macrolestes quadrilineatus* Forbes (aster leafhopper); *Nephotettix cinticeps* Uhler (green leafhopper); *N. nigropictus* Stat (rice leafhopper); *Nilaparvata lugens* Stat (brown planthopper); *Peregrinus maidis* Ashmead (corn planthopper); *Sogatella furcifera* Horvath (white-backed planthopper); *Sogatodes orizicola* Muir (rice delphacid); *Typhlocyba pomaria* McAtee (white apple leafhopper); *Erythroneoura* spp. (grape leafhoppers); *Magicicada septendecim* Linnaeus (periodical cicada); *Icerya purchasi* Maskell (cottony cushion scale); *Quadraspidiotus perniciosus* Comstock (San Jose scale); *Planococcus citri* Risso (citrus mealybug); *Pseudococcus* spp. (other mealybug complex); *Cacopsylla pyricola* Foerster (pear *psylla*); *Trioza diospyri* Ashmead (persimmon *psylla*).

Agronomically important species of interest from the order Hemiptera include, but are not limited to: *Acrosternum hilare* Say (green stink bug); *Anasa tristis* De Geer (squash bug); *Blissus leucopterus leucopterus* Say (chinch bug); *Corythuca gossypii* Fabricius (cotton lace bug); *Cyrtopeltis modesta* Distant (tomato bug); *Dysdercus suturellus* Herrich-Schäffer (cotton stainer); *Euschistus servus* Say (brown stink bug); *E. variolarius* Palisot de Beauvois (one-spotted stink bug); *Graptostethus* spp. (complex of seed bugs); *Leptoglossus corculus* Say (leaf-footed pine seed bug); *Lygus lineolaris* Palisot de Beauvois (tarnished plant bug); *L. Hesperus* Knight (Western tarnished plant bug); *L. pratensis* Linnaeus (common meadow bug); *L. rugulipennis* Poppius (European tarnished plant bug); *Lygocoris pabulinus* Linnaeus (common green capsid); *Nezara viridula* Linnaeus (southern green stink bug); *Oebalus pugnax* Fabricius (rice stink bug); *Oncopeltus fasciatus* Dallas (large milkweed bug); *Pseudatomoscelis seriatus* Reuter (cotton fleahopper).

Furthermore, embodiments may be effective against Hemiptera such, *Calocoris norvegicus* Gmelin (strawberry bug); *Orthops campestris* Linnaeus; *Plesiocoris rugicollis* Fallen (apple capsid); *Cyrtopeltis modestus* Distant (tomato bug); *Cyrtopeltis notatus* Distant (suckfly); *Spanagonicus albofasciatus* Reuter (whitemarked fleahopper); *Diaphnocoris chlorionis* Say (honeylocust plant bug); *Labopidicola allii* Knight (onion plant bug); *Pseudatomoscelis seriatus* Reuter (cotton fleahopper); *Adelphocoris rapidus* Say (rapid plant bug); *Poecilocapsus lineatus* Fabricius (four-lined plant bug); *Nysius ericae* Schilling (false chinch bug); *Nysius raphanus* Howard (false chinch bug); *Nezara viridula* Linnaeus (Southern green stink bug); *Eurygaster* spp.; *Coreidae* spp.; *Pyrrhocoridae* spp.; *Tinidae* spp.; *Blostomatidae* spp.; *Reduviidae* spp. and *Cimicidae* spp.

Also included are adults and larvae of the order Acari (mites) such as *Aceria tosichella* Keifer (wheat curl mite); *Petrobia latens* Müller (brown wheat mite); spider mites and red mites in the family Tetranychidae, *Panonychus ulmi* Koch (European red mite); *Tetranychus urticae* Koch (two spotted spider mite); (*T. mcdanieli* McGregor (McDaniel mite); *T. cinnabarinus* Boisduval (carmine spider mite); *T. turkestani* Ugarov & Nikolski (strawberry spider mite); flat mites in the family Tenuipalpidae, *Brevipalpus lewisi* McGregor (citrus flat mite); rust and bud mites in the family Eriophyidae and other foliar feeding mites and mites important in human and animal health, i.e., dust mites in the family Epidermoptidae, follicle mites in the family Demodicidae, grain mites in the family Glycyphagidae, ticks in the order Ixodidae. *Ixodes scapularis* Say (deer tick); *I. holocyclus* Neumann (Australian paralysis tick); *Dermacentor variabilis* Say (American dog tick); *Amblyomma americanum* Linnaeus (lone star tick) and scab and itch mites in the families Psoroptidae, Pyemotidae and Sarcoptidae.

Insect pests of the order Thysanura are of interest, such as *Lepisma saccharina* Linnaeus (silverfish); *Thermobia domestica* Packard (firebrat).

Additional arthropod pests covered include: spiders in the order Araneae such as *Loxosceles reclusa* Gertsch and Mulaik (brown recluse spider) and the *Latrodectus mactans* Fabricius (black widow spider) and centipedes in the order Scutigeromorpha such as *Scutigera coleoptrata* Linnaeus (house centipede).

Insect pest of interest include the superfamily of stink bugs and other related insects including but not limited to species belonging to the family Pentatomidae (*Nezara viridula, Halyomorpha halys, Piezodorus guildini, Euschistus servus, Acrosternum hilare, Euschistus heros, Euschistus tristigmus, Acrosternum hilare, Dichelops furcatus, Dichelops melacanthus*, and *Bagrada hilaris* (Bagrada Bug)), the family Plataspidae (*Megacopta cribraria*—Bean plataspid) and the family Cydnidae (*Scaptocoris castanea*—Root stink bug) and Lepidoptera species including but not limited to: diamond-back moth, e.g., *Helicoverpa zea* Boddie; soybean looper, e.g., *Pseudoplusia includens* Walker and velvet bean caterpillar e.g., *Anticarsia gemmatalis* Hübner.

Methods for measuring pesticidal activity are well known in the art. See, for example, Czapla and Lang, (1990) *J. Econ. Entomol.* 83:2480-2485; Andrews, et al., (1988) *Biochem. J.* 252:199-206; Marrone, et al., (1985) *J. of Economic Entomology* 78:290-293 and U.S. Pat. No. 5,743, 477. Generally, the protein is mixed and used in feeding assays. See, for example Marrone, et al., (1985) *J. of Economic Entomology* 78:290-293. Such assays can include contacting plants with one or more pests and determining the plant's ability to survive and/or cause the death of the pests.

Nematodes include parasitic nematodes such as root-knot, cyst and lesion nematodes, including *Heterodera* spp., *Meloidogyne* spp. and *Globodera* spp.; particularly members of the cyst nematodes, including, but not limited to, *Heterodera glycines* (soybean cyst nematode); *Heterodera schachtii* (beet cyst nematode); *Heterodera avenae* (cereal cyst nematode) and *Globodera rostochiensis* and *Globodera pailida* (potato cyst nematodes). Lesion nematodes include *Pratylenchus* spp.

Seed Treatment

To protect and to enhance yield production and trait technologies, seed treatment options can provide additional crop plan flexibility and cost effective control against insects, weeds and diseases. Seed material can be treated, typically surface treated, with a composition comprising combinations of chemical or biological herbicides, herbicide safeners, insecticides, fungicides, germination inhibitors and enhancers, nutrients, plant growth regulators and activators, bactericides, nematocides, avicides and/or molluscicides. These compounds are typically formulated together with further carriers, surfactants or application-promoting adjuvants customarily employed in the art of formulation. The coatings may be applied by impregnating propagation material with a liquid formulation or by coating with a combined wet or dry formulation. Examples of the various types of compounds that may be used as seed treatments are provided in The Pesticide Manual: A World Compendium, C. D. S. Tomlin Ed., Published by the British Crop Production Council.

Some seed treatments that may be used on crop seed include, but are not limited to, one or more of abscisic acid, acibenzolar-S-methyl, avermectin, amitrol, azaconazole, azospirillum, azadirachtin, azoxystrobin, *Bacillus* spp. (including one or more of *cereus, firmus, megaterium, pumilis, sphaericus, subtilis* and/or *thuringiensis* species), *bradyrhizobium* spp. (including one or more of *betae, canariense, elkanii, iriomotense, japonicum, liaonigense, pachyrhizi* and/or *yuanmingense*), captan, carboxin, chitosan, clothianidin, copper, cyazypyr, difenoconazole, etidiazole, fipronil, fludioxonil, fluoxastrobin, fluquinconazole, flurazole, fluxofenim, harpin protein, imazalil, imidacloprid, ipconazole, isoflavenoids, lipo-chitooligosaccharide, mancozeb, manganese, maneb, mefenoxam, metalaxyl, metconazole, myclobutanil, PCNB, penflufen, *penicillium*, penthiopyrad, permethrine, picoxystrobin, prothioconazole, pyraclostrobin, rynaxypyr, S-metolachlor, saponin, sedaxane, TCMTB, tebuconazole, thiabendazole, thiamethoxam, thiocarb, thiram, tolclofos-methyl, triadimenol, *trichoderma*, trifloxystrobin, triticonazole and/or zinc. PCNB seed coat refers to EPA Registration Number 00293500419, containing quintozen and terrazole. TCMTB refers to 2-(thiocyanomethylthio) benzothiazole.

Seed varieties and seeds with specific transgenic traits may be tested to determine which seed treatment options and application rates may complement such varieties and transgenic traits in order to enhance yield. For example, a variety with good yield potential but head smut susceptibility may benefit from the use of a seed treatment that provides protection against head smut, a variety with good yield potential but cyst nematode susceptibility may benefit from the use of a seed treatment that provides protection against cyst nematode, and so on. Likewise, a variety encompassing a transgenic trait conferring insect resistance may benefit from the second mode of action conferred by the seed treatment, a variety encompassing a transgenic trait conferring herbicide resistance may benefit from a seed treatment with a safener that enhances the plants resistance to that herbicide, etc. Further, the good root establishment and early emergence that results from the proper use of a seed treatment may result in more efficient nitrogen use, a better ability to withstand drought and an overall increase in yield potential of a variety or varieties containing a certain trait when combined with a seed treatment.

Methods for Killing an Insect Pest and Controlling an Insect Population

In some embodiments methods are provided for killing an insect pest, comprising contacting the insect pest, either simultaneously or sequentially, with an insecticidally-effective amount of a recombinant IPD101 polypeptide of the disclosure. In some embodiments methods are provided for killing an insect pest, comprising contacting the insect pest with an insecticidally-effective amount of one or more of a recombinant pesticidal protein of SEQ ID NOS: 2, 4, 6, 8, 10, 12, 14, 16, 18, 20, 22, 24, 25, 26, 28, 29, 30, 32, 46, 48, 50, 52, 54, 56, 58, and 60, or a variant or insecticidally active fragment thereof. In some embodiments methods are provided for controlling an insect pest population, comprising contacting the insect pest population, either simultaneously or sequentially, with an insecticidally-effective amount of one or more of a recombinant IPD101 polypeptide of the disclosure. In some embodiments, methods are provided for controlling an insect pest population, comprising contacting the insect pest population with an insecticidally-effective amount of one or more of a recombinant IPD101 polypeptide of SEQ ID NOS: 2, 4, 6, 8, 10, 12, 14, 16, 18, 20, 22, 24, 25, 26, 28, 29, 30, 32, 46, 48, 50, 52, 54, 56, 58, and 60, or a variant or insecticidally active fragment thereof. As used herein, "controlling a pest population" or "controls a pest" refers to any effect on a pest that results in limiting the damage that the pest causes. Controlling a pest includes, but is not limited to, killing the pest, inhibiting development of the pest, altering fertility or growth of the pest in such a manner that the pest provides less damage to the plant, decreasing the number of offspring produced, producing less fit pests, producing pests more susceptible to predator attack or deterring the pests from eating the plant.

In some embodiments methods are provided for controlling an insect pest population resistant to a pesticidal protein, comprising contacting the insect pest population, either simultaneously or sequentially, with an insecticidally-effective amount of one or more of a recombinant IPD101 polypeptide of the disclosure. In some embodiments, methods are provided for controlling an insect pest population resistant to a pesticidal protein, comprising contacting the insect pest population with an insecticidally-effective amount of one or more of a recombinant IPD101 polypeptide of SEQ ID NOS: 2, 4, 6, 8, 10, 12, 14, 16, 18, 20, 22, 24, 25, 26, 28, 29, 30, 32, 46, 48, 50, 52, 54, 56, 58, and 60, or a variant or insecticidally active fragment thereof.

In some embodiments methods are provided for protecting a plant from an insect pest, comprising expressing in the plant or cell thereof at least one recombinant polynucleotide encoding an IPD101 polypeptide of the disclosure. In some embodiments methods are provided for protecting a plant from an insect pest, comprising expressing in the plant or cell thereof a recombinant polynucleotide encoding one or more IPD101 polypeptides of SEQ ID NOS: 2, 4, 6, 8, 10, 12, 14, 16, 18, 20, 22, 24, 25, 26, 28, 29, 30, 32, 46, 48, 50, 52, 54, 56, 58, and 60, or variants or insecticidally active fragments thereof.

Insect Resistance Management (IRM) Strategies Expression of B. thuringiensis δ-endotoxins in transgenic corn plants has proven to be an effective means of controlling agriculturally important insect pests (Perlak, et al., 1990; 1993). However, in certain instances insects have evolved that are resistant to B. thuringiensis δ-endotoxins expressed in transgenic plants. Such resistance, should it become widespread, would clearly limit the commercial value of germplasm containing genes encoding such B. thuringiensis δ-endotoxins.

One way of increasing the effectiveness of the transgenic insecticides against target pests and contemporaneously reducing the development of insecticide-resistant pests is to use provide non-transgenic (i.e., non-insecticidal protein) refuges (a section of non-insecticidal crops/corn) for use with transgenic crops producing a single insecticidal protein active against target pests. The United States Environmental Protection Agency (epa.gov/oppbppdl/biopesticides/pips/bt_corn_refuge_2006.htm, which can be accessed using the www prefix) publishes the requirements for use with transgenic crops producing a single Bt protein active against target pests. In addition, the National Corn Growers Association, on their website: (ncga.com/insect-resistance-management-fact-sheet-bt-corn, which can be accessed using the www prefix) also provides similar guidance regarding refuge requirements. Due to losses to insects within the refuge area, larger refuges may reduce overall yield.

Another way of increasing the effectiveness of the transgenic insecticides against target pests and contemporaneously reducing the development of insecticide-resistant pests would be to have a repository of insecticidal genes that are effective against groups of insect pests and which manifest their effects through different modes of action.

Expression in a plant of two or more insecticidal compositions toxic to the same insect species, each insecticide being expressed at efficacious levels would be another way to achieve control of the development of resistance. This is based on the principle that evolution of resistance against two separate modes of action is far more unlikely than only one. Roush, for example, outlines two-toxin strategies, also called "pyramiding" or "stacking," for management of insecticidal transgenic crops. (The Royal Society. Phil. Trans. R. Soc. Lond. B. (1998) 353:1777-1786). Stacking or pyramiding of two different proteins each effective against the target pests and with little or no cross-resistance can allow for use of a smaller refuge. The US Environmental Protection Agency requires significantly less (generally 5%) structured refuge of non-Bt corn be planted than for single trait products (generally 20%). There are various ways of providing the IRM effects of a refuge, including various geometric planting patterns in the fields and in-bag seed mixtures, as discussed further by Roush.

In some embodiments the IPD101 polypeptides of the disclosure are useful as an insect resistance management strategy in combination (i.e., pyramided) with other pesticidal proteins or other transgenes (i.e., an RNAi trait) including but not limited to Bt toxins, *Xenorhabdus* sp. or *Photorhabdus* sp. insecticidal proteins, other insecticidally active proteins, and the like.

Provided are methods of controlling Lepidoptera and/or Coleoptera insect infestation(s) in a transgenic plant that promote insect resistance management, comprising expressing in the plant at least two different insecticidal proteins having different modes of action.

In some embodiments the methods of controlling Lepidoptera and/or Coleoptera insect infestation in a transgenic plant and promoting insect resistance management comprises the presentation of at least one of the IPD101 polypeptide insecticidal proteins to insects in the order Lepidoptera and/or Coleoptera.

In some embodiments the methods of controlling Lepidoptera and/or Coleoptera insect infestation in a transgenic plant and promoting insect resistance management comprises the presentation of at least one of the IPD101 polypeptides of SEQ ID NOS: 2, 4, 6, 8, 10, 12, 14, 16, 18, 20, 22, 24, 25, 26, 28, 29, 30, 32, 46, 48, 50, 52, 54, 56, 58, and 60, or variants or insecticidally active fragments thereof, insecticidal to insects in the order Lepidoptera and/or Coleoptera.

In some embodiments the methods of controlling Lepidoptera and/or Coleoptera insect infestation in a transgenic plant and promoting insect resistance management comprise expressing in the transgenic plant an IPD101 polypeptide and a Cry protein or other insecticidal protein to insects in the order Lepidoptera and/or Coleoptera having different modes of action.

In some embodiments the methods of controlling Lepidoptera and/or Coleoptera insect infestation in a transgenic plant and promoting insect resistance management comprise expression in the transgenic plant of at least one of an IPD101 polypeptide of SEQ ID NOS: 2, 4, 6, 8, 10, 12, 14, 16, 18, 20, 22, 24, 25, 26, 28, 29, 30, 32, 46, 48, 50, 52, 54, 56, 58, and 60, or variants or insecticidally active fragments thereof and a Cry protein or other insecticidal protein to insects in the order Lepidoptera and/or Coleoptera, where the IPD101 polypeptide and Cry protein have different modes of action.

Also provided are methods of reducing likelihood of emergence of Lepidoptera and/or Coleoptera insect resistance to transgenic plants expressing in the plants insecticidal proteins to control the insect species, comprising expression of at least one of an IPD101 polypeptide insecticidal to the insect species in combination with a second insecticidal protein to the insect species having different modes of action.

Also provided are means for effective Lepidoptera and/or Coleoptera insect resistance management of transgenic plants, comprising co-expressing at high levels in the plants two or more insecticidal proteins or other insecticidal transgenes (e.g., an RNAi trait) toxic to Lepidoptera and/or Coleoptera insects but each exhibiting a different mode of effectuating its killing activity, wherein two or more of the insecticidal proteins or other insecticidal transgenes comprise an IPD101 polypeptide and a Cry protein. Also provided are means for effective Lepidoptera and/or Coleoptera insect resistance management of transgenic plants, comprising co-expressing at high levels in the plants two or more insecticidal proteins or other insecticidal transgenes (e.g., an RNAi trait) toxic to Lepidoptera and/or Coleoptera insects but each exhibiting a different mode of effectuating its killing activity, wherein two or more insecticidal proteins or other insecticidal transgenes comprise at least one of an IPD101 polypeptide of SEQ ID NOS: 2, 4, 6, 8, 10, 12, 14, 16, 18, 20, 22, 24, 25, 26, 28, 29, 30, 32, 46, 48, 50, 52, 54, 56, 58, and 60, or variants or insecticidally active fragments thereof and a Cry protein or other insecticidally active protein.

In addition, methods are provided for obtaining regulatory approval for planting or commercialization of plants expressing proteins insecticidal to insects in the order Lepidoptera and/or Coleoptera, comprising the step of referring to, submitting or relying on insect assay binding data showing that the IPD101 polypeptide does not compete with binding sites for Cry proteins in such insects. In addition, methods are provided for obtaining regulatory approval for planting or commercialization of plants expressing proteins insecticidal to insects in the order Lepidoptera and/or Coleoptera, comprising the step of referring to, submitting or relying on insect assay binding data showing that one or more of the IPD101 polypeptides of SEQ ID NOS: 2, 4, 6, 8, 10, 12, 14, 16, 18, 20, 22, 24, 25, 26, 28, 29, 30, 32, 46, 48, 50, 52, 54, 56, 58, and 60, or variant or insecticidally active fragment thereof does not compete with binding sites for Cry proteins in such insects.

Methods for Increasing Plant Yield

Methods for increasing plant yield are provided. The methods comprise providing a plant or plant cell expressing a polynucleotide encoding the pesticidal polypeptide sequence disclosed herein and growing the plant or a seed thereof in a field infested with a pest against which the polypeptide has pesticidal activity. In some embodiments, the polypeptide has pesticidal activity against a Lepidopteran, Coleopteran, Dipteran, Hemipteran or nematode pest, and the field is infested with a Lepidopteran, Hemipteran, Coleopteran, Dipteran or nematode pest.

As defined herein, the "yield" of the plant refers to the quality and/or quantity of biomass produced by the plant. "Biomass" as used herein refers to any measured plant product. An increase in biomass production is any improvement in the yield of the measured plant product. Increasing plant yield has several commercial applications. For example, increasing plant leaf biomass may increase the yield of leafy vegetables for human or animal consumption. Additionally, increasing leaf biomass can be used to increase production of plant-derived pharmaceutical or industrial products. An increase in yield can comprise any statistically significant increase including, but not limited to, at least a 1% increase, at least a 3% increase, at least a 5% increase, at least a 10% increase, at least a 20% increase, at least a 30%, at least a 50%, at least a 70%, at least a 100% or a greater increase in yield compared to a plant not expressing the pesticidal sequence.

In specific methods, plant yield is increased as a result of improved pest resistance of a plant expressing at least one IPD101 polypeptide disclosed herein. Expression of the IPD101 polypeptide(s) results in a reduced ability of a pest to infest or feed on the plant, thus improving plant yield.

Methods of Processing

Further provided are methods of processing a plant, plant part or seed to obtain a food or feed product from a plant, plant part or seed comprising at least one IPD101 polynucleotide. The plants, plant parts or seeds provided herein, can be processed to yield oil, protein products and/or by-products that are derivatives obtained by processing that have commercial value. Non-limiting examples include transgenic seeds comprising a nucleic acid molecule encoding one or more IPD101 polypeptides which can be processed to yield soy oil, soy products and/or soy by-products.

"Processing" refers to any physical and chemical methods used to obtain any soy product and includes, but is not limited to, heat conditioning, flaking and grinding, extrusion, solvent extraction or aqueous soaking and extraction of whole or partial seeds The following examples are offered by way of illustration and not by way of limitation.

EXAMPLES

Example 1—Identification of an Insecticidal Protein Active Against Western Corn Rootworm (WCRW) from Strain JH70371-1

The insecticidal protein IPD101Aa was identified by protein purification, N-terminal amino acid sequencing, and PCR cloning from bacterial strain JH70371-1 as follows. Insecticidal activity against WCRW was observed from a cell lysate of strain JH70371-1 that was grown in Terrific Broth (BD Difco™, Catalog #243820) and cultured overnight at 28° C. with shaking at 200 rpm. This insecticidal activity exhibited heat and protease sensitivity indicating a proteinaceous nature.

Bioassays with WCRW were conducted using the cell lysate samples mixed with molten low-melt WCRW diet (Frontier Agricultural Sciences, Newark, Del.) in a 96 well format. WCRW neonates were placed into each well of a 96 well plate. The assay was run four days at 25° C. and then was scored for insect mortality and stunting of insect growth. The scores were noted as dead (3), severely stunted (2) (little or no growth but alive), stunted (1) (growth to second instar but not equivalent to controls) or no observed activity (0). Samples demonstrating mortality or severe stunting were further studied.

Genomic DNA of isolated strain JH70371-1 was prepared according to a library construction protocol and sequenced using the Illumina® Genome Analyzer IIx (Illumina Inc., San Diego, Calif.). The nucleic acid contig sequences were assembled and open reading frames were generated. The 16S ribosomal DNA sequence of strain JH70371-1 was BLAST searched against the NCBI database which indicated that this is a *Lysinibacillus* sp.

Cell pellets of strain JH70371-1 were homogenized at ~30,000 psi after re-suspension in 20 mM MOPS buffer, pH 7 with "Complete, EDTA-free" protease inhibitor cocktail (Roche, Indianapolis, Ind.). The crude lysate was cleared by centrifugation and desalted into 20 mM Tris, pH 8.5 using a HiPrep™ 26/10 desalting column (GE Healthcare, Piscataway, N.J.) and then loaded onto a CaptoQ™ column (GE Healthcare, Piscataway, N.J.) equilibrated in 20 mM Tris, pH 8.5 and eluted with a gradient of 0 to 0.4 M NaCl over 30 column volumes (CV). Active fractions were pooled and loaded onto a Superdex™ 200 column (GE Healthcare) equilibrated in 100 mM ammonium bicarbonate. SDS-PAGE analysis of fractions indicated that WCRW activity coincided with a prominent protein band after staining with GelCode® Blue Stain Reagent (Thermo Fisher Scientific®). The protein band was excised, digested with trypsin and analyzed by nano-liquid chromatography/electrospray tandem mass spectrometry (nano-LC/ESI-MS/MS) on a Thermo Q Exactive™ Orbitrap™ mass spectrometer (Thermo Fisher Scientific®, 81 Wyman Street, Waltham, Mass. 02454) interfaced with an Eksigent NanoLC 1-D Plus nano-lc system (AB Sciex™, 500 Old Connecticut Path, Framingham, Mass. 01701). Protein identification was done by database searches using Mascot® (Matrix Science, 10 Perrins Lane, London NW3 1QY UK). The searches against an in-house database and NCBI non-redundant database (nr) identified the novel polypeptide IPD101Aa (SEQ ID NO: 2) which is encoded by the polynucleotide of SEQ ID NO: 1. Cloning and recombinant expression confirmed the insecticidal activity of the IPD101Aa against WCRW.

Example 2—Identification of Homologs of IPD101Aa

In addition to presence in strain JH70371-1, BLAST searches identified several homologs having varying percent amino acid identity to IPD101Aa (SEQ ID NO: 2): IPD101Ab (SEQ ID NO: 4) with 98.2% identity and 99.7% similarity to IPD101Aa was identified in DuPont Pioneer strain PMCH4031E7-1. IPD101Ac (SEQ ID NO: 6) with 97.9% identity and 99.4% similarity to IPD101Aa was identified in DuPont Pioneer strain PMCH4053D11b. IPD101Ba (SEQ ID NO: 8) with 80.9% identity and 89.7% similarity to IPD101Aa was identified in the public NCBI database as gi_928971774_ref_WP_053996211 as a hypothetical protein from *Lysinibacillus macroides*. IPD101Ca (SEQ ID NO: 10) with 77.0% identity and 87.9% similarity to IPD101Aa was identified in the public NCBI database as gi_499133538_ref_WP_010861479 as a hypothetical protein from *Lysinibacillus sphaericus*. In addition, IPD101Cb (SEQ ID NO: 12) was identified in DuPont Pioneer strain AM2685 with 78.2% identity to IPD101Aa. IPD101Cc (SEQ ID NO: 14) with 88.2% identity to IPD101Aa was identified in DuPont Pioneer strain JAPH0723-1. IPD101Cd (SEQ ID NO: 16) with 73.0% identity to IPD101Aa was identified in DuPont Pioneer strain AM11987. IPD101Ce (SEQ ID NO: 18) with 69.4% identity to IPD101Aa was identified in DuPont Pioneer strain DP3525M. IPD101Cf (SEQ ID NO: 20) with 78.8% identity to IPD101Aa was identified in DuPont Pioneer strain BD22. IPD101Ea (SEQ ID NO: 22) with 54.1% identity to IPD101Aa was identified in the public NCBI database as WP_024363526.1 as a hypothetical protein from *Lysinibacillus sphaericus*. IPD101Eb (SEQ ID NO: 24) with 53.5% identity to IPD101Aa was identified in the public NCBI database as AHN24097.1 as a hypothetical protein from *Lysinibacillus varians*. IPD101Ee (SEQ ID NO: 25) with 55.4% identity to IPD101Aa was identified in the public NCBI database as WP_058336899 as a hypothetical protein from *Bacillus* sp. IPD101Fa (SEQ ID NO: 26) with 45.0% identity to IPD101Aa was identified in the public NCBI database as WP_047474321 as a hypothetical protein from *Bacillus amyloliquefaciens*. IPD101Fb (SEQ ID NO: 28) with 44.6% identity to IPD101Aa was identified in DuPont Pioneer strain PMC4018E9-1. IPD101Ga (SEQ ID NO: 29) with 33.7% identity to IPD101Aa was identified in the public NCBI database as WP_050637303 as a hypothetical protein from *Candidatus stoquefichus*. IPD101Gb (SEQ ID NO: 30) with 37.8% identity to IPD101Aa was identified in the public NCBI database as WP_050637304 as a hypothetical protein from *Candidatus stoquefichus*. IPD101Gc (SEQ ID NO: 32) with 32.3% identity to IPD101Aa was identified in the public NCBI database as AL041133 as a hypothetical protein from *Pseudoalteromonas phenolica*. IPD101Gd (SEQ ID NO: 56) with 34.8% identity to IPD101Aa was identified in the public NCBI database as WP_066332372 as a hypothetical protein from *Flavobacterium crassostreae*. IPD101Ge (SEQ ID NO: 58) with 35.1% identity to IPD101Aa was identified in the public NCBI database as WP_066758778 as a hypothetical protein from *Chryseobacterium* sp. IPD101Gf (SEQ ID NO: 60) with 33.7% identity to IPD101Aa was identified in the public NCBI database as WP_063304516 as a hypothetical protein from *Pseudovibrio* sp. The IPD101Aa homologs and the source of the sequence they were identified from are shown in Table 1.

TABLE 1

| Gene Name | Source | Organism | DNA Seq | AA seq |
|---|---|---|---|---|
| IPD101Aa | JH70371 | *Lysinibacillus* sp. | SEQ ID NO: 1 | SEQ ID NO: 2 |
| IPD101Ab | PMCH4031E7-1 | *Lysinibacillus* sp. | SEQ ID NO: 3 | SEQ ID NO: 4 |
| IPD101Ac | PMCH4053D11b | *Lysinibacillus* sp. | SEQ ID NO: 5 | SEQ ID NO: 6 |
| IPD101Ba | NCBI WP_053996211 | *Lysinibacillus macroides* | SEQ ID NO: 7 | SEQ ID NO: 8 |
| IPD101Ca | NCBI WP_010861479.1 | *Lysinibacillus sphaericus* | SEQ ID NO: 9 | SEQ ID NO: 10 |
| IPD101Cb | AM2685 | *Lysinibacillus* sp. | SEQ ID NO: 11 | SEQ ID NO: 12 |
| IPD101Cc | JAPH0723 | *Lysinibacillus* sp. | SEQ ID NO: 13 | SEQ ID NO: 14 |
| IPD101Cd | AM11987 | *Lysinibacillus* sp. | SEQ ID NO: 15 | SEQ ID NO: 16 |
| IPD101Ce | DP3525M | *Bacillus* sp. | SEQ ID NO: 17 | SEQ ID NO: 18 |
| IPD101Cf | BD22 | *Lysinibacillus* sp. | SEQ ID NO: 19 | SEQ ID NO: 20 |
| IPD101Ea | NCBI WP_024363526.1 | *Lysinibacillus sphaericus* | SEQ ID NO: 21 | SEQ ID NO: 22 |
| IPD101Eb | NCBI AHN24097.1 | *Lysinibacillus varians* | SEQ ID NO: 23 | SEQ ID NO: 24 |
| IPD101Ee | NCBI WP_058336899 | *Bacillus* sp. |  | SEQ ID NO: 25 |
| IPD101Fa | NCBI WP_047474321 | *Bacillus amyloliquefaciens* |  | SEQ ID NO: 26 |
| IPD101Fb | PMC4018E9-1 | *Pseudomonas monteilii* | SEQ ID NO: 27 | SEQ ID NO: 28 |

TABLE 1-continued

| Gene Name | Source | Organism | DNA Seq | AA seq |
|---|---|---|---|---|
| IPD101Ga | NCBI WP_050637303 | Candidatus stoquefichus | | SEQ ID NO: 29 |
| IPD101Gb | NCBI WP_050637304 | Candidatus stoquefichus | | SEQ ID NO: 30 |
| IPD101Gc | NCBI AL041133 | Pseudoalteromonas phenolica | SEQ ID NO: 31 | SEQ ID NO: 32 |
| IPD101Gd | WP_066332372 | Flavobacterium crassostreae | SEQ ID NO: 55 | SEQ ID NO: 56 |
| IPD101Ge | WP_066758778 | Chryseobacterium sp. | SEQ ID NO: 57 | SEQ ID NO: 58 |
| IPD101Gf | WP_063304516 | Pseudovibrio sp. | SEQ ID NO: 59 | SEQ ID NO: 60 |

The amino acid sequence identities of the IPD101Aa homologs using the Needlemann-Wunsch algorithm, calculated with a Gap creation penalty: 8 and Gap extension penalty: 2, are shown in Table 2.

sequence was used to design the following primers, AAAGGATCCATGCATACAACAATTGATATTGATCT (IPD101Aa For) (SEQ ID NO: 33) and TTTCTCGAGCT-ATTTTTTAAATGCACGAGC (IPD101Aa Rev) (SEQ ID

TABLE 2

| | IPD101Ab | IPD101Ac | IPD101Ba | IPD101Ca | IPD101Cb | IPD101Cc | IPD101Cd | IPD101Ce | IPD101Cf | IPD101Ea |
|---|---|---|---|---|---|---|---|---|---|---|
| IPD101Aa | 98.2 | 97.9 | 80.9 | 77.0 | 78.2 | 78.8 | 73.3 | 69.4 | 78.8 | 54.1 |
| IPD101Ab | — | 97.9 | 80.9 | 76.4 | 77.6 | 78.2 | 73.0 | 69.7 | 78.2 | 53.8 |
| IPD101Ac | — | — | 81.2 | 75.8 | 77.3 | 77.9 | 72.4 | 69.1 | 77.6 | 53.8 |
| IPD101Ba | — | — | — | 82.1 | 82.7 | 82.1 | 76.7 | 72.7 | 80.6 | 56.3 |
| IPD101Ca | — | — | — | — | 92.7 | 93.3 | 81.5 | 75.5 | 90.6 | 58.1 |
| IPD101Cb | — | — | — | — | — | 97.0 | 82.4 | 74.5 | 88.2 | 60.1 |
| IPD101Cc | — | — | — | — | — | — | 81.2 | 75.4 | 88.5 | 59.0 |
| IPD101Cd | — | — | — | — | — | — | — | 71.1 | 80.6 | 59.4 |
| IPD101Ce | — | — | — | — | — | — | — | — | 75.5 | 56.8 |
| IPD101Cf | — | — | — | — | — | — | — | — | — | 57.7 |
| IPD101Ea | — | — | — | — | — | — | — | — | — | — |
| IPD101Eb | — | — | — | — | — | — | — | — | — | — |
| IPD101Ee | — | — | — | — | — | — | — | — | — | — |
| IPD101Fa | — | — | — | — | — | — | — | — | — | — |
| IPD101Fb | — | — | — | — | — | — | — | — | — | — |
| IPD101Ga | — | — | — | — | — | — | — | — | — | — |
| IPD101Gb | — | — | — | — | — | — | — | — | — | — |
| IPD101Gc | — | — | — | — | — | — | — | — | — | — |
| IPD101Gd | — | — | — | — | — | — | — | — | — | — |
| IPD101Ge | — | — | — | — | — | — | — | — | — | — |
| IPD101Gf | — | — | — | — | — | — | — | — | — | — |

| | IPD101Eb | IPD101Ee | IPD101Fa | IPD101Fb | IPD101Ga | IPD101Gb | IPD101Gc | IPD101Gd | IPD101Ge | IPD101Gf |
|---|---|---|---|---|---|---|---|---|---|---|
| IPD101Aa | 53.5 | 55.4 | 45.0 | 44.6 | 33.7 | 37.8 | 32.3 | 36.8 | 36.0 | 35.8 |
| IPD101Ab | 53.2 | 56.5 | 45.5 | 44.6 | 34.3 | 38.1 | 32.0 | 37.1 | 36.3 | 35.6 |
| IPD101Ac | 53.2 | 55.4 | 45.0 | 44.4 | 33.7 | 38.5 | 32.0 | 37.1 | 36.3 | 35.6 |
| IPD101Ba | 55.7 | 54.6 | 45.5 | 44.9 | 34.9 | 35.8 | 30.5 | 38.0 | 38.0 | 35.6 |
| IPD101Ca | 58.1 | 55.2 | 46.3 | 43.9 | 33.4 | 37.6 | 30.2 | 38.7 | 37.6 | 36.0 |
| IPD101Cb | 59.8 | 54.9 | 45.8 | 44.6 | 32.9 | 36.6 | 29.9 | 39.8 | 37.0 | 36.0 |
| IPD101Cc | 58.7 | 53.8 | 45.5 | 45.6 | 33.4 | 36.3 | 29.8 | 38.8 | 37.0 | 36.3 |
| IPD101Cd | 58.8 | 56.9 | 46.3 | 42.7 | 32.8 | 34.6 | 29.3 | 37.2 | 36.3 | 34.7 |
| IPD101Ce | 56.5 | 55.2 | 48.2 | 43.2 | 33.1 | 37.8 | 31.7 | 38.0 | 35.6 | 35.3 |
| IPD101Cf | 57.4 | 55.5 | 44.4 | 45.0 | 34.6 | 38.3 | 30.2 | 38.2 | 36.6 | 37.1 |
| IPD101Ea | 99.4 | 51.4 | 46.5 | 40.9 | 31.3 | 35.0 | 31.6 | 35.7 | 34.3 | 32.2 |
| IPD101Eb | — | 51.2 | 46.2 | 40.6 | 31.3 | 34.7 | 31.2 | 35.7 | 33.7 | 32.0 |
| IPD101Ee | — | — | 48.4 | 36.6 | 31.7 | 33.2 | 28.2 | 33.8 | 31.9 | 30.2 |
| IPD101Fa | — | — | — | 33.4 | 31.0 | 35.2 | 29.2 | 30.5 | 30.6 | 30.3 |
| IPD101Fb | — | — | — | — | 31.5 | 33.0 | 28.7 | 35.6 | 35.5 | 36.8 |
| IPD101Ga | — | — | — | — | — | 38.2 | 29.6 | 29.7 | 28.2 | 33.4 |
| IPD101Gb | — | — | — | — | — | — | 29.2 | 32.8 | 36.2 | 31.2 |
| IPD101Gc | — | — | — | — | — | — | — | 28.4 | 27.9 | 29.4 |
| IPD101Gd | — | — | — | — | — | — | — | — | 78.6 | 30.7 |
| IPD101Ge | — | — | — | — | — | — | — | — | — | 33.1 |
| IPD101Gf | — | — | — | — | — | — | — | — | — | — |

Example 3—Cloning and Expression of IPD101Aa in *E. coli*

An open reading frame containing the IPD101Aa coding sequence was identified in the genomic sequence of stain JH70371 using peptide fragments from MS analysis. This NO: 34), to subclone the IPD101Aa coding sequence into the pET-28a vector (Novagen) using the BamHI/XhoI restriction sites in frame with an N-terminal 6×-His tag and the IPD101Aa native stop codon (TAG). The KOD Hot Start Master Mix (EMD Biosciences, San Diego, Calif.) was used for PCR amplification of the IPD101Aa gene on a BioRad C1000 Touch thermal cycler. Amplicons were gel purified, ligated (T4 DNA Ligase, New England BioLabs, Ipswich, Mass.) into the BamHI/XhoI digested pET28a, transformed into *E. coli* TOP10 high efficiency chemically competent cells (Invitrogen) and clones were confirmed by sequencing.

The IPD101Aa N-terminal 6×-His tagged construct was transformed into chemically competent BL21 (DE3) cells (Invitrogen) and grown overnight at 37° C. with kanamycin selection and then inoculated to a fresh 2×YT medium (1:100) and further grown to an optical density of about 0.8-1.2. Protein expression was induced by adding 1.0 mM IPTG and cells were further grown at 16° C. for 16 hours. The *E. coli* expressed proteins were purified by immobilized metal ion chromatography (IMAC) using Talon Cobalt resin (Clonetech: Mountain View, Calif.) according to the manufacturer's protocols. The purified 1.5 mL fractions eluted in 250 mM imidazole were dialyzed into PBS buffer using 6K MWCO Flextubes (IBI: Peosta, Iowa) overnight on a stir plate at 4° C. The dialyzed protein was run in diet assays to evaluate the insecticidal protein effects on larvae of a diversity of Lepidoptera and Coleoptera. Purified and desalted IPD101Aa N-terminal 6×-His tagged protein was submitted to bioassay against WCRW and was found to be active as shown in Table 4 below.

Example 4—Cloning of IPD101Aa Homologs IPD101Cb, Cc, Cd, Ce and Cf

Genes with sequence similarity to the polynucleotide sequence for IPD101Aa (SEQ ID NO: 1) identified from internal databases were PCR amplified from DNA prepared from the source organism (Table 1) using the primers designed to the coding sequences of each homolog (Table 3). All primers contained greater than 30 nucleotides of homology to pET28a (Novagen) or a modified version of pET28a. The PCR products were gel purified, assembled using the Gibson Assembly Cloning Kit (New England Biolabs, Ipswich, Mass.) with the expression vectors having the matching overlap sequence, transformed into *E. coli* TOP10 high efficiency chemically competent cells (Invitrogen) and clones were confirmed by sequencing. Purified and desalted IPD101 N-terminal 6×-His tagged homolog protein was submitted to bioassay against WCRW and was observed to have activity as referenced below (Table 4 below).

TABLE 3

PCR primers used to clone homologs of IPD101Aa.

| Gene Name | Forward Primer SEQ ID | Forward Primer | Reverse Primer SEQ ID | Reverse Primer |
|---|---|---|---|---|
| IPD101Cb | SEQ ID NO: 43 | ACTGGTGGACAGCAAA TGGGTCGCGGATCCATG CAMACTACAATTGATA TCGATCTTAA | SEQ ID NO: 44 | CTCGAGTGCGGCCGCAAGC TTTTAGGCTTTAAATGCTCG TGCAACGTAATA |
| IPD101Cc | SEQ ID NO: 41 | ACTGGTGGACAGCAAA TGGGTCGCGGATCCATG CAMACTACAATTGATA TCGATCTTAA | SEQ ID NO: 42 | CTCGAGTGCGGCCGCAAGC TTTTATGCTTTAAATGCTCG TGCTACGTAGTA |
| IPD101Cd | SEQ ID NO: 37 | ACTGGTGGACAGCAAA TGGGTCGCGGATCCATG CAMACTACAATTGATA TCGATCTTAA | SEQ ID NO: 38 | CTCGAGTGCGGCCGCAAGC TTCTATGCTTTATATGCGCG TGCTACATAATA |
| IPD101Ce | SEQ ID NO: 39 | CCGCGCGGCAGCATCG AGGGAAGGCATATGCA AATTKCACATGATATTG ATTTAAGG | SEQ ID NO: 40 | CTTTCGACTGAGCCTTTCGT TTTACTCGAGTTATGATCGA TATGCACGAGCAACGTAGTA |
| IPD101Cf | SEQ ID NO: 35 | ACTGGTGGACAGCAAA TGGGTCGCGGATCCATG CAMACTACAATTGATA TCGATCTTAA | SEQ ID NO: 36 | CTCGAGTGCGGCCGCAAGC TTTTAAGCTTTATATGCTCG TGCTACGTAATA |

Example 5—Cloning of IPD101Aa Homologs IPD101Ca, Ea, and Eb

The IPD101Ca, IPD101Ea, and IPD101Eb amino acid sequences were identified by a BLAST search of the public non-redundant protein sequence database (Table 1). The corresponding coding sequences (SEQ ID NO: 9, SEQ ID NO: 21, and SEQ ID NO: 23, respectively) were generated as synthetic DNA fragments with BamHI/XhoI restriction sites, ligated into pET28a (Novagen) digested with BamHI/XhoI, transformed into *E. coli* TOP10 high efficiency chemically competent cells (Invitrogen), and confirmed by sequencing. Purified and desalted IPD101 N-terminal 6×-His tagged homolog protein was submitted to bioassay against WCRW, and activity results are presented below (Table 4 below).

TABLE 4

| Protein | Top_Dose | Assay type | WCRW | FAW | CEW | ECB | SBL | BCW | VBC | SCRW |
|---|---|---|---|---|---|---|---|---|---|---|
| IPD101Aa | 1200 ppm | incorp | Yes | No | Yes | No | No | No | Yes | Yes |
| IPD101Ca | 1500 ppm | incorp | Yes | No | Yes | Yes | Yes | No | No | NT |
| IPD101Cb | 333 ppm | incorp | Yes | NT | NT | NT | NT | NT | NT | NT |
| IPD101Cc | 1199 ppm | incorp | Yes | NT | NT | NT | NT | NT | NT | NT |
| IPD101Cd | 453 ppm | incorp | No | NT | NT | NT | NT | NT | NT | NT |
| IPD101Ce | 156 ppm | incorp | Yes | NT | NT | NT | NT | NT | NT | NT |
| IPD101Cf | 409 ppm | incorp | Yes | NT | NT | NT | NT | NT | NT | NT |
| IPD101Ea | 1125 µg/cm² | overlay | No | No | No | No | No | No | No | NT |
| IPD101Eb | 20 µg/cm² | overlay | No | No | No | No | No | No | No | NT |

"NT" denotes not tested;
"WCRW" denotes Western Corn Rootworm;
"FAW" denotes Fall Armyworm;
"CEW" denotes Corn Earworm;
"ECB" denotes Eastern Corn Borer;
"SBL" denotes Soybean Looper;
"BCW" denotes Black Cutworm;
"VBC" denotes Velvet Bean Caterpillar;
"SCRW" denotes Southern Corn Rootworm.

Example 6—Chimeras Between IPD101 Homologs

To generate active variants with diversified sequences, chimeras between IPD101Aa (SEQ ID NO: 2) and IPD101Cc (SEQ ID NO: 14) polypeptides were generated by multi-PCR fragment overlap assembly. A total of five chimeras between IPD101Aa and IPD101Cc were constructed and cloned into pET28a with an N-terminal 6× histidine tag as described in Example 4. Constructs were transformed into BL21 DE3 and cultured for protein expression. Cell lysates were generated using B-PER® Protein Extraction Reagent from Thermo Scientific (3747 N. Meridian Rd., Rockford, Ill. USA 61101) and screened for WCRW insecticidal activity. Table 5 shows the chimera boundaries and the % sequence identity to IPD101Aa (SEQ ID NO: 2) as calculated using the Needlemann-Wunsch algorithm with a Gap creation penalty: 8 and Gap extension penalty: 2.

TABLE 5

Percent sequence identity of chimeras to IPD101Aa.

| Chimera Designation | Polynucleotide | % Seq. identity to IPD101Aa (SEQ ID NO: 2) | WCRW active |
|---|---|---|---|
| Chimera 23 SEQ ID NO: 46 | SEQ ID NO: 45 | 97 | Yes |
| Chimera 27 SEQ ID NO: 48 | SEQ ID NO: 47 | 90 | Yes |
| Chimera 29 SEQ ID NO: 50 | SEQ ID NO: 49 | 95 | Yes |
| Chimera 41 SEQ ID NO: 52 | SEQ ID NO: 51 | 87 | Yes |
| Chimera 44 SEQ ID NO: 54 | SEQ ID NO: 53 | 82 | Yes |

Example 7—Diet-Based Bioassays with Corn Rootworm for Determination of LC50 and IC50

Standardized corn rootworm diet incorporation bioassays similar to Zhao, J.-Z. et al. (J. Econ. Entomol. 109: 1369-1377 (2016)) were utilized to test the activity of the IPD101Aa polypeptide (SEQ ID NO: 2) against WCRW. Corn rootworm diet was prepared according to manufacturer's guideline for *Diabrotica* diet (Frontier, Newark, Del.). The test involved six different IPD101Aa polypeptide doses plus buffer control with 32 observations for each dose in each bioassay. Neonates were infested into 96-well plates containing a mixture of the IPD101Aa polypeptide (5 µL/well) and diet (25 µL/well), each well with approximately 5 to 8 larvae (<24 h post hatch). After one day a single larva was transferred into each well of a second 96-well plate containing a mixture of the IPD101Aa polypeptide (20 µL/well) and diet (100 µL/well) at the same concentration as the treatment to which the insect was exposed on the first day. For NCRW assays, two neonates were infested directly into each well of a 96-well plate containing a mixture of the IPD101Aa polypeptide (20 µL/well) and diet (100 µL/well).

The plates were incubated at 27° C., 65% RH in the dark for 6 days. The plates with a single WCRW larva per well were scored as dead, severely stunted (>60% reduction in size compared to control larvae) or not affected. The plates infested with two NCRW larvae per well were scored based on the least affected individual for each well. The mortality data were analyzed by the PROBIT procedure in SAS software (Version 9.4, SAS Institute. Cary, N.C., USA) to determine the lethal concentrations affecting 50% of larvae ($LC_{50}$). Similarly, the total numbers of dead and severely stunted larvae were used to calculate the growth inhibition concentrations affecting 50% of the larvae ($IC_{50}$).

The LC50 and IC50 against WCRW (*Diabrotica virgifera virgifera*) were 5.1 ppm and 3.0 ppm, respectively and against NCRW (*Diabrotica barberi*) were 54.2 ppm and 11.6 ppm, respectively. The results are shown in Table 6.

TABLE 6

Diet-based bioassays of IPD101Aa on WCRW and NCRW.

| Insect | LC/IC | N-6xHis IPD101Aa (µg/mL, 6 d) | 95% CL | Slope | N |
|---|---|---|---|---|---|
| WCRW* | LC50 | 5.1 | 3.3-7.2 | 2.2 | 159 |
|  | IC50 | 3.0 | 2.1-3.9 | 3.6 | 127 |
| NCRW** | LC50 | 54.2 | 41.5-68.8 | 2.5 | 244 |
|  | IC50 | 11.6 | 7.3-14.0 | 4.3 | 212 |

*One larva per well method;
**Two larvae per well method.

Example 8—Mode of Action

Bioactivity of purified recombinant protein incorporated into artificial diet revealed toxicity of IPD101Aa (SEQ ID NO: 2) to WCRW larvae. To understand the mechanism of IPD101Aa toxicity, specific binding of the purified protein with WCRW midgut tissue was evaluated by in vitro competition assays. Midguts were isolated from third instar WCRW larvae to prepare brush border membrane vesicles (BBMV) following a method modified from Wolfersberger et al. (Comp Bioch Physiol 86A: 301-308 (1987)) using amino-peptidase activity to track enrichment. BBMVs represent the apical membrane component of the epithelial cell lining of insect midgut tissue and therefore serve as a model system for how insecticidal proteins interact within the gut following ingestion.

Recombinant IPD101Aa was expressed and purified from an E. coli expression system utilizing a carboxy-terminal poly-histidine fusion tag (6×His). The full length purified protein (SEQ ID NO: 2) was labeled with Alexa-Fluor® 488 (Life Technologies) and unincorporated fluorophore was separated from labeled protein using buffer exchange resin (Life Technologies, A30006) following manufacturer's recommendations. Prior to binding experiments, proteins were quantified by gel densitometry following Simply Blue® (Thermo Scientific) staining of SDS-PAGE resolved samples that included BSA as a standard.

Binding buffer consisted of PBS supplemented with 0.1% of Tween 20, pH 7.4. To demonstrate specific binding and to evaluate affinity, BBMVs (1 μg) were incubated with Alexa-labeled IPD101Aa (1.5 nM) in 100 μL of Binding buffer for 1 h at RT in the absence and presence of increasing concentrations of unlabeled IPD101Aa. Centrifugation at 20,000×g was used to pellet the BBMVs to separate unbound toxin remaining in solution. The BBMV pellet was then washed twice with Binding buffer to eliminate remaining unbound toxin. The final BBMV pellet (with bound fluorescent toxin) was solubilized in reducing Laemmli sample buffer, heated to 100° C. for 5 minutes, and subjected to SDS-PAGE using 4-12% Bis-Tris polyacrylamide gels (Life Technologies). The amount of Alexa-labeled IPD101Aa in the gel from each sample was measured by a digital fluorescence imaging system (Image Quant LAS4000 GE Healthcare). Digitized images were analyzed by densitometry software (Phoretix 1D, TotalLab, Ltd.).

The apparent affinity of IPD101Aa for WCRW BBMVs was estimated based on the concentration of unlabeled protein that was needed to reduce the binding of Alexa-labeled IPD101Aa by 50% (EC50 value). This value was approximately 2 nM for IPD101Aa binding with WCR BBMVs (FIG. 2).

The above description of various illustrated embodiments of the disclosure is not intended to be exhaustive or to limit the scope to the precise form disclosed. While specific embodiments of and examples are described herein for illustrative purposes, various equivalent modifications are possible within the scope of the disclosure, as those skilled in the relevant art will recognize. The teachings provided herein can be applied to other purposes, other than the examples described above. Numerous modifications and variations are possible in light of the above teachings and, therefore, are within the scope of the appended claims.

These and other changes may be made in light of the above detailed description. In general, in the following claims, the terms used should not be construed to limit the scope to the specific embodiments disclosed in the specification and the claims.

The entire disclosure of each document cited (including patents, patent applications, journal articles, abstracts, manuals, books or other disclosures) in the Background, Detailed Description, and Examples is herein incorporated by reference in their entireties.

Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight; temperature is in degrees centigrade; and pressure is at or near atmospheric.

That which is claimed is:

1. A DNA construct comprising a heterologous regulatory element and a polynucleotide encoding a polypeptide having at least 95% sequence identity to the amino acid sequence of SEQ ID NO: 2, SEQ ID NO: 4, SEQ ID NO: 6, SEQ ID NO: 46, or SEQ ID NO: 50, wherein the polypeptide has insecticidal activity.

2. A transgenic plant or plant cell comprising the DNA construct of claim 1.

3. A method for controlling an insect pest population, comprising contacting the insect pest population with a polypeptide having at least 95% sequence identity to the amino acid sequence of SEQ ID NO: 2, SEQ ID NO: 4, SEQ ID NO: 6, SEQ ID NO: 46, or SEQ ID NO: 50, wherein the polypeptide has insecticidal activity.

4. A method of inhibiting growth or killing an insect pest, comprising contacting the insect pest with a composition comprising a polypeptide having at least 95% sequence identity to the amino acid sequence of SEQ ID NO: 2, SEQ ID NO: 4, SEQ ID NO: 6, SEQ ID NO: 46, or SEQ ID NO: 50, wherein the polypeptide has insecticidal activity.

5. The method of inhibiting growth or killing an insect pest of claim 4, wherein the insect pest is a Lepidoptera and/or Coleoptera insect pest.

6. A method for controlling an insect pest population, comprising contacting the insect pest population with the transgenic plant or plant cell of claim 2.

7. A method of inhibiting growth or killing an insect pest, comprising transforming a plant with the DNA construct of claim 1, further comprising contacting the insect pest with the transgenic plant or plant cell.

8. The method of claim 7, wherein the insect pest is Western Corn Rootworm (*Diabrotica virgifera virgifera*).

9. The method of claim 4 wherein the insect pest or insect pest population is resistant to at least one Bt toxin.

* * * * *

SEQUENCE LISTING

```
<160> NUMBER OF SEQ ID NOS: 61

<210> SEQ ID NO 1
<211> LENGTH: 987
<212> TYPE: DNA
<213> ORGANISM: Lysinibacillus sp.

<400> SEQUENCE: 1
atgcatacaa caattgatat tgatcttaaa ttaaaacagg gatttcgaac tttatttcca      60
gaatacgcag caaaattaga gaaagctact tctcaagtgg aaatcaataa gcttcaagcg     120
gaattcattg aggaacgaaa gcaaatatta gctgaagctt taggcaagga tatatctgag     180
ctaaaagcaa gtgatcagac agcaccaatt ccattgtctg gggacacgta taaaatgctt     240
atcaatgcaa caggtgatga cattaaaaga cagcttcatg ttctgataga tggtcttgaa     300
cgattaaaag gaatggaaaa agatgaagct ggtcttgtga ctgcacaaat tgtactttct     360
ggtgcgttag gaattggatc tttagcaacg attgaagttg taagaaactt agcaatgggt     420
gcggcagaaa cagtggctgc ctttgctgga gtaacagttg caacagttgg agtagttgta     480
gcagttgcat ctcttgtaat tgtgggtgtt attatcccaa ttatttactt tatgcaaaaa     540
ccagcaaatg ctattgtact tttaatcaat gaattggacg aacctcttgt atttgaaaca     600
gagcataatg ttcatggtaa accaatgtta atgacaacgc caattcctaa aggagtcgtg     660
```

```
attcctggtg taggtacata tgctactgca ggatttatcg caaccgaaaa aagagaaaat    720
gctttagtgg aacacaata tggttttaca atgcgatata aagatactaa attatctttt    780
ggtgttgaat gtccttaac agctatttat actgataata attgttattg tgccatagat    840
gaaagtgctg tgacagttgc agaaatgact acaaaaaaga ataagcaata ttgggagcat    900
aataaaaacg gcataggatt gagcattcgt tgcaactctg gaagtggatc aatagcttat    960
tacgtagctc gtgcatttaa aaaatag                                       987
```

<210> SEQ ID NO 2
<211> LENGTH: 328
<212> TYPE: PRT
<213> ORGANISM: Lysinibacillus sp.

<400> SEQUENCE: 2

```
Met His Thr Thr Ile Asp Ile Asp Leu Lys Leu Lys Gln Gly Phe Arg
1               5                   10                  15

Thr Leu Phe Pro Glu Tyr Ala Ala Lys Leu Glu Lys Ala Thr Ser Gln
            20                  25                  30

Val Glu Ile Asn Lys Leu Gln Ala Glu Phe Ile Glu Glu Arg Lys Gln
        35                  40                  45

Ile Leu Ala Glu Ala Leu Gly Lys Asp Ile Ser Glu Leu Lys Ala Ser
    50                  55                  60

Asp Gln Thr Ala Pro Ile Pro Leu Ser G

Tyr Val Ala Arg Ala Phe Lys Lys
            325

<210> SEQ ID NO 3
<211> LENGTH: 984
<212> TYPE: DNA
<213> ORGANISM: Lysinibacillus sp.

<400> SEQUENCE: 3

```
atgcatacaa caattgatat tgatcttaaa ttaaaacagg gatttcgaac tttatttcca      60
gaatacgcag caaaattaga gaaagctact tctcaagtgg aaatcaataa gcttcaagcg     120
gaattcattg aggaacgaaa gcaaatatta gctgaagctt taggcaagga tatatctgag     180
ctaaaagcaa gtgatcagac agcaccaatt ccattgtctg ggacacgta taaaacgctt      240
atcaatgcaa caggtgatga cattaaaaga cagcttcatg ttctgataga tggtcttgaa     300
cgattaaaag gaatggaaaa agatgaagct ggtcttgtga ctgcacaaat tgttctttct     360
ggtgcattag ggattggatc tttagcaacg attgaagtta taagaaactt agcgatgggt     420
gcggcagaaa cagttgctgc ctttgctgga gtaacagttg caacagttgg agtagttgta     480
gcagttgcat ctcttgtgat tgtgggtgtt attatcccaa ttatttattt tatgcaaaaa     540
ccggcaaatg ctattgtact tttaatcaat gaattggacg aaccacttgt atttgaaaca     600
gatcacaatg ttcacggtaa accaatgtta atgacaacgc caattcctaa aggagtcgtg     660
attcctggtg taggtacata tgctactgca ggatttatag caaccgaaaa agagaaaat      720
gctttagtag gaacacaata tggttttaca atgcgatata aagatactaa attatctttt     780
ggtgttgaat gtcctttaac agctatttat actgataata attgttattg tgccataaat     840
gaaagtgctg tgacagttgc agaaatgact acaaaaaaga atcagcaata ttgggagcat     900
cataaaaacg gtataggatt gagcattcgt tgcaactctg aagtggatc aatagcttat      960
tacgtagctc gtgcatttaa aaaa                                            984
```

<210> SEQ ID NO 4
<211> LENGTH: 328
<212> TYPE: PRT
<213> ORGANISM: Lysinibacillus sp.

<400> SEQUENCE: 4

Met His Thr Thr Ile Asp Ile Asp Leu Lys Leu Lys Gln Gly Phe Arg
1               5                   10                  15

Thr Leu Phe Pro Glu Tyr Ala Ala Lys Leu Glu Lys Ala Thr Ser Gln
            20                  25                  30

Val Glu Ile Asn Lys Leu Gln Ala Glu Phe Ile Glu Glu Arg Lys Gln
        35                  40                  45

Ile Leu Ala Glu Ala Leu Gly Lys Asp Ile Ser Glu Leu Lys Ala Ser
    50                  55                  60

Asp Gln Thr Ala Pro Ile Pro Leu Ser Gly Asp Thr Tyr Lys Thr Leu
65                  70                  75                  80

Ile Asn Ala Thr Gly Asp Asp Ile Lys Arg Gln Leu His Val Leu Ile
                85                  90                  95

Asp Gly Leu Glu Arg Leu Lys Gly Met Glu Lys Asp Glu Ala Gly Leu
            100                 105                 110

Val Thr Ala Gln Ile Val Leu Ser Gly Ala Leu Gly Ile Gly Ser Leu
        115                 120                 125

```
Ala Thr Ile Glu Val Ile Arg Asn Leu Ala Met Gly Ala Ala Glu Thr
    130                 135                 140

Val Ala Ala Phe Ala Gly Val Thr Val Ala Thr Val Gly Val Val Val
145                 150                 155                 160

Ala Val Ala Ser Leu Val Ile Val Gly Val Ile Ile Pro Ile Ile Tyr
                165                 170                 175

Phe Met Gln Lys Pro Ala Asn Ala Ile Val Leu Leu Ile Asn Glu Leu
            180                 185                 190

Asp Glu Pro Leu Val Phe Glu Thr Asp His Asn Val His Gly Lys Pro
        195                 200                 205

Met Leu Met Thr Thr Pro Ile Pro Lys Gly Val Val Ile Pro Gly Val
    210                 215                 220

Gly Thr Tyr Ala Thr Ala Gly Phe Ile Ala Thr Glu Lys Arg Glu Asn
225                 230                 235                 240

Ala Leu Val Gly Thr Gln Tyr Gly Phe Thr Met Arg Tyr Lys Asp Thr
                245                 250                 255

Lys Leu Ser Phe Gly Val Glu Cys Pro Leu Thr Ala Ile Tyr Thr Asp
            260                 265                 270

Asn Asn Cys Tyr Cys Ala Ile Asn Glu Ser Ala Val Thr Val Ala Glu
        275                 280                 285

Met Thr Thr Lys Lys Asn Gln Gln Tyr Trp Glu His His Lys Asn Gly
    290                 295                 300

Ile Gly Leu Ser Ile Arg Cys Asn Ser Gly Ser Gly Ser Ile Ala Tyr
305                 310                 315                 320

Tyr Val Ala Arg Ala Phe Lys Lys
                325

<210> SEQ ID NO 5
<211> LENGTH: 987
<212> TYPE: DNA
<213> ORGANISM: Lysinibacillus sp.

<400> SEQUENCE: 5
atgaatacaa caattgatat tgatcttaaa ttaaaagagg ggtttcgaac attatttcct      60
gaatacgcag caaaattaga gaaagctact tctcaagtgg aaattaatac gcttcaagcg     120
gaattcattg aggaacgaaa gcaaatatta gcagaagctc taggcaagga tatatctgag     180
ctaaaagcaa gtgatcagac agcaccaatt ccattgtctg ggacatgtta taaaatgctt     240
atcaatgcaa caggtgatga cattaaaaga cagcttcatg ttctgataga tggtcttgaa     300
cgattaaaag gaatggaaaa agatgaagct ggtcttgtga ctgcacaaat tgttctttct     360
ggtgcattag ggattggatc tttagcaacg attgaagttg taagaaactt agcgatgggt     420
gcggcagaaa cagtggctgc ctttgctgga gtaacagttg caacagttgg agtagttgta     480
gcagttgcat ctcttgtgat tgtgggtgtt attatcccaa ttatttattt tatgcaaaaa     540
ccagcaaatg ctattgtact tttaatcaat gaattagacg aacctcttgt atttgaaaca     600
gatcacaatg ttcatggtaa accaatgtta atgacaacac caattcctaa aggagtcgtg     660
attcctggtg taggtacata tgctactgca ggatttatag caactgaaaa aagagaaaat     720
gctttagtag gaacacaata tggttttaca atgcgatata aagatactaa attatctttt     780
ggtgttgaat gtcctttaac agctatttat actgataata attgttattg tgccatagat     840
gaaagtgctg tgacagttgc agaaatgact acaaaaaaga atcagcaata ttgggagcat     900
cataaaaacg gtataggatt gagcattcgt tgcaactctg gaagtggatc aatagcttat     960
 tacgtagctc gtgcatttaa aaaatag                                                                987

<210> SEQ ID NO 6
<211> LENGTH: 328
<212> TYPE: PRT
<213> ORGANISM: Lysinibacillus sp.

<400> SEQUENCE: 6

Met Asn Thr Thr Ile Asp Ile Asp Leu Lys Leu Lys Glu Gly Phe Arg
1               5                   10                  15

Thr Leu Phe Pro Glu Tyr Ala Ala Lys Leu Glu Lys Ala Thr Ser Gln
            20                  25                  30

Val Glu Ile Asn Thr Leu Gln Ala Glu Phe Ile Glu Arg Lys Gln
        35                  40                  45

Ile Leu Ala Glu Ala Leu Gly Lys Asp Ile Ser Glu Leu Lys Ala Ser
    50                  55                  60

Asp Gln Thr Ala Pro Ile Pro Leu Ser Gly Asp Met Tyr Lys Met Leu
65                  70                  75                  80

Ile Asn Ala Thr Gly Asp Asp Ile Lys Arg Gln Leu His Val Leu Ile
                85                  90                  95

Asp Gly Leu Glu Arg Leu Lys Gly Met Glu Lys Asp Glu Ala Gly Leu
            100                 105                 110

Val Thr Ala Gln Ile Val Leu Ser Gly Ala Leu Gly Ile Gly Ser Leu
        115                 120                 125

Ala Thr Ile Glu Val Val Arg Asn Leu Ala Met Gly Ala Ala Glu Thr
130                 135                 140

Val Ala Ala Phe Ala Gly Val Thr Val Ala Thr Val Gly Val Val Val
145                 150                 155                 160

Ala Val Ala Ser Leu Val Ile Val Gly Val Ile Pro Ile Ile Tyr
                165                 170                 175

Phe Met Gln Lys Pro Ala Asn Ala Ile Val Leu Leu Ile Asn Glu Leu
            180                 185                 190

Asp Glu Pro Leu Val Phe Glu Thr Asp His Asn Val His Gly Lys Pro
        195                 200                 205

Met Leu Met Thr Thr Pro Ile Pro Lys Gly Val Ile Pro Gly Val
    210                 215                 220

Gly Thr Tyr Ala Thr Ala Gly Phe Ile Ala Thr Glu Lys Arg Glu Asn
225                 230                 235                 240

Ala Leu Val Gly Thr Gln Tyr Gly Phe Thr Met Arg Tyr Lys Asp Thr
                245                 250                 255

Lys Leu Ser Phe Gly Val Glu Cys Pro Leu Thr Ala Ile Tyr Thr Asp
            260                 265                 270

Asn Asn Cys Tyr Cys Ala Ile Asp Glu Ser Ala Val Thr Val Ala Glu
        275                 280                 285

Met Thr Thr Lys Lys Asn Gln Gln Tyr Trp Glu His His Lys Asn Gly
    290                 295                 300

Ile Gly Leu Ser Ile Arg Cys Asn Ser Gly Ser Gly Ser Ile Ala Tyr
305                 310                 315                 320

Tyr Val Ala Arg Ala Phe Lys Lys
                325

<210> SEQ ID NO 7
<211> LENGTH: 993
<212> TYPE: DNA
<213> ORGANISM: Lysinibacillus macroides

<400> SEQUENCE: 7

```
atgcatacta cacttgatat tgattttaaa ttaaaagaag gatttcgttc tttattccct      60
gattatgcaa caaaactaga gaaagcaact tcacaagaag aaattaatag atttcaggct     120
gaatttatag aggaaagaaa acaaattttg gcggaagcgc taggcaagga tatatccgag     180
ctagaggcaa gcgatcagac tgcacccatt ccactgaaac aagatatgta taaaattctt     240
atcaatgcta ctggtgatga tattaaaaaa caactccatg tgctgattga tggtttaaat     300
cgattgcaag gaatggaaga tgatgacgct ggtcttgtta ctgcacaaat tcttgtttcg     360
ggtgcattag gaattggtct attatcaacc tctactgtta ttgcaaaatt ggcagttgga     420
gcagccgaag cagtcgcagc ttttgctggt gttacagttg cttcagttgg tgcagttgta     480
gccattgctg ctctagtaat tgtggctatt atcatcccaa ttatttattt tatggcaaaa     540
ccagcaaatg cgattgtgtt gttaattaat gaattggaca agcctcttac ttttgtatca     600
gatcataatg ttcatggtaa accaatgtta atgacaacgc caattcctga agctgttgtg     660
attcctgaag tgggtacata tccagtatca ggattgattg caacagaaaa gagagaaaac     720
gctttagtag gcacacaata cggatttacc atgcagtatg aggtacagat acgaagcttt     780
tctttcggtg tagaatgtcc tttaacgggt atctatacag ataataattg ttattgtgct     840
atagatgaaa gtgcgagtac agttgccgaa atgactacaa aacagaataa acagttttgg     900
gaagatgaga aaaatggtat caaattaagc attcgttgca actctggaag cggatcgata     960
gcttattatg tagcgcgagc gtatagagga tag                                  993
```

<210> SEQ ID NO 8
<211> LENGTH: 330
<212> TYPE: PRT
<213> ORGANISM: Lysinibacillus macroides

<400> SEQUENCE: 8

```
Met His Thr Thr Leu Asp Ile Asp Phe Lys Leu Lys Glu Gly Phe Arg
1               5                  10                  15

Ser Leu Phe Pro Asp Tyr Ala Thr Lys Leu Glu Lys Ala Thr Ser Gln
            20                  25                  30

Glu Glu Ile Asn Arg Phe Gln Ala Glu Phe Ile Glu Glu Arg Lys Gln
        35                  40                  45

Ile Leu Ala Glu Ala Leu Gly Lys Asp Ile Ser Glu Leu Glu Ala Ser
    50                  55                  60

Asp Gln Thr Ala Pro Ile Pro Leu Lys Gln Asp Met Tyr Lys Ile Leu
65                  70                  75                  80

Ile Asn Ala Thr Gly Asp Asp Ile Lys Lys Gln Leu His Val Leu Ile
                85                  90                  95

Asp Gly Leu Asn Arg Leu Gln Gly Met Glu Asp Asp Ala Gly Leu
            100                 105                 110

Val Thr Ala Gln Ile Leu Val Ser Gly Ala Leu Gly Ile Gly Leu Leu
        115                 120                 125

Ser Thr Ser Thr Val Ile Ala Lys Leu Ala Val Gly Ala Ala Glu Ala
    130                 135                 140

Val Ala Ala Phe Ala Gly Val Thr Val Ala Ser Val Gly Ala Val Val
145                 150                 155                 160

Ala Ile Ala Ala Leu Val Ile Val Ala Ile Ile Pro Ile Ile Tyr
                165                 170                 175

Phe Met Ala Lys Pro Ala Asn Ala Ile Val Leu Leu Ile Asn Glu Leu
            180                 185                 190
```

```
Asp Lys Pro Leu Thr Phe Val Ser Asp His Asn Val His Gly Lys Pro
        195                 200                 205

Met Leu Met Thr Thr Pro Ile Pro Glu Ala Val Val Ile Pro Glu Val
        210                 215                 220

Gly Thr Tyr Pro Val Ser Gly Leu Ile Ala Thr Glu Lys Arg Glu Asn
225                 230                 235                 240

Ala Leu Val Gly Thr Gln Tyr Gly Phe Thr Met Gln Tyr Gly Gly Thr
            245                 250                 255

Asp Thr Lys Leu Ser Phe Gly Val Glu Cys Pro Leu Thr Gly Ile Tyr
            260                 265                 270

Thr Asp Asn Asn Cys Tyr Cys Ala Ile Asp Glu Ser Ala Ser Thr Val
            275                 280                 285

Ala Glu Met Thr Thr Lys Gln Asn Lys Gln Phe Trp Glu Asp Glu Lys
        290                 295                 300

Asn Gly Ile Lys Leu Ser Ile Arg Cys Asn Ser Gly Ser Gly Ser Ile
305                 310                 315                 320

Ala Tyr Tyr Val Ala Arg Ala Tyr Arg Gly
            325                 330

<210> SEQ ID NO 9
<211> LENGTH: 993
<212> TYPE: DNA
<213> ORGANISM: Lysinibacillus sphaericus

<400> SEQUENCE: 9
atgcacacta caattgatat cgatcttaaa ttaaaacagg ggttccggtc tttattcccg        60
gattatgcaa caaaactaga gaaggctagt tcacaagagg agatcaataa g

```
1               5                   10                  15
Ser Leu Phe Pro Asp Tyr Ala Thr Lys Leu Glu Lys Ala Ser Ser Gln
                    20                  25                  30

Glu Glu Ile Asn Lys Leu Gln Thr Ile Phe Ile Glu Arg Lys Gln
                35                  40                  45

Ala Leu Ala Asp Ala Leu Gly Lys Asp Ile Thr Glu Leu Glu Ala Ser
            50                  55                  60

Asp Gln Thr Ala Ala Ile Pro Leu Lys Lys Glu Thr Tyr Glu Ile Leu
65                  70                  75                  80

Val Asn Ala Thr Gly Asp Asp Ile Lys Arg Gln Leu His Val Ile Ile
                    85                  90                  95

Asp Gly Leu Glu Arg Leu Lys Gly Leu Glu Lys Asp Asp Ala Gly Ile
                100                 105                 110

Val Thr Ala Gln Ile Leu Leu Ser Gly Val Leu Gly Ile Gly Phe Leu
                115                 120                 125

Ser Thr Ser Thr Val Val Ala Lys Leu Ala Val Gly Ala Ala Glu Ala
                130                 135                 140

Ile Ala Ala Leu Ala Gly Val Thr Ala Thr Val Gly Val Val Val
145                 150                 155                 160

Ala Val Ala Ala Leu Val Ile Val Ala Ile Ile Pro Ile Ile Tyr
                165                 170                 175

Phe Met Lys Lys Pro Ala Asn Ala Ile Val Leu Leu Ile Asn Glu Leu
                180                 185                 190

Asp Lys Pro Leu Thr Phe Val Ser Asp His Asn Val His Gly Lys Pro
                195                 200                 205

Met Leu Met Thr Thr Pro Ile Pro Glu Gly Val Glu Ile Pro Gly Val
            210                 215                 220

Ala Lys Tyr Pro Val Ala Gly Leu Ile Ala Thr Glu Lys Arg Asp Ser
225                 230                 235                 240

Ala Leu Val Gly Thr Gln Tyr Gly Phe Thr Met Gln Tyr Gly Ser Thr
                245                 250                 255

Gly Thr Asn Phe Ser Phe Gly Val Glu Cys Pro Leu Thr Ser Leu Ser
                260                 265                 270

Thr Asp Asn Asn Cys Tyr Cys Ala Ile Asp Glu Ser Ala Lys Thr Val
                275                 280                 285

Ala Glu Arg Thr Ser Asn Lys Asn Lys Gln Phe Trp Glu Ala Glu Lys
                290                 295                 300

Asp Gly Leu Lys Leu Ser Ile Arg Cys Asn Ser Gly Ser Gly Ser Ile
305                 310                 315                 320

Ala Tyr Tyr Val Ala Arg Ala Tyr Arg Ala
                325                 330

<210> SEQ ID NO 11
<211> LENGTH: 993
<212> TYPE: DNA
<213> ORGANISM: Lysinibacillus sp.

<400> SEQUENCE: 11
atgcacacta caattgatat cgatcttaag ttaaaacagg ggttccggtc attattcccg        60
gattatgcaa caaagctaga gaaggcgact tctcaagagg aaataaatag acttcaggca       120
atttttattg aggaaagaaa gcaagcgcta gcagacgctt taggtaaaga catcagcgag       180
ctggaggcaa gtgaccaaac tgcaccgatt cctttgaaaa aggaaacata tgaaattctt       240
atcaatgcaa ctggtgacga catcaaaaga caaattcatg tcattattga cggtcttgaa       300
```

```
cgattaaaag ggatggaaaa tgacgaggca ggtcttgtca ctgcacaaat tctactttcc    360
ggtgtattag gaatcggctt tttgtcaacg tcgacagttg tggcaaaatt ggcagtgggc    420
gcaggagaag caatcgccgc cttagctggt gtctcagttg caacggttgg agtggtggta    480
gcagttgcag cgctcgttat tgttgcaatc attatcccta tcatttattt tatgaaaaaa    540
ccagcaaatg ctattgtgtt gttaataaat gaattggaca agcctcttac atttgtcagt    600
gaccataacg ttcatggcaa accaatgcta atgactacac ctattcccga aggtatcgag    660
attcctgagg ttgctaaata tccagtagcc ggattaatcg caaccgagaa gcgagatagt    720
gctttagtag ggacacaata tggttttaca atgaaatatg gaatacagaa tacgaatttt    780
tcattcggtg tagaatgtcc gttaacatcc ctttctaccg ataataattg ttattgtgcc    840
atagacgaaa atgctaaaac agtcgctgaa agaacttccg ataaaaataa gcaattctgg    900
gaggctgaaa aagacggcct caaattgagc attcgttgca attctggtag tggctcgatc    960
gcttattacg ttgcacgagc atttaaagcc taa                                 993
```

<210> SEQ ID NO 12
<211> LENGTH: 330
<212> TYPE: PRT
<213> ORGANISM: Lysinibacillus sp.

<400> SEQUENCE: 12

```
Met His Thr Thr Ile Asp Ile Asp Leu Lys Leu Lys Gln Gly Phe Arg
1               5                   10                  15

Ser Leu Phe Pro Asp Tyr Ala Thr Lys Leu Glu Lys Ala Thr Ser Gln
            20                  25                  30

Glu Glu Ile Asn Arg Leu Gln Ala Ile Phe Ile Glu Glu Arg Lys Gln
        35                  40                  45

Ala Leu Ala Asp Ala Leu Gly Lys Asp Ile Ser Glu Leu Glu Ala Ser
    50                  55                  60

Asp Gln Thr Ala Pro Ile Pro Leu Lys Lys Glu Thr Tyr Glu Ile Leu
65                  70                  75                  80

Ile Asn Ala Thr Gly Asp Asp Ile Lys Arg Gln Ile His Val Ile Ile
                85                  90                  95

Asp Gly Leu Glu Arg Leu Lys Gly Met Glu Asn Asp Glu Ala Gly Leu
            100                 105                 110

Val Thr Ala Gln Ile Leu Leu Ser Gly Val Leu Gly Ile Gly Phe Leu
        115                 120                 125

Ser Thr Ser Thr Val Val Ala Lys Leu Ala Val Gly Ala Gly Glu Ala
    130                 135                 140

Ile Ala Ala Leu Ala Gly Val Ser Val Ala Thr Val Gly Val Val Val
145                 150                 155                 160

Ala Val Ala Ala Leu Val Ile Val Ala Ile Ile Pro Ile Ile Tyr
                165                 170                 175

Phe Met Lys Lys Pro Ala Asn Ala Ile Val Leu Leu Ile Asn Glu Leu
            180                 185                 190

Asp Lys Pro Leu Thr Phe Val Ser Asp His Asn Val His Gly Lys Pro
        195                 200                 205

Met Leu Met Thr Thr Pro Ile Pro Glu Gly Ile Glu Ile Pro Glu Val
    210                 215                 220

Ala Lys Tyr Pro Val Ala Gly Leu Ile Ala Thr Glu Lys Arg Asp Ser
225                 230                 235                 240

Ala Leu Val Gly Thr Gln Tyr Gly Phe Thr Met Lys Tyr Gly Asn Thr
```

```
                245                 250                 255
Asp Thr Asn Phe Ser Phe Gly Val Glu Cys Pro Leu Thr Ser Leu Ser
            260                 265                 270

Thr Asp Asn Asn Cys Tyr Cys Ala Ile Asp Glu Asn Ala Lys Thr Val
            275                 280                 285

Ala Glu Arg Thr Ser Asp Lys Asn Lys Gln Phe Trp Glu Ala Glu Lys
            290                 295                 300

Asp Gly Leu Lys Leu Ser Ile Arg Cys Asn Ser Gly Ser Gly Ser Ile
305                 310                 315                 320

Ala Tyr Tyr Val Ala Arg Ala Phe Lys Ala
                325                 330

<210> SEQ ID NO 13
<211> LENGTH: 993
<212> TYPE: DNA
<213> ORGANISM: Lysinibacillus sp.

<400> SEQUENCE: 13
atgcacacta caattgatat cgatcttaag ttaaaacagg ggttccggtc attattcccg      60
gattatgcaa caaagctaga gagggcgact tctcaagagg aaatcaataa acttcaggca     120
attttcattg aggaaagaaa gcaagcgctg ccgacgcctt aggtaaaga catcagcgag      180 ctagaggcga gtgaccaaac cgcaccaatt cctttgaaaa aggaaacgta tgaaattctt     240
atcaatgcaa cgggtgacga catcaaaaga caaattcatg tcattattga tggtcttgaa     300
cgattaaagg ggatggaaaa tgacgaggca ggtcttgtca ctgcacaaat tcttcttttcc    360 ggtgtattag gagtcggctt tttatcaacg tcgaccgtag tggcaaaatt ggcagtgggc     420
gcagcagagg caatcgccgc cttagctggt gtctcagttg caacagttgg agtagtggtg     480
gcagttgcgg cgcttgttat cgtagctatc attattccta tcatttattt tatgaaaaaa     540
ccagcaaatg ccatagtgtt gttaattaat gaattggaca aacctcttac atttgttagt     600
gaccataatg ttcatggcaa accaatgctg atgactacgc ctattcctga aggtgtcgag     660
attcctgggg ttgctaaata tccagtagcc ggattaattg caaccgagaa gcgagatagt     720
gctttagtcg ggacacaata tggcttcaca atgaaatatg caatacagg tactaattttt     780 tcattcggcg tagaatgtcc gttaacatcc atttctactg ataataattg ttattgtgcc     840
atagacgaaa gtgctaaaac agttgcggaa agaacttccg ataaaaataa gcaattctgg     900
gaagcagaaa aagacggcct caaattgagc attcgttgca attctggtag tggctcaatc     960
gcttactacg tagcacgagc atttaaagca taa                                  993

<210> SEQ ID NO 14
<211> LENGTH: 330
<212> TYPE: PRT
<213> ORGANISM: Lysinibacillus sp.

<400> SEQUENCE: 14

Met Gln Thr Thr Ile Asp Ile Asp Leu Lys Leu Lys Gln Gly Phe Arg
1               5                   10                  15

Ser Leu Phe Pro Asp Tyr Ala Thr Lys Leu Glu Arg Ala Thr Ser Gln
            20                  25                  30

Glu Glu Ile Asn Lys Leu Gln Ala Ile Phe Ile Glu Glu Arg Lys Gln
            35                  40                  45

Ala Leu Ala Asp Ala Leu Gly Lys Asp Ile Ser Glu Leu Glu Ala Ser
            50                  55                  60
```

Asp Gln Thr Ala Pro Ile Pro Leu Lys Lys Glu Thr Tyr Glu Ile Leu
65                  70                  75                  80

Ile Asn Ala Thr Gly Asp Asp Ile Lys Arg Gln Ile His Val Ile Ile
                85                  90                  95

Asp Gly Leu Glu Arg Leu Lys Gly Met Glu Asn Asp Glu Ala Gly Leu
            100                 105                 110

Val Thr Ala Gln Ile Leu Leu Ser Gly Val Leu Gly Val Gly Phe Leu
        115                 120                 125

Ser Thr Ser Thr Val Val Ala Lys Leu Ala Val Gly Ala Ala Glu Ala
    130                 135                 140

Ile Ala Ala Leu Ala Gly Val Ser Val Ala Thr Val Gly Val Val Val
145                 150                 155                 160

Ala Val Ala Ala Leu Val Ile Val Ala Ile Ile Pro Ile Ile Tyr
                165                 170                 175

Phe Met Lys Lys Pro Ala Asn Ala Ile Val Leu Leu Ile Asn Glu Leu
            180                 185                 190

Asp Lys Pro Leu Thr Phe Val Ser Asp His Asn Val His Gly Lys Pro
        195                 200                 205

Met Leu Met Thr Thr Pro Ile Pro Glu Gly Val Glu Ile Pro Gly Val
    210                 215                 220

Ala Lys Tyr Pro Val Ala Gly Leu Ile Ala Thr Glu Lys Arg Asp Ser
225                 230                 235                 240

Ala Leu Val Gly Thr Gln Tyr Gly Phe Thr Met Lys Tyr Gly Asn Thr
                245                 250                 255

Gly Thr Asn Phe Ser Phe Gly Val Glu Cys Pro Leu Thr Ser Ile Ser
            260                 265                 270

Thr Asp Asn Asn Cys Tyr Cys Ala Ile Asp Glu Ser Ala Lys Thr Val
        275                 280                 285

Ala Glu Arg Thr Ser Asp Lys Asn Lys Gln Phe Trp Glu Ala Glu Lys
    290                 295                 300

Asp Gly Leu Lys Leu Ser Ile Arg Cys Asn Ser Gly Ser Gly Ser Ile
305                 310                 315                 320

Ala Tyr Tyr Val Ala Arg Ala Phe Lys Ala
                325                 330

<210> SEQ ID NO 15
<211> LENGTH: 993
<212> TYPE: DNA
<213> ORGANISM: Lysinibacillus sp.

<400> SEQUENCE: 15
atgcacacta caattgatat cgatcttaaa ttaaaacagg ggttccgttc tttgtttcca      60
gattatgcga caaaactaga gaaggctaca tcacaggagg aaattaatca actccaagca     120
acattcattg aagaaagaaa gctggagtta gctaaggttt agggaagga tatcttggag      180 ctaaatgcaa gcgattatac agcaccgttt cctttaaaaa agagacgta tgagattctt      240 gttaatgcta ctggagatac gattaaaaag cagcttcatg tcattattga tggtcttgag     300
cgattaaaag gaatggaaaa tgatgaggcg ggccttgtaa ctgcacaaat gctgcttcct     360
ggtgtattag ggattgggtt attatcaaca tcaacagttg tagcaaaatt ggctgtaggt    420
gcggtagaag ctgttgctgc attagccggt gtcacggctg caacagtagg aatagttgtt     480
gcggtagtag cccttgttat tgtatctatc ctaattccaa ttatctactt catggaaaaa     540
cctgcaaatg caattgtatt gttaataaat gaattagaca agccactcgt atttgaacaa     600

```
gaccataatg tgcgtggtgt accagcactt atgacagaaa cgataccaga aggcattgaa      660
attcctggga tagcgaaata tcctgttggt ggattaatag catcccaaaa agcagacaaa      720
tccttgtatg gaacacaata cggttttacg atgcgatatg cagtacaga tactaaatta      780 tcttttggtg tagaatgtcc tttaacatct ctttatcatg ataataattg ttattgtgct      840
ataggtgaaa gtgccaaaaa agccgcagaa actactacaa agaaaaataa gcaattctgg      900
gaaactgaaa aagatggcat caaattaagt atccgttgta actcaggtag tggctccatt      960
gcctattatg tagcacgcgc atataaagca tag                                   993
```

<210> SEQ ID NO 16
<211> LENGTH: 330
<212> TYPE: PRT
<213> ORGANISM: Lysinibacillus sp.

<400> SEQUENCE: 16

```
Met His Thr Thr Ile Asp Ile Asp Leu Lys Leu Lys Gln Gly Phe Arg
1               5                   10                  15

Ser Leu Phe Pro Asp Tyr Ala Thr Lys Leu Glu Lys Ala Thr Ser Gln
            20                  25                  30

Glu Glu Ile Asn Gln Leu Gln Ala Thr Phe Ile Glu Glu Arg Lys Leu
        35                  40                  45

Glu Leu Ala Lys Val Leu Gly Lys Asp Ile Leu Glu Leu Asn Ala Ser
    50                  55                  60

Asp Tyr Thr Ala Pro Phe Pro Leu Lys Lys Glu Thr Tyr Glu Ile Leu
65                  70                  75                  80

Val Asn Ala Thr Gly Asp Thr Ile Lys Lys Gln Leu His Val Ile Ile
                85                  90                  95

Asp Gly Leu Glu Arg Leu Lys Gly Met Glu Asn Asp Glu Ala Gly Leu
            100                 105                 110

Val Thr Ala Gln Met Leu Leu Ser Gly Val Leu Gly Ile Gly Leu Leu
        115                 120                 125

Ser Thr Ser Thr Val Val Ala Lys Leu Ala Val Gly Ala Val Glu Ala
    130                 135                 140

Val Ala Ala Leu Ala Gly Val Thr Ala Ala Thr Val Gly Ile Val Val
145                 150                 155                 160

Ala Val Val Ala Leu Val Ile Val Ser Ile Leu Ile Pro Ile Ile Tyr
                165                 170                 175

Phe Met Glu Lys Pro Ala Asn Ala Ile Val Leu Leu Ile Asn Glu Leu
            180                 185                 190

Asp Lys Pro Leu Val Phe Glu Gln Asp His Asn Val Arg Gly Val Pro
        195                 200                 205

Ala Leu Met Thr Glu Thr Ile Pro Glu Gly Ile Glu Ile Pro Gly Ile
    210                 215                 220

Ala Lys Tyr Pro Val Gly Gly Leu Ile Ala Ser Gln Lys Ala Asp Lys
225                 230                 235                 240

Ser Leu Tyr Gly Thr Gln Tyr Gly Phe Thr Met Arg Tyr Gly Ser Thr
                245                 250                 255

Asp Thr Lys Leu Ser Phe Gly Val Glu Cys Pro Leu Thr Ser Leu Tyr
            260                 265                 270

His Asp Asn Asn Cys Tyr Cys Ala Ile Gly Glu Ser Ala Lys Lys Ala
        275                 280                 285

Ala Glu Thr Thr Thr Lys Lys Asn Lys Gln Phe Trp Glu Thr Glu Lys
    290                 295                 300
```

```
Asp Gly Ile Lys Leu Ser Ile Arg Cys Asn Ser Gly Ser Gly Ser Ile
305                 310                 315                 320

Ala Tyr Tyr Val Ala Arg Ala Tyr Lys Ala
                325                 330

<210> SEQ ID NO 17
<211> LENGTH: 993
<212> TYPE: DNA
<213> ORGANISM: Bacillus sp.

<400> SEQUENCE: 17
atgcaaattg cacatgatat tgatttaagg ttaaagcaag ggttccgttc tgtattcccg      60
cagtatgcaa tgaaacttga aaagctact tcccaagagg aaattaataa tctgcatgcc     120
acttttatta agaaagaaa gcttgcatta gcaaatgctt tgggaaaaga tattagtgta     180
ctagaagaaa aagattatac atgtgcaatt cctttaaaaa aagagacata ccaaaattta     240
attaattcga caggtgagga tattaaaaga cagcttcaaa ttttaattga tggtcttcaa     300
aggttaaaag atatggagaa tgatgatgcg ggtcttatta cagcacaaat tttactttct     360
ggtgcattag gagttggtat gttatcaacc tcgacagtta tagcacgttt agtatctggg     420
gcaattgaag cagtagctgc ttttgcaggt gttgaagctg ctactgtttc agttgttgtt     480
ggcatagttt ctcttattat tgttgcaatt ctcattccta ttatttattt tatggcgaag     540
cctgcaaatg cgattatatt attgattaat gaactggaca aggaacttgt atttctgga     600 gattataata ttcatggaaa acctatgctc atgacaacac ctattcctaa tggagttgaa     660
attcctggag ttggtaagta tcctgttgca ggatttattg cgagtgaaaa agaaactgcg     720
gctttagttg gtacacaata tggttttacg atgcaatacg gtgatacaag tactaagttc     780
tcttttgggg tagaatgtcc attaagttct ttatatactg ataataattg ttattgtgct     840
attgatgaaa gtgctgaagc agttgcgaat atgactacaa ataagaatgt gcaattctgg     900
gaagccgaaa aagacggttt gaaactaagt attcgttgca attcaggaag tgggtcaatt     960
gcttactacg ttgctcgtgc atatcgatca taa                                  993

<210> SEQ ID NO 18
<211> LENGTH: 330
<212> TYPE: PRT
<213> ORGANISM: Bacillus sp.

<400> SEQUENCE: 18

Met Gln Ile Ser His Asp Ile Asp Leu Arg Leu Lys Gln Gly Phe Arg
1               5                   10                  15

Ser Val Phe Pro Gln Tyr Ala Met Lys Leu Glu Lys Ala Thr Ser Gln
            20                  25                  30

Glu Glu Ile Asn Asn Leu His Ala Thr Phe Ile Lys Glu Arg Lys Leu
        35                  40                  45

Ala Leu Ala Asn Ala Leu Gly Lys Asp Ile Ser Val Leu Glu Glu Lys
    50                  55                  60

Asp Tyr Thr Cys Ala Ile Pro Leu Lys Lys Glu Thr Tyr Gln Asn Leu
65                  70                  75                  80

Ile Asn Trp Thr Gly Glu Asp Ile Lys Arg Gln Leu Gln Ile Leu Ile
                85                  90                  95

Asp Gly Leu Gln Arg Leu Lys Asp Met Glu Asn Asp Asp Ala Gly Leu
            100                 105                 110

Ile Thr Ala Gln Ile Leu Leu Ser Gly Ala Leu Gly Val Gly Met Leu
        115                 120                 125
```

```
Ser Thr Ser Thr Val Ile Ala Arg Leu Val Ser Gly Ala Ile Glu Ala
    130                 135                 140

Val Ala Ala Phe Ala Gly Val Glu Ala Ala Thr Val Ser Val Val Val
145                 150                 155                 160

Gly Ile Val Ser Leu Ile Ile Val Ala Ile Leu Ile Pro Ile Ile Tyr
                165                 170                 175

Phe Met Ala Lys Pro Ala Asn Ala Ile Ile Leu Leu Ile Asn Glu Leu
                180                 185                 190

Asp Lys Glu Leu Val Phe Ser Gly Asp Tyr Asn Ile His Gly Lys Pro
            195                 200                 205

Met Leu Met Thr Thr Pro Ile Pro Asn Gly Val Glu Ile Pro Gly Val
    210                 215                 220

Gly Lys Tyr Pro Val Ala Gly Phe Ile Ala Ser Glu Lys Glu Thr Ala
225                 230                 235                 240

Ala Leu Val Gly Thr Gln Tyr Gly Phe Thr Met Gln Tyr Gly Asp Thr
                245                 250                 255

Ser Thr Lys Phe Ser Phe Gly Val Glu Cys Pro Leu Ser Ser Leu Tyr
                260                 265                 270

Thr Asp Asn Asn Cys Tyr Cys Ala Ile Asp Glu Ser Ala Glu Ala Val
            275                 280                 285

Ala Asn Met Thr Thr Asn Lys Asn Val Gln Phe Trp Glu Ala Glu Lys
    290                 295                 300

Asp Gly Leu Lys Leu Ser Ile Arg Cys Asn Ser Gly Ser Gly Ser Ile
305                 310                 315                 320

Ala Tyr Tyr Val Ala Arg Ala Tyr Arg Ser
                325                 330

<210> SEQ ID NO 19
<211> LENGTH: 993
<212> TYPE: DNA
<213> ORGANISM: Lysinibacillus sp.

<400> SEQUENCE: 19
atgcacacta caattgatat cgatcttaag ttaaaacaag ggttccggtc tttattcccg      60
gattatgcaa caaagctcga gaaagctact tctcaagagg agatcaataa gcttcaggct     120 attttattg aggaaagaaa gcaagcgctg gcagacgcgc taggcaagga tatctctgag     180
ttacaggcaa gtgaccaaac tgcagcaatt cctttgaaaa aggagacgta tgatattctc     240
atcaatgcga ctggtgatga tatcaaaaga caactgcatg tcattattga tggtcttgaa     300
cgattaaaag ggatggaaaa agacgatgca ggacttgtga ctgcacaaat cctactttca     360
ggcgtattag gaatcggctc cttagcaatt tcggaagttg tgataaaatt ggcagctggt     420
gctgccgaag cagtcgcagc cctagctggt gttactactg cgacagttgg tgtagttgtc     480
gcgatcgcgg ctcttgttat cgtagcgatc attattccga tcatttattt tatgacaaaa     540
ccagcaaatg ctattgtctt attaattaat gaattggaca agccccttgt atttgtagac     600
gatcataata ttcacggcaa accaatgcta atgacaacgc ctattcctga aggtgtcgaa     660
attcctgggg ctgctaaata ccctatagcc ggattaattg cggctgagaa gcagataag     720 gctttaatag ggactcaata tggctttaca atgcaatatg gtagcacaag cactaaattc     780
tcattcggtg tagaatgtcc gttaacatct ctttctaccg ataataattg ttattgtgcc     840
atagatgaaa gtgctaaaac agttgcggaa aggacttcca ataacaataa gcaattctgg     900
gaggttgaaa aagacggcct taaattgagt attcgctgca attcaggaag tggttcaatc     960
```
gcttattacg tagcacgagc atataaagct taa                                      993

<210> SEQ ID NO 20
<211> LENGTH: 330
<212> TYPE: PRT
<213> ORGANISM: Lysinibacillus sp.

<400> SEQUENCE: 20

Met His Thr Thr Ile Asp Ile Asp Leu Lys Leu Lys Gln Gly Phe Arg
1               5                   10                  15

Ser Leu Phe Pro Asp Tyr Ala Thr Lys Leu Glu Lys Ala Thr Ser Gln
            20                  25                  30

Glu Glu Ile Asn Lys Leu Gln Ala Ile Phe Ile Glu Glu Arg Lys Gln
        35                  40                  45

Ala Leu Ala Asp Ala Leu Gly Lys Asp Ile Ser Glu Leu Gln Ala Ser
    50                  55                  60

Asp Gln Thr Ala Ala Ile Pro Leu Lys Lys Glu Thr Tyr Asp Ile Leu
65                  70                  75                  80

Ile Asn Ala Thr Gly Asp Asp Ile Lys Arg Gln Leu His Val Ile Ile
                85                  90                  95

Asp Gly Leu Glu Arg Leu Lys Gly Met Glu Lys Asp Asp Ala Gly Leu
            100                 105                 110

Val Thr Ala Gln Ile Leu Leu Ser Gly Val Leu Gly Ile Gly Ser Leu
        115                 120                 125

Ala Ile Ser Glu Val Val Ile Lys Leu Ala Ala Gly Ala Ala Glu Ala
    130                 135                 140

Val Ala Ala Leu Ala Gly Val Thr Thr Ala Thr Val Gly Val Val Val
145                 150                 155                 160

Ala Ile Ala Ala Leu Val Ile Val Ala Ile Ile Pro Ile Ile Tyr
                165                 170                 175

Phe Met Thr Lys Pro Ala Asn Ala Ile Val Leu Leu Ile Asn Glu Leu
            180                 185                 190

Asp Lys Pro Leu Val Phe Val Asp Asp His Asn Ile His Gly Lys Pro
        195                 200                 205

Met Leu Met Thr Thr Pro Ile Pro Glu Gly Val Glu Ile Pro Gly Ala
    210                 215                 220

Ala Lys Tyr Pro Ile Ala Gly Leu Ile Ala Ala Glu Lys Arg Asp Lys
225                 230                 235                 240

Ala Leu Ile Gly Thr Gln Tyr Gly Phe Thr Met Gln Tyr Gly Ser Thr
                245                 250                 255

Ser Thr Lys Phe Ser Phe Gly Val Glu Cys Pro Leu Thr Ser Leu Ser
            260                 265                 270

Thr Asp Asn Asn Cys Tyr Cys Ala Ile Asp Glu Ser Ala Lys Thr Val
        275                 280                 285

Ala Glu Arg Thr Ser Asn Asn Lys Gln Phe Trp Glu Val Glu Lys
    290                 295                 300

Asp Gly Leu Lys Leu Ser Ile Arg Cys Asn Ser Gly Ser Gly Ser Ile
305                 310                 315                 320

Ala Tyr Tyr Val Ala Arg Ala Tyr Lys Ala
                325                 330

<210> SEQ ID NO 21
<211> LENGTH: 990
<212> TYPE: DNA
<213> ORGANISM: Lysinibacillus sphaericus

<400> SEQUENCE: 21

```
atgtacgatg cagataatat tgatgtcaag ctaaagcagg gatttcaatc attattccct      60
gaatatgcta ccttgttaaa tcaagctact tctcaagaac aaataattag tttgcataat     120
tcttttattg aagaaagaaa aaaagcatta gcaacagcta taaaggcaac caatatatca     180
gacagtagga atcctaagtc ccccattgcg ttaacacaag aagaatatga aacctaatt      240
aatgcaacag gtgatgatat taaatatcga attcaagctt tgcttgatgg tcttcaacga     300
ttaaagggca tggagaatga tcaaatagaa catgtagccg cacaaatgat tgtcactggt     360
atattaggca ttggcgtaga atccactaca gcagcactag cgattgcagg cggaggagaa     420
atcattgaag cttacattgc tcttgcagcc cttacatcta ctaccgtagc agtagttatt     480
gctgtcgttt gtcttgtgat tattgccatt attattccac ttatttattt tatggagaag     540
cccgcaaatg cacttatact attaattaat gaattggaca aaccacttgt atttgctaac     600
gattttaatg tgcatggaaa acccacatat ctcacagaaa caattaacaa tgcggttata     660
ttcccagatc gtaagtttgt aacagcagga tttattggca gtcaaaaact agacagcgct     720
ttatatggca cacaatatgg ctttacaatg aagtatggac atacagacac tcaatttact     780
tttggagtag aatgtccttt aagctccttg tatactgaca ataactgttt ttgtgccttt     840
gataaaaatg cacaagaagc tgctgaatta acggctaaaa ataataaaca gttttgggaa     900
accgaaaaag atggtattaa attaagcatt cgttgtaact caaaaagtgg ctcattggcc     960
tactacgtcg ctcgtgccta tcacgtttaa                                      990
```

<210> SEQ ID NO 22
<211> LENGTH: 329
<212> TYPE: PRT
<213> ORGANISM: Lysinibacillus sphaericus

<400> SEQUENCE: 22

```
Met Tyr Asp Ala Asp Asn Ile Asp Val Lys Leu Lys Gln Gly Phe Gln
1               5                   10                  15

Ser Leu Phe Pro Glu Tyr Ala Thr Leu Leu Asn Gln Ala Thr

```
                180             185             190
Asp Lys Pro Leu Val Phe Ala Asn Asp Phe Asn Val His Gly Lys Pro
            195                 200                 205

Thr Tyr Leu Thr Glu Thr Ile Asn Asn Ala Val Ile Phe Pro Asp Arg
        210                 215                 220

Lys Phe Val Thr Ala Gly Phe Ile Gly Ser Gln Lys Leu Asp Ser Ala
225                 230                 235                 240

Leu Tyr Gly Thr Gln Tyr Gly Phe Thr Met Lys Tyr Gly His Thr Asp
            245                 250                 255

Thr Gln Phe Thr Phe Gly Val Glu Cys Pro Leu Ser Ser Leu Tyr Thr
        260                 265                 270

Asp Asn Asn Cys Phe Cys Ala Phe Asp Lys Asn Ala Gln Glu Ala Ala
            275                 280                 285

Glu Leu Thr Ala Lys Asn Lys Gln Phe Trp Glu Thr Glu Lys Asp
        290                 295                 300

Gly Ile Lys Leu Ser Ile Arg Cys Asn Ser Lys Ser Gly Ser Leu Ala
305                 310                 315                 320

Tyr Tyr Val Ala Arg Ala Tyr His Val
            325

<210> SEQ ID NO 23
<211> LENGTH: 990
<212> TYPE: DNA
<213> ORGANISM: Lysinibacillus varians

<400> SEQUENCE: 23
atgtacgatg cagataatat tgatgtcaag ctaaagcagg gatttcaatc attattccct      60
gaatatgcta ccttgttaaa tcaagctatt tctcaagaac aaataattag tttgcataat     120
tcttttattg aagaaagaaa aaaagcatta gcaacagcta taaaggcaac taatatatca     180
gacagtagga tcctaagtc ccccattgcg ttaacacaag aagaatacga aaacctaatt     240
aatgcaacag gtgatgatat taaataccga attcaagctt tgcttgatgg tcttcaacga     300
ttaaagggca tggagaatga tcaaatagaa catgtagccg cacaaatgat tgtcactggt     360
atattaggca ttggcgtaga atccactaca gcagcactag cgattgcagg cggaggggaa     420
atcattgaag cttacattgc tcttgcagcc cttacatcta ctaccgtagc agtagttatt     480
gctgtcgttt gtcttgtgat tattgccatt attattccac ttatttattt tatggagaag     540
cccgcaaatg cacttatact attaattaat gaattggaca aaccacttgt atttgctaac     600
gattttaatg tgcatggaaa acccacatat ctcacagaaa caattaacaa tgcggttata     660
ttcccagatc gtaagtttgt aacagcagga tttattggca gtcaaaaact agacagcgct     720
ttatatggca cacaatatgg ctttacaatg aagtatggac atacagacac tcaatttact     780
tttggagtag aatgtccttt aagctccttg tatactgaca taactgtttt tgtgcctttt     840
gataaaaatg cacaagaagc tgctgaatta acggctcaaa ataataaaca gttttgggaa     900
accgaaaaag atggtattaa attaagcatt cgttgtaatt caaaaagtgg ctcattggcc     960
tactacgtcg ctcgtgccta tcacgtttaa                                      990

<210> SEQ ID NO 24
<211> LENGTH: 329
<212> TYPE: PRT
<213> ORGANISM: Lysinibacillus varians

<400> SEQUENCE: 24
```

Met Tyr Asp Ala Asp Asn Ile Asp Val Lys Leu Lys Gln Gly Phe Gln
1               5                   10                  15

Ser Leu Phe Pro Glu Tyr Ala Thr Leu Leu Asn Gln Ala Ile Ser Gln
            20                  25                  30

Glu Gln Ile Ile Ser Leu His Asn Ser Phe Ile Glu Arg Lys Lys
        35                  40                  45

Ala Leu Ala Thr Ala Ile Lys Ala Thr Asn Ile Ser Asp Ser Arg Asn
50                  55                  60

Pro Lys Ser Pro Ile Ala Leu Thr Gln Glu Tyr Glu Asn Leu Ile
65                  70                  75                  80

Asn Ala Thr Gly Asp Asp Ile Lys Tyr Arg Ile Gln Ala Leu Leu Asp
                85                  90                  95

Gly Leu Gln Arg Leu Lys Gly Met Glu Asn Asp Gln Ile Glu His Val
            100                 105                 110

Ala Ala Gln Met Ile Val Thr Gly Ile Leu Gly Ile Gly Val Glu Ser
            115                 120                 125

Thr Thr Ala Ala Leu Ala Ile Ala Gly Gly Glu Ile Ile Glu Ala
            130                 135                 140

Tyr Ile Ala Leu Ala Ala Leu Thr Ser Thr Thr Val Ala Val Val Ile
145                 150                 155                 160

Ala Val Val Cys Leu Val Ile Ala Ile Ile Ile Pro Leu Ile Tyr
                165                 170                 175

Phe Met Glu Lys Pro Ala Asn Ala Leu Ile Leu Ile Asn Glu Leu
            180                 185                 190

Asp Lys Pro Leu Val Phe Ala Asn Asp Phe Asn Val His Gly Lys Pro
            195                 200                 205

Thr Tyr Leu Thr Glu Thr Ile Asn Asn Ala Val Ile Phe Pro Asp Arg
        210                 215                 220

Lys Phe Val Thr Ala Gly Phe Ile Gly Ser Gln Lys Leu Asp Ser Ala
225                 230                 235                 240

Leu Tyr Gly Thr Gln Tyr Gly Phe Thr Met Lys Tyr Gly His Thr Asp
                245                 250                 255

Thr Gln Phe Thr Phe Gly Val Glu Cys Pro Leu Ser Ser Leu Tyr Thr
            260                 265                 270

Asp Asn Asn Cys Phe Cys Ala Phe Asp Lys Asn Ala Gln Glu Ala Ala
        275                 280                 285

Glu Leu Thr Ala Gln Asn Asn Lys Gln Phe Trp Glu Thr Glu Lys Asp
            290                 295                 300

Gly Ile Lys Leu Ser Ile Arg Cys Asn Ser Lys Ser Gly Ser Leu Ala
305                 310                 315                 320

Tyr Tyr Val Ala Arg Ala Tyr His Val
                325

<210> SEQ ID NO 25
<211> LENGTH: 342
<212> TYPE: PRT
<213> ORGANISM: Bacillus sp.

<400> SEQUENCE: 25

Met His Thr Ser Lys Asp Ile Asp Leu Lys Leu Lys Gln Gly Phe Arg
1               5                   10                  15

Thr Leu Phe Pro Asn Tyr Ala Gln Lys Leu Glu Lys Ala Thr Ser Gln
            20                  25                  30

Ala Asp Ile Asn Gln Leu His Ala Leu Phe Ile Lys Glu Gln Gln Gln
        35                  40                  45

```
Lys Leu Ala Asp Val Leu Gly Lys Glu Leu Lys Asp Thr Gln Asn Gln
         50                  55                  60

Cys Ser Val Ala Leu Thr Ile Ser Gln Tyr Glu Ser Leu Ile Asn Ala
 65                  70                  75                  80

Arg Gly Asp Ile Lys Lys Gln Leu Gln Tyr Leu Ile Asp Gly Leu
                 85                  90                  95

Gln Lys Leu Lys Ala Leu Glu Lys Arg Gly Asp Ser Cys Val Val Met
             100                 105                 110

Ala Gln Met Leu Leu Ala Gly Val Leu Gly Ile Gly Pro Lys Ser Ile
         115                 120                 125

Asp Gly Ala Met Glu Tyr Ile Ala Lys Asn Ser Ser Pro Ser Lys Glu
         130                 135                 140

Asp Glu Leu Met Val Thr Pro Glu Leu Ile Asp Ala Tyr Ile Ala Leu
145                 150                 155                 160

Ala Gly Leu Ser Ser Ala Thr Val Ala Tyr Val Ile Ala Ile Val Ser
             165                 170                 175

Leu Ala Val Val Ile Ile Leu Ile Pro Ile Ile Tyr Tyr Phe Ile Glu
             180                 185                 190

Lys Asp Ala Lys Ala Leu Ile Phe Leu Ile Asn Glu Leu Asp Lys Pro
         195                 200                 205

Leu Ser Phe Tyr Gly Asp Tyr Asn Val His Gly Asn Gly Thr Leu Tyr
210                 215                 220

Thr Ser Thr Ile Gln Asn Gly Leu Cys Ile Pro Asn Ile Gly Arg Tyr
225                 230                 235                 240

Ala Val Gly Gly Phe Phe Ala Thr Glu Lys Ala Ser Gly Ala Leu Ile
                 245                 250                 255

Gly Thr Gln Tyr Gly Phe Thr Met Thr Leu Gly Gly Thr Thr Lys Leu
             260                 265                 270

Ser Phe Gly Val Glu Cys Pro Leu Thr Ser Leu Tyr Thr Asp Asn Asn
         275                 280                 285

Cys Tyr Cys Ala Ile Asn Glu Asp Ala Lys Asn Val Ala Glu Leu Thr
         290                 295                 300

Ser Glu Lys Asn Gln Gln Tyr Trp Glu Ser Lys Gln Asn Gly Ile Gly
305                 310                 315                 320

Ile Ser Ile Arg Cys His Ser Gly Ser Gly Ser Val Ala Tyr Tyr Ile
                 325                 330                 335

Ala Arg Ala Tyr Gln Val
             340

<210> SEQ ID NO 26
<211> LENGTH: 365
<212> TYPE: PRT
<213> ORGANISM: Bacillus amyloliquefaciens

<400> SEQUENCE: 26

Met Asp Ser Ser Phe Asn Met Asp Leu Lys Leu Lys Gln Ser Phe Gln
 1               5                  10                  15

Ser Leu Phe Pro Glu Tyr Ala Ser Lys Leu Glu Lys Ala Ser Ser Pro
             20                  25                  30

Glu Glu Leu Asn Gln Leu His Asn Asp Phe Val Lys Glu Gln Lys Lys
         35                  40                  45

Glu Phe Ala Arg Thr Ile Gly Lys Asp Val Ser Ala Ile Glu Val Gly
         50                  55                  60

Glu Val Glu Tyr Asn Val Ala Ile Ala Leu Thr Asn Asp Gln Tyr Leu
```

```
                65                  70                  75                  80
        Gln Leu Ile Asn Ala Lys Gly Glu Asp Ile Lys Ala Leu Leu Gln Thr
                        85                  90                  95

Leu Leu Asp Gly Ala Lys Arg Ile Lys Glu Arg Glu His Asp Glu Lys
                    100                 105                 110

Gly Val Ile Ala Ala Gln Met Leu Ala Gly Ile Gly Ile Gly
                115                 120                 125

Pro Glu Ser Ile Glu Gly Ala Met Asn Tyr Leu Asn Ser Leu Asn Lys
            130                 135                 140

Glu Lys Lys Ser Val Val Ala Thr Asp Pro Ala Leu Leu Ala Lys Glu
        145                 150                 155                 160

Leu Gly Val Asp Gln Ser Met Val Val Gly Phe Pro Pro Ala Glu Ile
                        165                 170                 175

Ile Ala Gly Tyr Ala Ala Ile Ala Ala Leu Gly Ser Pro Ala Ile Ile
                    180                 185                 190

Ala Tyr Val Val Leu Leu Val Ser Ile Val Ile Ser Ile Leu Ile
                195                 200                 205

Gly Leu Leu Ile Tyr Phe Ala Asn Lys Pro Ala Ala Ala Ile Val Leu
            210                 215                 220

Phe Ile Asn Glu Leu Asp Lys Pro Val Lys Phe Leu Ser Asp His Asn
        225                 230                 235                 240

Ile His Gly Glu Pro Arg Leu Arg Thr Leu Thr Ile Arg Asn Gly Val
                        245                 250                 255

Tyr Val Pro Thr Ile Gly Met Tyr Pro Ser Ala Gly Phe Phe Ala Thr
                    260                 265                 270

Gln Lys His Glu Asp Ala Leu Ile Gly Thr Gln Tyr Gly Phe Thr Leu
                275                 280                 285

Lys Tyr Gly Asp Thr Asp Thr Lys Phe Thr Phe Ala Val Glu Cys Pro
            290                 295                 300

Leu Ala Glu Lys Arg Asn Ser Cys Tyr Cys Ser Phe Asn Glu Asp Pro
        305                 310                 315                 320

Glu Ser Ala Ala Gln Met Thr Asp Lys Lys Ser Ser Gln His Trp Glu
                        325                 330                 335

Ala Glu Gln Asn Gly Ile Lys Leu Ser Ile Thr Cys Asn Ser Asn Glu
                    340                 345                 350

Gly Ser Ile Ala Tyr Tyr Val Ala Arg Ala Tyr Arg Glu
                355                 360                 365

<210> SEQ ID NO 27
        <211> LENGTH: 1008
        <212> TYPE: DNA
        <213> ORGANISM: Pseudomonas monteilii

<400> SEQUENCE: 27
atgtctgagt cattacaaaa cctcaagtct aagttcagcg aagtatttcc tgagcacgca      60
aagctcctcg aagggccag atcccatact gaggtactaa acttcagga tcgttttcag      120 ctcgagttca agaccaaact ggctagcgcg ctgaacatca aacttgactc cctggatgac      180
cggaaaaccc aaccggcctt tgccctcaag cccgcgacct acaatgccct cataaatgcc      240
accggagggg ccatcgaaca gcagttgcac gacttgctga caagcattca gtctctgtca      300
aaaatggaac atgatgaccc caaggacgcg gtggcgacca tgtttgccgg tgggatcaca      360
agccttggtc tgacggccat cgcggcatac caaagcaagc tggtgatggg agcagtcgaa      420
gcggcggcgg cgctggccgg tgtcgaggta gccacctgg ctgtggtatg tagcatcgcg       480
```

```
acgctggtgg tgttcaccct gattctgccg atcctctttt acatggaaaa accggcaaac    540
tgcatcatcc tcttgatcaa cgaggtaggc gacaatgatg actcacttga attccaggag    600
gactataacg tacacggcaa gcccgcattg atcacacgat cgatactagg cccttggat     660 ttcggctcgg gccaagtaag atacaacgct ggattcatcg cggcgaaaa gcagataat     720 gcgctggtcg ggtgccagta cggattcacc ctcaccttca ataacggagg tgctcataac    780
tctctaaaag gtcagcgctt caccttcgga gttgactgtc ctttgacagg tatcgatggc    840
tggaacaatt gctattgtag ctttgatgac aatgccaagc aggctgcgga gaacacagac    900
aaacacgatg caatcagtta cacggcggaa aaaacggga tcaaactttc tataaaatgc    960
aactcgcaga aaggatccat cgcttattac gtggctcgag tttacaaa               1008
```

<210> SEQ ID NO 28
<211> LENGTH: 336
<212> TYPE: PRT
<213> ORGANISM: Pseudomonas monteilii

<400> SEQUENCE: 28

```
Met Ser Glu Ser Leu Gln Asn Leu Lys Ser Lys Phe Ser Glu Val Phe
1               5                   10                  15

Pro Glu His Ala Lys Leu Leu Glu Gly Ala Arg Ser His Thr Glu Val
                20                  25                  30

Leu Lys Leu Gln Asp Arg Phe Gln Leu Glu Phe Lys Thr Lys Leu Ala
            35                  40                  45

Ser Ala Leu Asn Ile Lys Leu Asp Ser Leu Asp Asp Arg Lys Thr Gln
        50                  55                  60

Pro Ala Phe Ala Leu Lys Pro Ala Thr Tyr Asn Ala Leu Ile Asn Ala
65                  70                  75                  80

Thr Gly Gly Ala Ile Glu Gln Gln Leu His Asp Leu Leu Thr Ser Ile
                85                  90                  95

Gln Ser Leu Ser Lys Met Glu His Asp Asp Pro Lys Asp Ala Val Ala
                100                 105                 110

Thr Met Phe Ala Gly Gly Ile Thr Ser Leu Gly Leu Thr Ala Ile Ala
                115                 120                 125

Ala Tyr Gln Ser Lys Leu Val Met Gly Ala Val Glu Ala Ala Ala Ala
        130                 135                 140

Leu Ala Gly Val Glu Val Ala Thr Leu Ala Val Val Cys Ser Ile Ala
145                 150                 155                 160

Thr Leu Val Val Phe Thr Leu Ile Leu Pro Ile Leu Phe Tyr Met Glu
                165                 170                 175

Lys Pro Ala Asn Cys Ile Ile Leu Leu Ile Asn Glu Val Gly Asp Asn
                180                 185                 190

Asp Asp Ser Leu Glu Phe Gln Glu Asp Tyr Asn Val His Gly Lys Pro
        195                 200                 205

Ala Leu Ile Thr Arg Ser Ile Leu Gly Pro Leu Asp Phe Gly Ser Gly
        210                 215                 220

Gln Val Arg Tyr Asn Ala Gly Phe Ile Ala Ala Glu Lys Arg Asp Asn
225                 230                 235                 240

Ala Leu Val Gly Cys Gln Tyr Gly Phe Thr Leu Thr Phe Asn Asn Gly
                245                 250                 255

Gly Ala His Asn Ser Leu Lys Gly Gln Arg Phe Thr Phe Gly Val Asp
                260                 265                 270

Cys Pro Leu Thr Gly Ile Asp Gly Trp Asn Asn Cys Tyr Cys Ser Phe
```

```
            275                 280                 285
Asp Asp Asn Ala Lys Gln Ala Ala Glu Asn Thr Asp Lys His Asp Ala
    290                 295                 300
Ile Ser Tyr Thr Ala Glu Lys Asn Gly Ile Lys Leu Ser Ile Lys Cys
305                 310                 315                 320
Asn Ser Gln Lys Gly Ser Ile Ala Tyr Tyr Val Ala Arg Val Tyr Lys
                325                 330                 335
```

<210> SEQ ID NO 29
<211> LENGTH: 335
<212> TYPE: PRT
<213> ORGANISM: Candidatus stoquefichus

<400> SEQUENCE: 29

```
Met Asp Asn Val Met Ser Val Lys Glu Arg Phe Lys Lys Leu Tyr Pro
1               5                   10                  15
Gln Glu Ala Gln Ala Phe Glu Asn Ala Lys Ser Asp Glu Glu Leu Thr
                20                  25                  30
Ala Leu Lys Asn Gln Phe Leu Leu Glu Ala Lys Gln Arg Leu Ile Gln
            35                  40                  45
Glu Ile Glu Lys Thr Asp Leu Lys Asn Thr Val Asp Leu Glu Ala Leu
50                  55                  60
Lys Gly Thr Asp Glu Thr Val Ala Val Ala Ile Thr Glu Ser Val Tyr
65                  70                  75                  80
Lys Thr Leu Ile Asn Ala Arg Gly Asp Gln Ile Glu Thr Glu Leu Ile
                85                  90                  95
Lys Phe Phe Asp Thr Val Glu Arg Leu Lys Asp Met Gly Thr Gln Asp
                100                 105                 110
Ala Glu Val Leu Thr Tyr Ala Met Val Asn Gly Gly Ile Ala Ala Leu
            115                 120                 125
Gly Ile Ala Met Val Thr Asp Leu Ile Leu Asn Leu Leu Gln Gly Leu
130                 135                 140
Gly Leu Ala Glu Ala Ile Phe Thr Ala Val Val Ser Leu Gly Thr Thr
145                 150                 155                 160
Val Val Gly Ala Ile Val Asp Ile Ile Val Leu Cys Ile Ile Pro Ile
                165                 170                 175
Phe Tyr Phe Met Ala Lys Pro Ala Ala Cys Ile Phe Met Ile Ile Asn
                180                 185                 190
Glu Leu Glu Thr Asn Leu Val Ile Asp Glu Glu Lys Val Val His Gly
            195                 200                 205
Lys Val Asn Val Lys Thr Arg Glu Ile Ala Ala Ser Leu Lys Ile Ile
        210                 215                 220
His Thr Thr Arg Ser Gly Gly Ile Trp Ser Thr Gln Lys Lys Asp Ala
225                 230                 235                 240
Ala Leu Ile Gly Thr Gln Tyr Gly Val Val Leu Arg Gln Ala Lys Gly
                245                 250                 255
Ile Ser Gly Val Glu Pro Asp Asn Thr Lys Phe Ala Val Gly Val Glu
                260                 265                 270
Cys Pro Leu Ala Ser Gly Asn Asn Ser Cys Ala Val Gly Ile Asn Lys
            275                 280                 285
Thr Ala Ser Gln Ile Ala Asp Glu Val Asp Asp His Arg Arg Gln Ser
        290                 295                 300
Val Ser Val Ser Asp Gly Lys Tyr Gly Ile Glu Met His Cys Asn Ser
305                 310                 315                 320
```

```
Gly Ser Gly Ser Leu Ala Tyr Tyr Ile Cys Arg Ile Tyr Lys Cys
            325                 330                 335
```

<210> SEQ ID NO 30
<211> LENGTH: 339
<212> TYPE: PRT
<213> ORGANISM: Candidatus stoquefichus

<400> SEQUENCE: 30

```
Met Asp Asn Gln Leu Asn Asn Asp Leu Leu Gln Ile Lys Lys Phe
1               5                   10                  15

Glu Glu Met Phe Pro Asn Tyr Ala Ser Arg Leu Glu Ala Ala Thr Gln
                20                  25                  30

Gln Met Asn Asn Glu Thr Leu Glu Asp Thr Leu Lys Val Glu Ala Asp
            35                  40                  45

Ile Glu Ala Ile Gln Lys Glu Met Ile Asp Arg Ile Val Ser Asp Val
50                  55                  60

Lys Lys Val Ser Asn Asn Asp Ile Thr Glu Gly Phe Ala Ile Gln Leu
65                  70                  75                  80

Ser Leu Asp Lys Tyr Asn Asp Leu Ile Asn Ala Lys Gly Asp Ser Ile
                85                  90                  95

Glu Thr Gln Leu Leu Arg Leu Met Asp Ser Leu Glu Arg Leu Lys Asp
            100                 105                 110

Ile Asp Lys Ser Asp Ser Glu Ala Ile Thr Ala Thr Ile Leu Gly Gly
        115                 120                 125

Gly Leu Ser Ala Ile Thr Ala Ala Gly Ile Thr Tyr Phe Ala His Cys
    130                 135                 140

Ile Thr Ala Gln Glu Val Leu Leu Pro Ala Ala Phe Gly Ala Val Glu
145                 150                 155                 160

Phe Cys Thr Pro Ala Val Ile Val Gly Ala Val Ala Ile Ala Ile Val
                165                 170                 175

Leu Ile Ile Ile Pro Leu Ile Tyr Phe Ala Asn Lys Pro Ala Ala Cys
            180                 185                 190

Ile Leu Leu Val Ile Asn Glu Leu Arg Gln Asp Leu Ile Phe Lys Asp
        195                 200                 205

Asp Lys Cys Val His Gly Lys Ile Met Glu Thr Thr Lys His Ile Pro
    210                 215                 220

Lys Ile Thr Glu Thr Asn Thr Leu Gly Thr Phe Tyr Ser Ala Gly Phe
225                 230                 235                 240

Phe Ala Ser Gln Lys Lys Asp Ala Ala Leu Ile Gly Thr Gln Tyr Gly
                245                 250                 255

Leu Thr Leu Val Gln Ala Asp Ile Asp Lys Ile Thr Phe Asn Phe Gly
            260                 265                 270

Val Asn Cys Pro Leu Ala Asp Gly Lys Asn Asn Cys Ala Val Gly Cys
        275                 280                 285

Asn Gln Thr Ser Gln Ser Ile Ser Glu Asp Ala Val Leu Tyr Gln Lys
    290                 295                 300

Gln Glu Tyr Lys His Val Gln Asp Gly Tyr Glu Ile Asp Ile Lys Cys
305                 310                 315                 320

Asn Ser Ala Lys Gly Ser Val Ala Tyr Tyr Ile Ala Arg Val Arg Tyr
                325                 330                 335

Ala Arg Gln
```

<210> SEQ ID NO 31
<211> LENGTH: 921

-continued

```
<212> TYPE: DNA
<213> ORGANISM: Pseudoalteromonas phenolica

<400> SEQUENCE: 31
atgaaatcac tgttagaaaa aaatcaccca tcactatatg aaaaactgga aaatgaacaa      60
tgtaacgaaa aaaagcagga ggcttactac gagtttgtgc aatcttcaaa caagatagaa     120
aaagctgatt tttttacatt actaccagat aaaagagccg cgctcctcga cagtactgga     180
aagagtattg agaaagagct gaaaagttta gtcgacggct aagtgatat  tgctgatatg     240 gtagacaaga aaaaagcca  cagcgagata gcagataaaa tgatggatgt aggtgttgcg     300
gcatttggcg tattagccac tgaagcattt gaaaacacat tgaaagatca cgacaagata     360
acgacagaag tgatcaaaag tgcaattgaa atcgcactcg atgtggctga aaacctcggt     420
gaaatcgggg aaattattgc tgcaattatt ttagtcatca ttccgataat ttattttatg     480
ctgaaacccg catttacaac tgtacttatc atcaatgatt cagatgaaaa ttataagttc     540
ggaaaacact tcaatacaca tggcaaaacg acgtcttaca caacttccat aacatcaaca     600
tttgaaaaag atgggcaaac cttctccaat gcgggttttt tcacatcttc taaaaaagat     660
ggagcactct acggcacaca atcagggttt acgctactaa ccggtcagga aacgctcgca     720
tttggtgctg aatgtccttt aaatggcagc aataattgtt attgtgagtt cgataaatct     780
gcagagcaaa tctcaaaact gacagagaaa aagaaagatc tgtaccatga agtaagcaaa     840
ggaggcttag gcttaaatat tcgtggcaac tctaaatctg gtggcttagc ttggtttatt     900
ggccgaattt ataacacgta g                                                921

<210> SEQ ID NO 32
<211> LENGTH: 306
<212> TYPE: PRT
<213> ORGANISM: Pseudoalteromonas phenolica

<400> SEQUENCE: 32

Met Lys Ser Leu Leu Glu Lys Asn His Pro Ser Leu Tyr Glu Lys Leu
1               5                   10                  15

Glu Asn Glu Gln Cys Asn Glu Lys Lys Gln Glu Ala Tyr Tyr Glu Phe
            20                  25                  30

Val Gln Ser Ser Asn Lys Ile Glu Lys Ala Asp Phe Phe Thr Leu Leu
        35                  40                  45

Pro Asp Lys Arg Ala Ala Leu Leu Asp Ser Thr Gly Lys Ser Ile Glu
    50                  55                  60

Lys Glu Leu Lys Ser Leu Val Asp Gly Leu Ser Asp Ile Ala Asp Met
65                  70                  75                  80

Val Asp Lys Lys Lys Ser His Ser Glu Ile Ala Asp Lys Met Met Asp
                85                  90                  95

Val Gly Val Ala Ala Phe Gly Val Leu Ala Thr Glu Ala Phe Glu Asn
            100                 105                 110

Thr Leu Lys Asp His Asp Lys Ile Thr Thr Glu Val Ile Lys Ser Ala
        115                 120                 125

Ile Glu Ile Ala Leu Asp Val Ala Glu Asn Leu Gly Glu Ile Gly Glu
    130                 135                 140

Ile Ile Ala Ala Ile Ile Leu Val Ile Ile Pro Ile Ile Tyr Phe Met
145                 150                 155                 160

Leu Lys Pro Ala Phe Thr Thr Val Leu Ile Ile Asn Asp Ser Asp Glu
                165                 170                 175

Asn Tyr Lys Phe Gly Lys His Phe Asn Thr His Gly Lys Thr Thr Ser
```

```
                    180                 185                 190
Tyr Thr Thr Ser Ile Thr Ser Thr Phe Glu Lys Asp Gly Gln Thr Phe
                195                 200                 205
Ser Asn Ala Gly Phe Phe Thr Ser Ser Lys Lys Asp Gly Ala Leu Tyr
                210                 215                 220
Gly Thr Gln Ser Gly Phe Thr Leu Leu Thr Gly Gln Glu Thr Leu Ala
225                 230                 235                 240
Phe Gly Ala Glu Cys Pro Leu Asn Gly Ser Asn Asn Cys Tyr Cys Glu
                245                 250                 255
Phe Asp Lys Ser Ala Glu Gln Ile Ser Lys Leu Thr Glu Lys Lys Lys
                260                 265                 270
Asp Leu Tyr His Glu Val Ser Lys Gly Gly Leu Gly Leu Asn Ile Arg
                275                 280                 285
Gly Asn Ser Lys Ser Gly Gly Leu Ala Trp Phe Ile Gly Arg Ile Tyr
                290                 295                 300
Asn Thr
305

<210> SEQ ID NO 33
<211> LENGTH: 35
<212> TYPE: DNA
<213> ORGANISM: Artificial sequence
<220> FEATURE:
<223> OTHER INFORMATION: Synthetic sequence

<400> SEQUENCE: 33
aaaggatcca tgcatacaac aattgatatt gatct                          35

<210> SEQ ID NO 34
<211> LENGTH: 30
<212> TYPE: DNA
<213> ORGANISM: Artificial sequence
<220> FEATURE:
<223> OTHER INFORMATION: Synthetic sequence

<400> SEQUENCE: 34
tttctcgagc tatttttttaa atgcacgagc                               30

<210> SEQ ID NO 35
<211> LENGTH: 59
<212> TYPE: DNA
<213> ORGANISM: Artificial sequence
<220> FEATURE:
<223> OTHER INFORMATION: Synthetic sequence

<400> SEQUENCE: 35
actggtggac agcaaatggg tcgcggatcc atgcamacta caattgatat cgatcttaa  59

<210> SEQ ID NO 36
<211> LENGTH: 51
<212> TYPE: DNA
<213> ORGANISM: Artificial sequence
<220> FEATURE:
<223> OTHER INFORMATION: Synthetic sequence

<400> SEQUENCE: 36
ctcgagtgcg gccgcaagct tttaagcttt atatgctcgt gctacgtaat a          51

<210> SEQ ID NO 37
<211> LENGTH: 59
<212> TYPE: DNA
<213> ORGANISM: Artificial sequence
```

```
<220> FEATURE:
<223> OTHER INFORMATION: Synthetic sequence

<400> SEQUENCE: 37
actggtggac agcaaatggg tcgcggatcc atgcamacta caattgatat cgatcttaa      59

<210> SEQ ID NO 38
<211> LENGTH: 51
<212> TYPE: DNA
<213> ORGANISM: Artificial sequence
<220> FEATURE:
<223> OTHER INFORMATION: Synthetic sequence

<400> SEQUENCE: 38
ctcgagtgcg gccgcaagct tctatgcttt atatgcgcgt gctacataat a              51

<210> SEQ ID NO 39
<211> LENGTH: 57
<212> TYPE: DNA
<213> ORGANISM: Artificial sequence
<220> FEATURE:
<223> OTHER INFORMATION: Synthetic sequence

<400> SEQUENCE: 39
ccgcgcggca gcatcgaggg aaggcatatg caaattkcac atgatattga tttaagg        57

<210> SEQ ID NO 40
<211> LENGTH: 60
<212> TYPE: DNA
<213> ORGANISM: Artificial sequence
<220> FEATURE:
<223> OTHER INFORMATION: Synthetic sequence

<400> SEQUENCE: 40
ctttcgactg agcctttcgt tttactcgag ttatgatcga tatgcacgag caacgtagta     60

<210> SEQ ID NO 41
<211> LENGTH: 59
<212> TYPE: DNA
<213> ORGANISM: Artificial sequence
<220> FEATURE:
<223> OTHER INFORMATION: Synthetic sequence

<400> SEQUENCE: 41
actggtggac agcaaatggg tcgcggatcc atgcamacta caattgatat cgatcttaa      59

<210> SEQ ID NO 42
<211> LENGTH: 51
<212> TYPE: DNA
<213> ORGANISM: Artificial sequence
<220> FEATURE:
<223> OTHER INFORMATION: Synthetic sequence

<400> SEQUENCE: 42
ctcgagtgcg gccgcaagct tttatgcttt aaatgctcgt gctacgtagt a              51

<210> SEQ ID NO 43
<211> LENGTH: 59
<212> TYPE: DNA
<213> ORGANISM: Artificial sequence
<220> FEATURE:
<223> OTHER INFORMATION: Synthetic sequence

<400> SEQUENCE: 43
actggtggac agcaaatggg tcgcggatcc atgcamacta caattgatat cgatcttaa      59
```

<210> SEQ ID NO 44
<211> LENGTH: 51
<212> TYPE: DNA
<213> ORGANISM: Artificial sequence
<220> FEATURE:
<223> OTHER INFORMATION: Synthetic sequence

<400> SEQUENCE: 44

```
ctcgagtgcg gccgcaagct tttaggcttt aaatgctcgt gcaacgtaat a            51
```

<210> SEQ ID NO 45
<211> LENGTH: 984
<212> TYPE: DNA
<213> ORGANISM: Artificial sequence
<220> FEATURE:
<223> OTHER INFORMATION: Synthetic sequence

<400> SEQUENCE: 45

```
atgcatacaa caattgatat tgatcttaaa ttaaaacagg gatttcgaac tttatttcca    60
gaatacgcag caaaattaga gaaagctact tctcaagtgg aaatcaataa gcttcaagcg   120
gaattcattg aggaacgaaa gcaaatatta gctgaagctt taggcaagga tatatctgag   180
ctaaaagcaa gtgatcagac agcaccaatt ccattgtctg gggacacgta taaatgctt    240
atcaatgcaa caggtgatga cattaaaaga cagcttcatg ttctgataga tggtcttgaa   300
cgattaaaag gaatggaaaa agatgaagct ggtcttgtga ctgcacaaat tgtactttct   360
ggtgcgttag gaattggatc tttagcaacg attgaagttg taagaaactt agcaatgggt   420
gcggcagaaa cagtggctgc ctttgctgga gtaacagttg caacagttgg agtagttgta   480
gcagttgcat ctcttgtaat tgtgggtgtt attatcccaa ttatttactt tatgcaaaaa   540
ccagcaaatg ctattgtact tttaatcaat gaattggacg aacctcttgt atttgaaaca   600
gagcataatg ttcatggtaa accaatgtta atgacaacgc caattcctaa aggagtcgtg   660
attcctggtg taggtacata tgctactgca ggatttatcg caaccgaaaa aagagaaaat   720
gctttagtgg aacacaata tggttttaca atgcgatata agatactaa attatctttt   780
ggtgttgaat gtcctttaac agctatttat actgataata attgttattg tgccatagac   840
gaaagtgcta aaacagttgc ggaaagaact tccgataaaa ataagcaatt ctgggaagca   900
gaaaaagacg gcctcaaatt gagcattcgt tgcaattctg gtagtggctc aatcgcttac   960
tacgtagcac gagcatttaa agca                                          984
```

<210> SEQ ID NO 46
<211> LENGTH: 328
<212> TYPE: PRT
<213> ORGANISM: Artificial sequence
<220> FEATURE:
<223> OTHER INFORMATION: Synthetic sequence

<400> SEQUENCE: 46

```
Met His Thr Thr Ile Asp Ile Asp Leu Lys Leu Lys Gln Gly Phe Arg
1               5                   10                  15

Thr Leu Phe Pro Glu Tyr Ala Ala Lys Leu Glu Lys Ala Thr Ser Gln
            20                  25                  30

Val Glu Ile Asn Lys Leu Gln Ala Glu Phe Ile Glu Glu Arg Lys Gln
        35                  40                  45

Ile Leu Ala Glu Ala Leu Gly Lys Asp Ile Ser Glu Leu Lys Ala Ser
    50                  55                  60

Asp Gln Thr Ala Pro Ile Pro Leu Ser Gly Asp Thr Tyr Lys Met Leu
```

```
                65                  70                  75                  80
Ile Asn Ala Thr Gly Asp Asp Ile Lys Arg Gln Leu His Val Leu Ile
                    85                  90                  95

Asp Gly Leu Glu Arg Leu Lys Gly Met Glu Lys Asp Glu Ala Gly Leu
                100                 105                 110

Val Thr Ala Gln Ile Val Leu Ser Gly Ala Leu Gly Ile Gly Ser Leu
                115                 120                 125

Ala Thr Ile Glu Val Val Arg Asn Leu Ala Met Gly Ala Ala Glu Thr
130                 135                 140

Val Ala Ala Phe Ala Gly Val Thr Val Ala Thr Val Gly Val Val
145                 150                 155                 160

Ala Val Ala Ser Leu Val Ile Val Gly Val Ile Pro Ile Ile Tyr
                165                 170                 175

Phe Met Gln Lys Pro Ala Asn Ala Ile Val Leu Leu Ile Asn Glu Leu
                180                 185                 190

Asp Glu Pro Leu Val Phe Glu Thr Glu His Asn Val His Gly Lys Pro
                195                 200                 205

Met Leu Met Thr Thr Pro Ile Pro Lys Gly Val Val Ile Pro Gly Val
                210                 215                 220

Gly Thr Tyr Ala Thr Ala Gly Phe Ile Ala Thr Glu Lys Arg Glu Asn
225                 230                 235                 240

Ala Leu Val Gly Thr Gln Tyr Gly Phe Thr Met Arg Tyr Lys Asp Thr
                245                 250                 255

Lys Leu Ser Phe Gly Val Glu Cys Pro Leu Thr Ala Ile Tyr Thr Asp
                260                 265                 270

Asn Asn Cys Tyr Cys Ala Ile Asp Glu Ser Ala Lys Thr Val Ala Glu
                275                 280                 285

Arg Thr Ser Asp Lys Asn Lys Gln Phe Trp Glu Ala Glu Lys Asp Gly
                290                 295                 300

Leu Lys Leu Ser Ile Arg Cys Asn Ser Gly Ser Gly Ser Ile Ala Tyr
305                 310                 315                 320

Tyr Val Ala Arg Ala Phe Lys Ala
                325

<210> SEQ ID NO 47
<211> LENGTH: 984
<212> TYPE: DNA
<213> ORGANISM: Artificial sequence
<220> FEATURE:
<223> OTHER INFORMATION: Synthetic sequence

<400> SEQUENCE: 47
atgcaaacta caattgatat cgatcttaag ttaaaacagg ggttccggtc attattcccg      60
gattatgcaa caaagctaga gagggcgact tctcaagagg aaatcaataa acttcaggca     120
attttcattg aggaaagaaa gcaagcgctg gccgacgctt taggtaaaga catcagcgag     180
ctagaggcga gtgaccaaac cgcaccaatt cctttgaaaa aggaaacgta tgaaattctt     240
atcaatgcaa cgggtgacga catcaaaaga caaattcatg tcattattga tggtcttgaa     300
cgattaaagg ggatggaaaa tgacgaggca ggtcttgtca ctgcacaaat tcttctttcc     360
ggtgtattag gagtcggctt tttatcaacg tcgaccgtag tggcaaaatt ggcagtgggc     420
gcagcagagg caatcgccgc cttagctggt gtctcagttg caacagttgg agtagttgta     480
gcagttgcat ctcttgtaat tgtgggtgtt attatcccaa ttatttactt tatgcaaaaa     540
ccagcaaatg ctattgtact tttaatcaat gaattggacg aacctcttgt atttgaaaca     600
```

```
gagcataatg ttcatggtaa accaatgtta atgacaacgc caattcctaa aggagtcgtg    660
attcctggtg taggtacata tgctactgca ggatttatcg caaccgaaaa aagagaaaat    720
gctttagtgg aacacaata tggttttaca atgcgatata aagatactaa attatctttt    780
ggtgttgaat gtcctttaac agctatttat actgataata attgttattg tgccatagat    840
gaaagtgctg tgacagttgc agaaatgact acaaaaaaga ataagcaata ttgggagcat    900
aataaaaacg gcataggatt gagcattcgt tgcaactctg gaagtggatc aatagcttat    960
tacgtagctc gtgcatttaa aaaa                                           984
```

<210> SEQ ID NO 48
<211> LENGTH: 328
<212> TYPE: PRT
<213> ORGANISM: Artificial sequence
<220> FEATURE:
<223> OTHER INFORMATION: Synthetic sequence

<400> SEQUENCE: 48

```
Met Gln Thr Thr Ile Asp Ile Asp Leu Lys Leu Lys Gln Gly Phe Arg
1               5                   10                  15

Ser Leu Phe Pro Asp Tyr Ala Thr Lys Leu Glu Arg Ala Thr Ser Gln
            20                  25                  30

Glu Glu Ile Asn Lys Leu Gln Ala Ile Phe Ile Glu Glu Arg Lys Gln
        35                  40                  45

Ala Leu Ala Asp Ala Leu Gly Lys Asp Ile Ser Glu Leu Glu Ala Ser
    50                  55                  60

Asp Gln Thr Ala Pro Ile Pro Leu Lys Lys Glu Thr Tyr Glu Ile Leu
65                  70                  75                  80

Ile Asn Ala Thr Gly Asp Asp Ile Lys Arg Gln Ile His Val Ile Ile
                85                  90                  95

Asp Gly Leu Glu Arg Leu Lys Gly Met Glu Asn Asp Glu Ala Gly Leu
            100                 105                 110

Val Thr Ala Gln Ile Leu Leu Ser Gly Val Leu Gly Val Gly Phe Leu
        115                 120                 125

Ser Thr Ser Thr Val Val Ala Lys Leu Ala Val Gly Ala Ala Glu Ala
    130                 135                 140

Ile Ala Ala Leu Ala Gly Val Ser Val Ala Thr Val Gly Val Val Val
145                 150                 155                 160

Ala Val Ala Ser Leu Val Ile Val Gly Val Ile Ile Pro Ile Tyr
                165                 170                 175

Phe Met Gln Lys Pro Ala Asn Ala Ile Val Leu Leu Ile Asn Glu Leu
            180                 185                 190

Asp Glu Pro Leu Val Phe Glu Thr Glu His Asn Val His Gly Lys Pro
        195                 200                 205

Met Leu Met Thr Thr Pro Ile Pro Lys Gly Val Val Ile Pro Gly Val
    210                 215                 220

Gly Thr Tyr Ala Thr Ala Gly Phe Ile Ala Thr Glu Lys Arg Glu Asn
225                 230                 235                 240

Ala Leu Val Gly Thr Gln Tyr Gly Phe Thr Met Arg Tyr Lys Asp Thr
                245                 250                 255

Lys Leu Ser Phe Gly Val Glu Cys Pro Leu Thr Ala Ile Tyr Thr Asp
            260                 265                 270

Asn Asn Cys Tyr Cys Ala Ile Asp Glu Ser Ala Val Thr Val Ala Glu
        275                 280                 285
```

Met Thr Thr Lys Lys Asn Lys Gln Tyr Trp Glu His Asn Lys Asn Gly
    290                 295                 300
Ile Gly Leu Ser Ile Arg Cys Asn Ser Gly Ser Ile Ala Tyr
305                 310                 315                 320
Tyr Val Ala Arg Ala Phe Lys Lys
                325

<210> SEQ ID NO 49
<211> LENGTH: 984
<212> TYPE: DNA
<213> ORGANISM: Artificial sequence
<220> FEATURE:
<223> OTHER INFORMATION: Synthetic sequence

<400> SEQUENCE: 49

```
atgcaaacta caattgatat cgatcttaag ttaaaacagg ggttccggtc attattcccg      60
gattatgcaa caaagctaga gagggcgact tctcaagagg aaatcaataa acttcaggca     120
attttcattg aggaaagaaa gcaagcgctg gccgacgctt taggtaaaga catcagcgag     180
ctagaggcga gtgaccaaac cgcaccaatt cctttgaaaa aggaaacgta tgaaattctt     240
atcaatgcaa cgggtgacga catcaaaaga caaattcatg tcattattga tggtcttgaa     300
cgattaaaag gaatggaaaa agatgaagct ggtcttgtga ctgcacaaat tgtactttct     360
ggtgcgttag gaattggatc tttagcaacg attgaagttg taagaaactt agcaatgggt     420
gcggcagaaa cagtggctgc ctttgctgga gtaacagttg caacagttgg agtagttgta     480
gcagttgcat ctcttgtaat tgtgggtgtt attatcccaa ttatttactt tatgcaaaaa     540
ccagcaaatg ctattgtact tttaatcaat gaattggacg aacctcttgt atttgaaaca     600
gagcataatt tcatggtaa accaatgtta atgacaacgc caattcctaa aggagtcgtg     660
attcctggtg taggtacata tgctactgca ggatttatcg caaccgaaaa aagagaaaat     720
gctttagtgg aaacacaata tggttttaca atgcgatata agatactaa attatctttt     780
ggtgttgaat gtcctttaac agctatttat actgataata attgttattg tgccatagat     840
gaaagtgctg tgacagttgc agaaatgact acaaaaaaga ataagcaata ttgggagcat     900
aataaaaacg gcataggatt gagcattcgt tgcaactctg gaagtggatc aatagcttat     960
tacgtagctc gtgcatttaa aaaa                                           984
```

<210> SEQ ID NO 50
<211> LENGTH: 328
<212> TYPE: PRT
<213> ORGANISM: Artificial sequence
<220> FEATURE:
<223> OTHER INFORMATION: Synthetic sequence

<400> SEQUENCE: 50

Met Gln Thr Thr Ile Asp Ile Asp Leu Lys Leu Lys Gln Gly Phe Arg
1                   5                   10                  15

Ser Leu Phe Pro Asp Tyr Ala Thr Lys Leu Glu Arg Ala Thr Ser Gln
                20                  25                  30

Glu Glu Ile Asn Lys Leu Gln Ala Ile Phe Ile Glu Glu Arg Lys Gln
        35                  40                  45

Ala Leu Ala Asp Ala Leu Gly Lys Asp Ile Ser Glu Leu Glu Ala Ser
    50                  55                  60

Asp Gln Thr Ala Pro Ile Pro Leu Lys Lys Glu Thr Tyr Glu Ile Leu
65                  70                  75                  80

Ile Asn Ala Thr Gly Asp Asp Ile Lys Arg Gln Ile His Val Ile Ile

```
                    85                  90                  95
Asp Gly Leu Glu Arg Leu Lys Gly Met Glu Lys Asp Glu Ala Gly Leu
                100                 105                 110

Val Thr Ala Gln Ile Val Leu Ser Gly Ala Leu Gly Ile Gly Ser Leu
            115                 120                 125

Ala Thr Ile Glu Val Val Arg Asn Leu Ala Met Gly Ala Ala Glu Thr
        130                 135                 140

Val Ala Ala Phe Ala Gly Val Thr Val Ala Thr Val Gly Val Val Val
145                 150                 155                 160

Ala Val Ala Ser Leu Val Ile Val Gly Val Ile Pro Ile Tyr
                165                 170                 175

Phe Met Gln Lys Pro Ala Asn Ala Ile Val Leu Leu Ile Asn Glu Leu
                180                 185                 190

Asp Glu Pro Leu Val Phe Glu Thr Glu His Asn Val His Gly Lys Pro
            195                 200                 205

Met Leu Met Thr Thr Pro Ile Pro Lys Gly Val Val Ile Pro Gly Val
        210                 215                 220

Gly Thr Tyr Ala Thr Ala Gly Phe Ile Ala Thr Glu Lys Arg Glu Asn
225                 230                 235                 240

Ala Leu Val Gly Thr Gln Tyr Gly Phe Thr Met Arg Tyr Lys Asp Thr
                245                 250                 255

Lys Leu Ser Phe Gly Val Glu Cys Pro Leu Thr Ala Ile Tyr Thr Asp
                260                 265                 270

Asn Asn Cys Tyr Cys Ala Ile Asp Glu Ser Ala Val Thr Val Ala Glu
            275                 280                 285

Met Thr Thr Lys Lys Asn Lys Gln Tyr Trp Glu His Asn Lys Asn Gly
        290                 295                 300

Ile Gly Leu Ser Ile Arg Cys Asn Ser Gly Ser Gly Ser Ile Ala Tyr
305                 310                 315                 320

Tyr Val Ala Arg Ala Phe Lys Lys
                325

<210> SEQ ID NO 51
<211> LENGTH: 984
<212> TYPE: DNA
<213> ORGANISM: Artificial sequence
<220> FEATURE:
<223> OTHER INFORMATION: Synthetic sequence

<400> SEQUENCE: 51
atgcaaacta caattgatat cgatcttaag ttaaaacagg ggttccggtc attattcccg      60
gattatgcaa caaagctaga gagggcgact tctcaagagg aaatcaataa acttcaggca     120
attttcattg aggaaagaaa gcaagcgctg gccgacgctt taggtaaaga catcagcgag     180
ctagaggcga gtgaccaaac cgcaccaatt cctttgaaaa aggaaacgta tgaaattctt     240
atcaatgcaa cgggtgacga catcaaaaga caaattcatg tcattattga tggtcttgaa     300
cgattaaagg ggatggaaaa tgacgaggca ggtcttgtca ctgcacaaat tcttctttcc     360
ggtgtattag gagtcggctt tttatcaacg tcgaccgtag tggcaaaatt ggcagtgggc     420
gcagcagagg caatcgccgc cttagctggt gtctcagttg caacagttgg agtagtggtg     480
gcagttgcgg cgcttgttat cgtagctatc attattccta tcatttattt tatgaaaaaa     540
ccagcaaatg cctatagtgtt gttaattaat gaattggaca acctcttac atttgttagt     600 gaccataatg ttcatggtaa accaatgtta atgacaacgc caattcctaa aggagtcgtg     660
```

```
attcctggtg taggtacata tgctactgca ggatttatcg caaccgaaaa aagagaaaat    720
gctttagtgg aaacacaata tggttttaca atgcgatata aagatactaa attatctttt    780
ggtgttgaat gtcctttaac agctatttat actgataata attgttattg tgccatagat    840
gaaagtgctg tgacagttgc agaaatgact acaaaaaaga ataagcaata ttgggagcat    900
aataaaaacg gcataggatt gagcattcgt tgcaactctg gaagtggatc aatagcttat    960
tacgtagctc gtgcatttaa aaaa                                          984
```

<210> SEQ ID NO 52
<211> LENGTH: 328
<212> TYPE: PRT
<213> ORGANISM: Artificial sequence
<220> FEATURE:
<223> OTHER INFORMATION: Synthetic sequence

<400> SEQUENCE: 52

Met Gln Thr Thr Ile Asp Ile Asp Leu Lys Leu Lys Gln Gly Phe Arg
1               5                   10                  15

Ser Leu Phe Pro Asp Tyr Ala Thr Lys Leu Glu Arg Ala Thr Ser Gln
            20                  25                  30

Glu Glu Ile Asn Lys Leu Gln Ala Ile Phe Ile Glu Glu Arg Lys Gln
        35                  40                  45

Ala Leu Ala Asp Ala Leu Gly Lys Asp Ile Ser Glu Leu Glu Ala Ser
    50                  55                  60

Asp Gln Thr Ala Pro Ile Pro Leu Lys Lys Glu Thr Tyr Glu Ile Leu
65                  70                  75                  80

Ile Asn Ala Thr Gly Asp Asp Ile Lys Arg Gln Ile His Val Ile Ile
                85                  90                  95

Asp Gly Leu Glu Arg Leu Lys Gly Met Glu Asn Asp Glu Ala Gly Leu
            100                 105                 110

Val Thr Ala Gln Ile Leu Leu Ser Gly Val Leu Gly Val Gly Phe Leu
        115                 120                 125

Ser Thr Ser Thr Val Val Ala Lys Leu Ala Val Gly Ala Ala Glu Ala
    130                 135                 140

Ile Ala Ala Leu Ala Gly Val Ser Val Ala Thr Val Gly Val Val Val
145                 150                 155                 160

Ala Val Ala Ala Leu Val Ile Val Ala Ile Ile Pro Ile Ile Tyr
                165                 170                 175

Phe Met Lys Lys Pro Ala Asn Ala Ile Val Leu Leu Ile Asn Glu Leu
            180                 185                 190

Asp Lys Pro Leu Thr Phe Val Ser Asp His Asn Val His Gly Lys Pro
        195                 200                 205

Met Leu Met Thr Thr Pro Ile Pro Lys Gly Val Val Ile Pro Gly Val
    210                 215                 220

Gly Thr Tyr Ala Thr Ala Gly Phe Ile Ala Thr Glu Lys Arg Glu Asn
225                 230                 235                 240

Ala Leu Val Gly Thr Gln Tyr Gly Phe Thr Met Arg Tyr Lys Asp Thr
                245                 250                 255

Lys Leu Ser Phe Gly Val Glu Cys Pro Leu Thr Ala Ile Tyr Thr Asp
            260                 265                 270

Asn Asn Cys Tyr Cys Ala Ile Asp Glu Ser Ala Val Thr Val Ala Glu
        275                 280                 285

Met Thr Thr Lys Lys Asn Lys Gln Tyr Trp Glu His Asn Lys Asn Gly
    290                 295                 300

Ile Gly Leu Ser Ile Arg Cys Asn Ser Gly Gly Ser Ile Ala Tyr
305                 310                 315                 320

Tyr Val Ala Arg Ala Phe Lys Lys
                325

<210> SEQ ID NO 53
<211> LENGTH: 990
<212> TYPE: DNA
<213> ORGANISM: Artificial sequence
<220> FEATURE:
<223> OTHER INFORMATION: Synthetic sequence

<400> SEQUENCE: 53

```
atgcaaacta caattgatat cgatcttaag ttaaaacagg ggttccggtc attattcccg      60
gattatgcaa caaagctaga gagggcgact tctcaagagg aaatcaataa acttcaggca     120
attttcattg aggaaagaaa gcaagcgctg gccgacgctt taggtaaaga catcagcgag     180
ctagaggcga gtgaccaaac cgcaccaatt cctttgaaaa aggaaacgta tgaaattctt     240
atcaatgcaa cgggtgacga catcaaaaga caaattcatg tcattattga tggtcttgaa     300
cgattaaagg ggatggaaaa tgacgaggca ggtcttgtca ctgcacaaat tcttctttcc     360
ggtgtattag gagtcggctt tttatcaacg tcgaccgtag tggcaaaatt ggcagtgggc     420
gcagcagagg caatcgccgc cttagctggt gtctcagttg caacagttgg agtagtggtg     480
gcagttgcgg cgcttgttat cgtagctatc attattccta tcatttattt tatgaaaaaa     540
ccagcaaatg ccatagtgtt gttaattaat gaattggaca acctcttac atttgttagt     600
gaccataatg ttcatggcaa accaatgctg atgactacgc ctattcctga aggtgtcgag     660
attcctgggg ttgctaaata tccagtagcc ggattaattg caaccgagaa gcgagatagt     720
gctttagtcg ggacacaata tggcttcaca atgaaatatg caatacagg tactaattt     780
tcattcggcg tagaatgtcc gttaacatcc atttctactg ataataattg ttattgtgcc     840
atagatgaaa gtgctgtgac agttgcagaa atgactacaa aaagaataa gcaatattgg     900
gagcataata aaaacggcat aggattgagc attcgttgca actctggaag tggatcaata     960
gcttattacg tagctcgtgc atttaaaaaa                                      990
```

<210> SEQ ID NO 54
<211> LENGTH: 329
<212> TYPE: PRT
<213> ORGANISM: Artificial sequence
<220> FEATURE:
<223> OTHER INFORMATION: Synthetic sequence

<400> SEQUENCE: 54

Met Gln Thr Thr Ile Asp Ile Asp Leu Lys Leu Lys Gln Gly Phe Arg
1               5                   10                  15

Ser Leu Phe Pro Asp Tyr Ala Thr Lys Leu Glu Arg Ala Thr Ser Gln
                20                  25                  30

Glu Glu Ile Asn Lys Leu Gln Ala Ile Phe Ile Glu Glu Arg Lys Gln
            35                  40                  45

Ala Leu Ala Asp Ala Leu Gly Lys Asp Ile Ser Glu Leu Glu Ala Ser
        50                  55                  60

Asp Gln Thr Ala Pro Ile Pro Leu Lys Lys Glu Thr Tyr Glu Ile Leu
65                  70                  75                  80

Ile Asn Ala Thr Gly Asp Asp Ile Lys Arg Gln Ile His Val Ile Ile
                85                  90                  95

Asp Gly Leu Glu Arg Leu Lys Gly Met Glu Asn Asp Glu Ala Gly Leu

|     |     |     | 100 |     |     |     | 105 |     |     |     | 110 |
| --- | --- | --- | --- | --- | --- | --- | --- | --- | --- | --- | --- |

Val Thr Ala Gln Ile Leu Leu Ser Gly Val Leu Gly Val Gly Phe Leu
            115                 120                 125

Ser Thr Ser Thr Val Val Ala Lys Leu Ala Val Gly Ala Ala Glu Ala
        130                 135                 140

Ile Ala Ala Leu Ala Gly Val Ser Val Ala Thr Val Gly Val Val Val
145                 150                 155                 160

Ala Val Ala Ala Leu Val Ile Val Ala Ile Ile Pro Ile Ile Tyr
                165                 170                 175

Phe Met Lys Lys Pro Ala Asn Ala Ile Val Leu Leu Ile Asn Glu Leu
                180                 185                 190

Asp Lys Pro Leu Thr Phe Val Ser Asp His Asn Val His Gly Lys Pro
            195                 200                 205

Met Leu Met Thr Thr Pro Ile Pro Glu Gly Val Glu Ile Pro Gly Val
        210                 215                 220

Ala Lys Tyr Pro Val Ala Gly Leu Ile Ala Thr Lys Arg Asp Ser Ala
225                 230                 235                 240

Leu Val Gly Thr Gln Tyr Gly Phe Thr Met Lys Tyr Gly Asn Thr Gly
                245                 250                 255

Thr Asn Phe Ser Phe Gly Val Glu Cys Pro Leu Thr Ser Ile Ser Thr
            260                 265                 270

Asp Asn Asn Cys Tyr Cys Ala Ile Asp Glu Ser Ala Val Thr Val Ala
        275                 280                 285

Glu Met Thr Thr Lys Lys Asn Lys Gln Tyr Trp Glu His Asn Lys Asn
290                 295                 300

Gly Ile Gly Leu Ser Ile Arg Cys Asn Ser Gly Ser Gly Ser Ile Ala
305                 310                 315                 320

Tyr Tyr Val Ala Arg Ala Phe Lys Lys
                325

<210> SEQ ID NO 55
<211> LENGTH: 996
<212> TYPE: DNA
<213> ORGANISM: Flavobacterium crassostreae

<400> SEQUENCE: 55

| | | | | | |
|---|---|---|---|---|---|
| atgttcacaa | aatctgaatt | aataaattta | aaaacatctt | ttggtaatgc | ctatcctgat | 60 |
| tatttcaagc | aattagaggc | ctgtaataca | caacaagaac | tagcggatac | ttacgaaaaa | 120 |
| attaaagcag | acgcttttga | aaaagctaaa | ccctttttag | cagagggaga | tgatcctact | 180 |
| ggatttcctg | caattgcact | tactacacaa | cagtataata | acttgatttc | tgcacaaggg | 240 |
| gataatatca | aagtttacgt | tacagcaatg | ataaatacgg | cacaactaat | tcagccaagt | 300 |
| tttaacgttg | gtcaaactgt | agctagttta | atgggtggag | gaattacggc | catcggaaca | 360 |
| attgcaggtg | cagcatttgg | tgagggtatt | gtgggaggta | tggttgctac | attagcggtt | 420 |
| gcagcaggtg | ttgaagccgt | tacagttgca | ggattagtga | cattgatagc | tgttgcaatt | 480 |
| atagctatca | ttataccaat | catttatttc | atgcttaaac | cagcttgttg | ctttgttgta | 540 |
| gtgttaaatg | aaacaaataa | tcaattaaat | tgggttgatg | attacaatgt | acatggtaag | 600 |
| ccaattggtc | atactccttt | tattagtgca | gctatagata | tacctcagcc | aatacctggc | 660 |
| gctggtagat | atgtttattg | tggcttagtg | caaacagaca | aaagagatgc | tgcattagtt | 720 |
| ggaactcaat | acgatttac | atactctgga | aattcaggag | cttacaaagc | taattttggg | 780 |
| gttgaatgtc | cattaacaag | tttgtatgta | gacaataact | gcttttgtga | aattggttct | 840 |

-continued

```
tcatctgaag atgctgccaa tcaaactgac tccaaaaatg tattgagcta tactgcctct    900
agtgtaaatc caaaactaga cgtaagtatt aactgtaatt caggttctgg gtatgtagct    960
tattacatag ctagagttaa ggatggatct ttaaat                              996
```

<210> SEQ ID NO 56
<211> LENGTH: 332
<212> TYPE: PRT
<213> ORGANISM: Flavobacterium crassostreae

<400> SEQUENCE: 56

```
Met Phe Thr Lys Ser Glu Leu Ile Asn Leu Lys Thr Ser Phe Gly Asn
1               5                   10                  15

Ala Tyr Pro Asp Tyr Phe Lys Gln Leu Glu Ala Cys Asn Thr Gln Gln
            20                  25                  30

Glu Leu Ala Asp Thr Tyr Glu Lys Ile Lys Ala Asp Ala Phe Glu Lys
        35                  40                  45

Ala Lys Pro Phe Leu Ala Glu Gly Asp Asp Pro Thr Gly Phe Pro Ala
    50                  55                  60

Ile Ala Leu Thr Thr Gln Gln Tyr Asn Asn Leu Ile Ser Ala Gln Gly
65                  70                  75                  80

Asp Asn Ile Lys Val Tyr Val Thr Ala Met Ile Asn Thr Ala Gln Leu
                85                  90                  95

Ile Gln Pro Ser Phe Asn Val Gly Gln Thr Val Ala Ser Leu Met Gly
            100                 105                 110

Gly Gly Ile Thr Ala Ile Gly Thr Ile Ala Gly Ala Ala Phe Gly Glu
        115                 120                 125

Gly Ile Val Gly Gly Met Val Ala Thr Leu Ala Val Ala Ala Gly Val
    130                 135                 140

Glu Ala Val Thr Val Ala Gly Leu Val Thr Leu Ile Ala Val Ala Ile
145                 150                 155                 160

Ile Ala Ile Ile Ile Pro Ile Ile Tyr Phe Met Leu Lys Pro Ala Cys
                165                 170                 175

Cys Phe Val Val Val Leu Asn Glu Thr Asn Asn Gln Leu Asn Trp Val
            180                 185                 190

Asp Asp Tyr Asn Val His Gly Lys Pro Ile Gly His Thr Pro Phe Ile
        195                 200                 205

Ser Ala Ala Ile Asp Ile Pro Gln Pro Ile Pro Gly Ala Gly Arg Tyr
    210                 215                 220

Val Tyr Cys Gly Leu Val Gln Thr Asp Lys Arg Asp Ala Ala Leu Val
225                 230                 235                 240

Gly Thr Gln Tyr Gly Phe Thr Tyr Ser Gly Asn Ser Gly Ala Tyr Lys
                245                 250                 255

Ala Asn Phe Gly Val Glu Cys Pro Leu Thr Ser Leu Tyr Val Asp Asn
            260                 265                 270

Asn Cys Phe Cys Glu Ile Gly Ser Ser Glu Asp Ala Ala Asn Gln
        275                 280                 285

Thr Asp Ser Lys Asn Val Leu Ser Tyr Thr Ala Ser Ser Val Asn Pro
    290                 295                 300

Lys Leu Asp Val Ser Ile Asn Cys Asn Ser Gly Ser Gly Tyr Val Ala
305                 310                 315                 320

Tyr Tyr Ile Ala Arg Val Lys Asp Gly Ser Leu Asn
                325                 330
```

```
<210> SEQ ID NO 57
<211> LENGTH: 985
<212> TYPE: DNA
<213> ORGANISM: Chryseobacterium sp.

<400> SEQUENCE: 57
atgtttacaa aactagaatt aatcaattta aaaacatctt tcaacactgc atatcctgaa      60
tattgcagtc aattagatgc ttgtacgact gagacagagt tattagaaac gtatgaaaaa     120
attaaagaag atgcgtttgc taaggctaaa ccatatttag cagcaggtga tgatcctacc     180
ggttttccgg cactggctct tactccacaa cagtataata atctgaaatc agcaacagga     240
tcaaatatca aagtgtatgt tacagcaatg cttaatcagg ctcaaataat tcagccaagt     300
ttcagtgttg gtcaaaccgt tgcaacactt ataggaggcg tcttactgc aataggtaca      360 attgccggag cagcatttgg taccggtatt ataggcggaa tggttgcatc tgttgcggtt     420
gctgcaggag taacagcagt taccgttgct ggtcttgtaa cgctgatagc agttgctatt     480
gttgcggtaa ttatccctat tctttatttt atgcttaaac cagcgtgttg ttttgtatta     540
gtattaaacg aaacaaataa tcagctgaca tggaagacg attataatgt tcatgggaag      600
cctatcggac atactccgca tattagtgct gccatagata ttcctgaacc tattcctgga     660
gctggtaaat atgtttatgc aggtcttgta caaacggata agagagatgc cgctttattt     720
ggaactcaat atggatttac ttacacagga gacgttggca agtataatgt taatttcggg     780
gcagaatgtc ctttaagcag tatttatgta gataataact gctattgtga aataggttcc     840
acatcagaaa attcagcacg tcaaacaact aaaaagaatg ctttgaccta ttctgcaaca     900
agtacaactc caaaacttga tacaagcatc aaatgtaatt ctgcatccgg atatgtagcc     960
tactatattg caagagttga ggatg                                           985

<210> SEQ ID NO 58
<211> LENGTH: 332
<212> TYPE: PRT
<213> ORGANISM: Chryseobacterium sp.

<400> SEQUENCE: 58
```

Met Phe Thr Lys Leu Glu Leu Ile Asn Leu Lys Thr Ser Phe Asn Thr
1               5                   10                  15

Ala Tyr Pro Glu Tyr Cys Ser Gln Leu Asp Ala Cys Thr Thr Glu Thr
            20                  25                  30

Glu Leu Leu Glu Thr Tyr Glu Lys Ile Lys Glu Asp Ala Phe Ala Lys
        35                  40                  45

Ala Lys Pro Tyr Leu Ala Ala Gly Asp Asp Pro Thr Gly Phe Pro Ala
    50                  55                  60

Leu Ala Leu Thr Pro Gln Gln Tyr Asn Asn Leu Lys Ser Ala Thr Gly
65                  70                  75                  80

Ser Asn Ile Lys Val Tyr Val Thr Ala Met Leu Asn Gln Ala Gln Ile
                85                  90                  95

Ile Gln Pro Ser Phe Ser Val Gly Gln Thr Val Ala Thr Leu Ile Gly
            100                 105                 110

Gly Gly Leu Thr Ala Ile Gly Thr Ile Ala Gly Ala Ala Phe Gly Thr
        115                 120                 125

Gly Ile Ile Gly Gly Met Val Ala Ser Val Ala Val Ala Ala Gly Val
    130                 135                 140

Thr Ala Val Thr Val Ala Gly Leu Val Thr Leu Ile Ala Val Ala Ile
145                 150                 155                 160

```
Val Ala Val Ile Ile Pro Ile Leu Tyr Phe Met Leu Lys Pro Ala Cys
                165                 170                 175

Cys Phe Val Leu Val Leu Asn Glu Thr Asn Asn Gln Leu Thr Trp Lys
            180                 185                 190

Asp Asp Tyr Asn Val His Gly Lys Pro Ile Gly His Thr Pro His Ile
        195                 200                 205

Ser Ala Ala Ile Asp Ile Pro Glu Pro Ile Pro Gly Ala Gly Lys Tyr
    210                 215                 220

Val Tyr Ala Gly Leu Val Gln Thr Asp Lys Arg Asp Ala Ala Leu Phe
225                 230                 235                 240

Gly Thr Gln Tyr Gly Phe Thr Tyr Thr Gly Asp Val Gly Lys Tyr Asn
                245                 250                 255

Val Asn Phe Gly Ala Glu Cys Pro Leu Ser Ser Ile Tyr Val Asp Asn
            260                 265                 270

Asn Cys Tyr Cys Glu Ile Gly Ser Thr Ser Glu Asn Ser Ala Arg Gln
        275                 280                 285

Thr Thr Lys Lys Asn Ala Leu Tyr Ser Ala Thr Ser Thr Thr Pro
    290                 295                 300

Lys Leu Asp Thr Ser Ile Lys Cys Asn Ser Ala Ser Gly Tyr Val Ala
305                 310                 315                 320

Tyr Tyr Ile Ala Arg Val Glu Asp Gly Ser Leu Ser
                325                 330
```

<210> SEQ ID NO 59
<211> LENGTH: 1068
<212> TYPE: DNA
<213> ORGANISM: Pseudovibrio sp.

<400> SEQUENCE: 59

```
atgggaaaaa ttcgaatcaa taaaaaacaa catcaaaaaa agatacaatt actttacaag      60
gaattagcaa agaaaataga aaataatgac atccataaag tattaacaaa actagaagta     120
aattacgatg aggaaaaatt aaatgaagca atatatgcaa taaaaactaa tctgaatcga     180 caagggcac tgatgaagca agcgcaattg ctttacgacc aaaaaaagt atttgaattt      240 attaatagta acggagataa aatacgagtg caggtccaaa aatacttgga tgatgtagag     300
cgtctctcaa aaatggaaga cgacgacgca attgaaatct ccatggccat tatcgggata     360
tcagcagcag ctgttggtgt aatcgccgga attactgtct tcgtgcaatt gatacgaggg     420
gttgggtacc tgactttcag catcgtgctg gctggtgtct tgtccgcagg tgctgccatt     480
gtcgttgcca tagcggcatt catagtcctt atgctgatct tcccattcct gtacttcatg     540
aacaagccgg cagtctgtat tgttgccctg atcaatgaac tcccgggatt agattttgac     600
tccgatctca ctggtttgaa aaacacgctg acatttccg acaactacaa cattcacggg      660
aaaccgacac tcatcacgaa ggaaatccca ggagctttgt tcacagacca aggcccttat      720
gcgtatattg gtctgtttgc aacatccaaa agagacaaag cactgatcgg tcctcagtat     780
ggcttcacac tggaactccc atattctaaa gatttacaca aggatgaagt taaaagtatg     840
acagccgctt ttggtgccgg ctgcccgctt gccttgggaa agaacaattg ctactgtgat     900
tttgatattt ctgccgaaaa agccgcaaaa aatgctaata acattccaa ccagacttgg     960 tatgcagaaa atgacggcgt aagtctcagc ataaagtgca attcaggcag cgggagcata    1020
gcctattaca tagctagagt ttacaagaca aaacattcaa taaataac                 1068
```

<210> SEQ ID NO 60

```
<211> LENGTH: 356
<212> TYPE: PRT
<213> ORGANISM: Pseudovibrio sp.

<400> SEQUENCE: 60

Met Gly Lys Ile Arg Ile Asn Lys Lys Gln His Gln Lys Lys Ile Gln
1               5                   10                  15

Leu Leu Tyr Lys Glu Leu Ala Lys Glu Ile Glu Asn Asn Asp Ile His
            20                  25                  30

Lys Val Leu Thr Lys Leu Glu Val Asn Tyr Asp Glu Lys Leu Asn
        35                  40                  45

Glu Ala Ile Tyr Ala Ile Lys Thr Asn Leu Asn Arg Gln Gly Ala Leu
50                  55                  60

Met Lys Gln Ala Gln Leu Leu Tyr Asp Pro Lys Lys Val Phe Glu Phe
65                  70                  75                  80

Ile Asn Ser Asn Gly Asp Lys Ile Arg Val Gln Val Gln Lys Tyr Leu
                85                  90                  95

Asp Asp Val Glu Arg Leu Ser Lys Met Glu Asp Asp Ala Ile Glu
            100                 105                 110

Ile Ser Met Ala Ile Gly Ile Ser Ala Ala Val Gly Val Ile
        115                 120                 125

Ala Gly Ile Thr Val Phe Val Gln Leu Ile Arg Gly Val Gly Tyr Leu
130                 135                 140

Thr Phe Ser Ile Val Leu Ala Gly Val Leu Ser Ala Gly Ala Ala Ile
145                 150                 155                 160

Val Val Ala Ile Ala Ala Phe Ile Val Leu Met Leu Ile Phe Pro Phe
                165                 170                 175

Leu Tyr Phe Met Asn Lys Pro Ala Val Cys Ile Val Ala Leu Ile Asn
            180                 185                 190

Glu Leu Pro Gly Leu Asp Phe Asp Ser Asp Leu Thr Gly Leu Lys Asn
        195                 200                 205

Thr Leu Thr Phe Ser Asp Asn Tyr Asn Ile His Gly Lys Pro Thr Leu
210                 215                 220

Ile Thr Lys Glu Ile Pro Gly Ala Leu Phe Thr Asp Gln Gly Pro Tyr
225                 230                 235                 240

Ala Tyr Ile Gly Leu Phe Ala Thr Ser Lys Arg Asp Lys Ala Leu Ile
                245                 250                 255

Gly Pro Gln Tyr Gly Phe Thr Leu Glu Leu Pro Tyr Ser Lys Asp Leu
            260                 265                 270

His Lys Asp Glu Val Lys Ser Met Thr Ala Ala Phe Gly Ala Gly Cys
        275                 280                 285

Pro Leu Ala Leu Gly Lys Asn Asn Cys Tyr Cys Asp Phe Asp Ile Ser
290                 295                 300

Ala Glu Lys Ala Ala Lys Asn Ala Asn Lys His Ser Asn Gln Thr Trp
305                 310                 315                 320

Tyr Ala Glu Asn Asp Gly Val Ser Leu Ser Ile Lys Cys Asn Ser Gly
                325                 330                 335

Ser Gly Ser Ile Ala Tyr Tyr Ile Ala Arg Val Tyr Lys Thr Lys His
            340                 345                 350

Ser Ile Asn Asn
        355

<210> SEQ ID NO 61
<211> LENGTH: 5
<212> TYPE: PRT
```

```
<213> ORGANISM: Artificial sequence
<220> FEATURE:
<223> OTHER INFORMATION: Synthetic sequence

<400> SEQUENCE: 61

Glu Glu Lys Lys Asn
1               5
```